United States Patent
Zhu et al.

(10) Patent No.: US 9,572,808 B2
(45) Date of Patent: *Feb. 21, 2017

(54) BENZENESULFONAMIDE DERIVATIVES OF QUINOXALINE, PHARMACEUTICAL COMPOSITIONS THEREOF, AND THEIR USE IN METHODS FOR TREATING CANCER

(71) Applicant: NEUPHARMA, INC., Foster City, CA (US)

(72) Inventors: Yong-Liang Zhu, Fremont, CA (US); Xiangping Qian, Foster City, CA (US)

(73) Assignee: NeuPharma, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/973,492

(22) Filed: Dec. 17, 2015

(65) Prior Publication Data
US 2016/0303118 A1 Oct. 20, 2016

Related U.S. Application Data

(63) Continuation of application No. 13/594,634, filed on Aug. 24, 2012, now Pat. No. 9,295,671.

(60) Provisional application No. 61/528,033, filed on Aug. 26, 2011, provisional application No. 61/528,151, filed on Aug. 27, 2011.

(51) Int. Cl.
| | |
|---|---|
| *A61K 31/498* | (2006.01) |
| *A61K 31/5377* | (2006.01) |
| *A61P 35/00* | (2006.01) |
| *A61P 35/02* | (2006.01) |
| *C07D 401/04* | (2006.01) |
| *C07D 403/04* | (2006.01) |
| *C07D 413/04* | (2006.01) |
| *C07D 241/42* | (2006.01) |
| *C07D 241/44* | (2006.01) |
| *C12Q 1/68* | (2006.01) |
| *A61K 31/18* | (2006.01) |
| *A61K 45/06* | (2006.01) |
| *G01N 33/574* | (2006.01) |

(52) U.S. Cl.
CPC ............ *A61K 31/498* (2013.01); *A61K 31/18* (2013.01); *A61K 31/5377* (2013.01); *A61K 45/06* (2013.01); *C07D 241/42* (2013.01); *C07D 241/44* (2013.01); *C07D 401/04* (2013.01); *C07D 403/04* (2013.01); *C07D 413/04* (2013.01); *C12Q 1/6886* (2013.01); *G01N 33/5748* (2013.01); *C12Q 2600/106* (2013.01); *C12Q 2600/118* (2013.01); *C12Q 2600/156* (2013.01); *G01N 2333/47* (2013.01)

(58) Field of Classification Search
CPC ............ A61K 31/5377; A61K 31/498
See application file for complete search history.

(56) References Cited

U.S. PATENT DOCUMENTS

| | | | |
|---|---|---|---|
| 4,464,533 A | 8/1984 | Krass et al. | |
| 4,761,172 A | 8/1988 | Jahn et al. | |
| 5,033,252 A | 7/1991 | Carter | |
| 5,052,558 A | 10/1991 | Carter | |
| 5,323,907 A | 6/1994 | Kalvelage | |
| 5,846,514 A | 12/1998 | Foster et al. | |
| 6,334,997 B1 | 1/2002 | Foster et al. | |
| 6,348,461 B1 | 2/2002 | Takano et al. | |
| 7,691,866 B2 | 4/2010 | Ramurthy et al. | |
| 8,071,616 B2 | 12/2011 | Dumas et al. | |
| 8,198,273 B2 | 6/2012 | Ibrahim et al. | |
| 9,249,110 B2 | 2/2016 | Qian et al. | |
| 9,249,111 B2 | 2/2016 | Qian et al. | |
| 9,295,671 B2 | 3/2016 | Zhu et al. | |
| 2004/0143117 A1 | 7/2004 | Barnett et al. | |
| 2005/0084835 A1 | 4/2005 | Lau et al. | |
| 2005/0085482 A1 | 4/2005 | Ramurthy et al. | |
| 2007/0232620 A1* | 10/2007 | Dorsch ............... | C07D 231/56 514/255.05 |
| 2008/0167338 A1 | 7/2008 | Spevak et al. | |
| 2008/0207616 A1 | 8/2008 | Aquila et al. | |
| 2009/0105474 A1* | 4/2009 | Yokotani ............... | C07C 229/58 544/166 |
| 2009/0131461 A1 | 5/2009 | Davidson et al. | |
| 2009/0306087 A1 | 12/2009 | Ibrahim et al. | |
| 2009/0317359 A1 | 12/2009 | Ramurthy et al. | |
| 2010/0190777 A1 | 7/2010 | Wu et al. | |
| 2010/0197688 A1 | 8/2010 | Nantermet et al. | |
| 2010/0286142 A1 | 11/2010 | Ibrahim et al. | |
| 2011/0059954 A1 | 3/2011 | Gottschling et al. | |

(Continued)

FOREIGN PATENT DOCUMENTS

| | | | | |
|---|---|---|---|---|
| CN | 101808994 A | 8/2010 | | |
| FR | WO 2012073017 A1 * | 6/2012 | ........... | C07D 403/04 |

(Continued)

OTHER PUBLICATIONS

European search report and opinion dated Mar. 21, 2016 for EP Application No. 13740892.
European search report and opinion dated Apr. 21, 2016 for EP Application No. 13852971.4.
Office action dated Apr. 12, 2016 for U.S. Appl. No. 14/430,890.
Office action dated May 12, 2016 for U.S. Appl. No. 14/344,709.
Zambon, et al. Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
U.S. Appl. No. 15/224,422, filed Jul. 29, 2016, Qian et al.
U.S. Appl. No. 15/226,669, filed Aug. 2, 2016, Qian et al.
Office action dated Aug. 29, 2016 for U.S. Appl. No. 14/430,890.
Notice of allowance dated Oct. 12, 2016 for U.S. Appl. No. 14/344,709.

(Continued)

*Primary Examiner* — Joseph Kosack
*Assistant Examiner* — Amanda L Aguirre
(74) *Attorney, Agent, or Firm* — Wilson Sonsini Goodrich & Rosati

(57) ABSTRACT

Chemical entities that are kinase inhibitors, pharmaceutical compositions and methods of using these chemical entities, e.g., for treatment of cancer are described.

11 Claims, No Drawings

(56) References Cited

U.S. PATENT DOCUMENTS

| | | |
|---|---|---|
| 2011/0172245 A1 | 7/2011 | Hirose et al. |
| 2012/0122860 A1 | 5/2012 | Visor et al. |
| 2012/0245174 A1 | 9/2012 | Ibrahim et al. |
| 2013/0053384 A1 | 2/2013 | Zhu et al. |
| 2013/0237531 A1 | 9/2013 | Wu et al. |
| 2013/0267525 A1 | 10/2013 | Saxty et al. |
| 2014/0038948 A1 | 2/2014 | Wu et al. |
| 2014/0343068 A1 | 11/2014 | Qian et al. |
| 2015/0057276 A1 | 2/2015 | Qian et al. |
| 2015/0057277 A1 | 2/2015 | Zhu et al. |
| 2015/0158826 A1 | 6/2015 | Qian |
| 2015/0246885 A1 | 9/2015 | Qian et al. |
| 2016/0009663 A1 | 1/2016 | Qian et al. |

FOREIGN PATENT DOCUMENTS

| | | | |
|---|---|---|---|
| GB | 2189238 A | 10/1987 | |
| WO | WO-9519169 A2 | 7/1995 | |
| WO | WO 97/22596 A1 | 6/1997 | |
| WO | WO 97/30035 A1 | 8/1997 | |
| WO | WO 97/32856 A1 | 9/1997 | |
| WO | WO 98/13354 A1 | 4/1998 | |
| WO | WO 99/02166 A1 | 1/1999 | |
| WO | WO 00/40529 A1 | 7/2000 | |
| WO | WO 00/41669 A2 | 7/2000 | |
| WO | WO 00/47212 A1 | 8/2000 | |
| WO | WO 00/41669 A3 | 11/2000 | |
| WO | WO 01/92224 A1 | 12/2001 | |
| WO | WO 01/94341 A1 | 12/2001 | |
| WO | WO 02/04434 A1 | 1/2002 | |
| WO | WO 02/08213 A1 | 1/2002 | |
| WO | WO 02/36734 A2 | 5/2002 | |
| WO | WO 2004/056830 A1 | 7/2004 | |
| WO | WO 2005/037285 A1 | 4/2005 | |
| WO | WO 2007/002325 A1 | 1/2007 | |
| WO | WO 2007/044729 A2 | 4/2007 | |
| WO | WO 2009/012283 A1 | 1/2009 | |
| WO | WO 2009012283 A1 * | 1/2009 | ............ C07D 213/75 |
| WO | WO-2009077766 A1 | 6/2009 | |
| WO | WO-2009117080 A1 | 9/2009 | |
| WO | WO 2009/152087 A1 | 12/2009 | |
| WO | WO 2010/075197 A1 | 7/2010 | |
| WO | WO 2010/111527 A1 | 9/2010 | |
| WO | WO 2010/129567 A1 | 11/2010 | |
| WO | WO 2010/129570 A1 | 11/2010 | |
| WO | WO-2011025938 A2 | 3/2011 | |
| WO | WO-2011068187 A1 | 6/2011 | |
| WO | WO 2011/147764 A1 | 12/2011 | |
| WO | WO 2012/073017 A1 | 6/2012 | |
| WO | WO 2012/103810 A1 | 8/2012 | |
| WO | WO 2012/118492 A1 | 9/2012 | |
| WO | WO 2012118492 A1 * | 9/2012 | ............ C07D 239/74 |
| WO | WO 2013/032951 A1 | 3/2013 | |
| WO | WO 2013/040515 A1 | 3/2013 | |
| WO | WO 2013/043935 A1 | 3/2013 | |
| WO | WO 2013/049701 A1 | 4/2013 | |
| WO | WO 2013/112950 A2 | 8/2013 | |

OTHER PUBLICATIONS

U.S. Appl. No. 14/967,124, filed Dec. 11, 2015, Qian et al.
U.S. Appl. No. 14/973,438, filed Dec. 17, 2015, Qian et al.
Ansel, et al. Pharmaceutical Dosage Forms and Drug Delivery Systems. Seventh Edition, Lippincott Williams & Wilkins, 1999.
Bollag, et al. Clinical efficacy of a RAF inhibitor needs broad target bloackade in BRAF-mutant melanoma. Nature. 2010; 467(7315):596-599.
Buchstaller, et al. Design and synthesis of isoquinolines and benzimidazoles as RAF kinase inhibitors. Bioorganic and Medicinal Chemistry Letters. 2011; 21(8):2264-2269.
Choi, et al. New diarylureas and diarylamides containing 1,3,4-triarylpyrazole scaffold: Synthesis, antiproliferative evaluation against melanoma cell lines, ERK kinase inhibition, and molecular docking studies. Eur J Med Chem. Dec. 2011;46(12):5754-62. doi: 10.1016/j.ejmech.2011.08.013. Epub Aug. 12, 2011.
European search report and written opinion dated Jan. 30, 2015 for EP Application No. 12833985.0.
European search report and written opinion dated Feb. 20, 2015 for EP Application No. 12831538.9.
European search report and written opinion dated Dec. 15, 2014 for EP Application No. 12828679.6.
Greene, et al. Protective Groups in Organic Synthesis. John Wiley & Sons, 1991.
Hackam, et al. Translation of research evidence from animals to humans. JAMA. Oct. 11, 2006;296(14):1731-2.
Higuchi, et al. Pro-drugs as novel drug delivery systems. American Chemical Society. ACS symposium series 14. 1975.
Hoover, J. Remington's Pharmaceutical Sciences. Mack Publishing Company, 1990.
International search report and written opinion dated Jan. 23, 2013 for PCT/US2012/058095.
International search report and written opinion dated Feb. 7, 2014 for PCT/US2013/061464.
International search report and written opinion dated Mar. 10, 2014 for PCT/US2013/069699.
International search report and written opinion dated Mar. 22, 2013 for PCT/US2013/023313.
International search report and written opinion dated Oct. 23, 2012 for PCT/US2012/052390.
International search report and written opinion dated Nov. 21, 2012 for PCT/US2012/056432.
International search report and written opinion dated Dec. 10, 2012 for PCT/US2012/055653.
Jordan. Tamoxifen: a most unlikely pioneering medicine. Nat Rev Drug Discov. Mar. 2003;2(3):205-13.
Liberman, et al. Pharmaceutical Dosage Forms. Marcel Decker, New York, 1980.
Lombardo, et al. Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
Notice of allowance dated Sep. 28, 2015 for U.S. Appl. No. 14/346,692.
Notice of allowance dated Nov. 23, 2015 for U.S. Appl. No. 13/594,634.
Office action dated Mar. 27, 2014 for U.S. Appl. No. 13/594,634.
Office action dated Apr. 13, 2015 for U.S. Appl. No. 14/346,692.
Office action dated Apr. 29, 2015 for U.S. Appl. No. 13/594,634.
Office action dated Jun. 11, 2015 for U.S. Appl. No. 14/346,696.
Office action dated Aug. 27, 2015 for U.S. Appl. No. 14/346,692.
Office action dated Sep. 22, 2014 for U.S. Appl. No. 13/594,634.
Office action dated Dec. 5, 2014 for U.S. Appl. No. 14/346,696.
Remington. The Science and Practice of Pharmacy. Mack Publishing Company, 19th Edition, 1995.
Stern, et al. Critical Reviews in Oncology/Haematology, vol. 54, 2005, pp. 11-29.
Tsai, et al. Discovery of a selective inhibitor of oncogenic B-Raf kinase with potent antimelanoma activity. PNAS. 2008; 105(8):3041-3046.
European search report and opinion dated Jan. 29, 2016 for EP Application No. 13838131.
Notice of allowance dated Oct. 23, 2015 for U.S. Appl. No. 14/346,696.
Kraska, et al. Disazo condensation pigments, derivatives of quinoxaline. Polish Journal of Chemistry. 1978; 52(9):1665-74.
Office action dated Jul. 25, 2016 for U.S. Appl. No. 14/374,216.
RN 439126-39-3. Chemical Library File Registry. Entered STN: Jul. 17, 2002.
Notice of Allowance dated Nov. 2, 2016 for U.S. Appl. No. 14/344,709.
Office action dated Oct. 26, 2016 for U.S. Appl. No. 14/442,084.

* cited by examiner

BENZENESULFONAMIDE DERIVATIVES OF QUINOXALINE, PHARMACEUTICAL COMPOSITIONS THEREOF, AND THEIR USE IN METHODS FOR TREATING CANCER

CROSS-REFERENCE

This application is a continuation application of U.S. application Ser. No. 13/594,634, filed Aug. 24, 2012, which claims the benefit of U.S. Provisional Application Ser. No. 61/528,033, filed on Aug. 26, 2011, and 61/528,151, filed on Aug. 27, 2011, which applications are incorporated herein by reference.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

The identification of effective small compounds which specifically inhibit signal transduction and cellular proliferation by modulating the activity of tyrosine and serine/threonine kinases to regulate and modulate abnormal or inappropriate cell proliferation, differentiation, or metabolism is therefore desirable. In particular, the identification of compounds that specifically inhibit the function of a kinase which is essential for processes leading to cancer would be beneficial.

SUMMARY OF THE INVENTION

In one aspect, provided is a compound of Formula I

Formula I

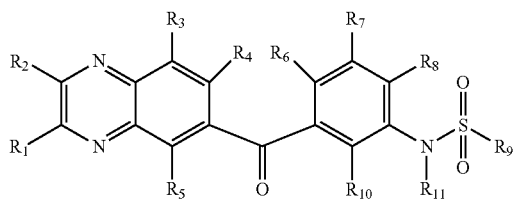

or a pharmaceutically acceptable salt thereof, wherein $R_1$, $R_2$, $R_3$, $R_4$, $R_5$, $R_6$, $R_7$, $R_8$, and $R_{10}$ are independently hydrogen, cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or optionally substituted alkynyl;

$R_9$ is optionally substituted alkyl, optionally substituted cycloalkyl, optionally substituted heterocycloalkyl, optionally substituted aryl, or optionally substituted heteroaryl; and $R_{11}$ is hydrogen, optionally substituted alkyl, optionally substituted cycloalkyl, optionally substituted heterocycloalkyl, optionally substituted aryl, or optionally substituted heteroaryl;

In some embodiments, $R_1$ is hydrogen, cyano, optionally substituted alkoxy, optionally substituted aryloxy, optionally substituted amino, optionally substituted alkyl, optionally substituted aryl, optionally substituted heterocycloalkyl, or optionally substituted heteroaryl. In one embodiment, $R_1$ is optionally substituted aryl, optionally substituted heterocycloalkyl, or optionally substituted heteroaryl. In a further embodiment, $R_1$ is optionally substituted morpholinyl, optionally substituted piperazinyl, optionally substituted imidazolyl, optionally substituted pyrazolyl, or optionally substituted pyridyl.

In some embodiments, $R_2$, $R_3$, $R_4$, and $R_5$ are independently hydrogen, halo, optionally substituted alkoxy, or optionally substituted alkyl. In one embodiment, $R_3$, $R_4$, and $R_5$ are hydrogen.

In some embodiments, $R_6$, $R_7$, $R_8$, and $R_{10}$ are independently hydrogen, cyano, or halo. In one embodiment, each of $R_6$ and $R_{10}$ is independently halo. In a further embodiment, $R_7$ is halo. In yet a further embodiment, $R_8$ is hydrogen. In another embodiment, $R_6$, $R_7$, and $R_{10}$ are fluoro. In a further embodiment, $R_8$ is hydrogen.

In some embodiments, $R_9$ is optionally substituted lower alkyl, optionally substituted aryl, or optionally substituted heteroaryl. In one embodiment, $R_9$ is optionally substituted lower alkyl. In a further embodiment, $R_9$ is optionally substituted propyl.

In some embodiments, $R_{11}$ is hydrogen or optionally substituted lower alkyl. In one embodiment, $R_{11}$ is hydrogen.

In some embodiments, $R_1$ is optionally substituted morpholinyl, optionally substituted piperazinyl, optionally substituted imidazolyl, optionally substituted pyrazolyl, or optionally substituted pyridyl, and each of $R_6$ and $R_{10}$ is independently halo. In one embodiment, $R_7$ is halo. In another embodiment, at least two groups from $R_6$, $R_7$, and $R_{10}$ are fluoro. In a further embodiment, $R_6$, $R_7$, and $R_{10}$ are fluoro.

In some embodiments, each of $R_6$ and $R_{10}$ is independently halo and $R_9$ is optionally substituted lower alkyl. In one embodiment, $R_7$ is halo. In a further embodiment, $R_6$, $R_7$, and $R_{10}$ are fluoro and $R_9$ is optionally substituted lower alkyl.

In some embodiments, $R_1$ is optionally substituted morpholinyl, optionally substituted piperazinyl, optionally substituted imidazolyl, optionally substituted pyrazolyl, or optionally substituted pyridyl, and $R_9$ is optionally substituted lower alkyl.

In some embodiments, $R_1$ is optionally substituted morpholinyl, optionally substituted piperazinyl, optionally substituted imidazolyl, optionally substituted pyrazolyl, or optionally substituted pyridyl, each of $R_6$, $R_7$, and $R_{10}$ is independently halo, and $R_9$ is optionally substituted lower alkyl. In one embodiment, $R_1$ is optionally substituted morpholinyl or optionally substituted piperazinyl, each of $R_6$, $R_7$, and $R_{10}$ is fluoro, and $R_9$ is optionally substituted lower alkyl. In a further embodiment, $R_{11}$ is hydrogen. In yet a further embodiment, $R_8$ is hydrogen.

In another aspect, the present disclosure provides a pharmaceutical composition comprising a pharmaceutically acceptable carrier and a compound or pharmaceutically acceptable salt of any one of compounds described herein. The pharmaceutical composition may be formulated in a form which is a tablet, capsule, powder, liquid, suspension, suppository, or aerosol. The pharmaceutical composition may be packaged with instructions for using the composition to treat a subject suffering from cancer.

In another aspect, the present disclosure provides a method of treating cancer in a subject which comprises administering to a subject in need thereof a therapeutically effective amount of a compound or pharmaceutically acceptable salt of any one of the compounds described herein. The cancer may be colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In a further embodiment, the cancer is melanoma, non-small cell lung cancer, thyroid cancer, ovarian cancer, or colon cancer. The melanoma may be unresectable or metastatic melanoma.

In another aspect, the present disclosure provides a method of treating a disorder mediated by Raf in a subject in need thereof, comprising administering to the subject a therapeutically effective amount of a compound or pharmaceutically acceptable salt of any one of the compounds described herein.

In another aspect, the present disclosure provides method of treating a disorder in a subject in need thereof, comprising: a) determining the presence or absence of a B-Raf (BRAF) mutation in a biological sample isolated from the subject; and b) if a BRAF mutation is determined to be present in the subject, administering to the subject a therapeutically effective amount of a compound or pharmaceutically acceptable salt of any one of the compounds described herein.

The BRAF mutation may be V600E or may be in codon 600. In some embodiments, determining the presence of absence of the BRAF mutation comprises amplifying B-raf nucleic acid from the biological sample and sequencing the amplified nucleic acid. In some other embodiments, determining the presence of absence of the BRAF mutation comprises detecting a mutant B-raf polypeptide in the biological sample using a binding agent to a mutant B-raf polypeptide. The binding agent may be an antibody. The biological sample may be isolated from a tumor of the subject.

In some embodiments, the disorder is cancer. The cancer may be colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In a further embodiment, the cancer is melanoma, non-small cell lung cancer, thyroid cancer, ovarian cancer, or colon cancer. The melanoma may be unresectable or metastatic melanoma.

The treatment method described herein may further comprise administering an additional anti-cancer and/or cytotoxic agent.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION OF THE INVENTION

As used herein, the following words and phrases are generally intended to have the meanings as set forth below, except to the extent that the context in which they are used indicates otherwise.

The following abbreviations and terms have the indicated meanings throughout:
AcOH=acetic acid
Boc=tert-butoxycarbonyl
c-=cyclo
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
i-=iso
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
n-=normal
NaOAc=sodium acetate
PE=petroleum ether
Ph=phenyl
Prep=preparative
quant.=quantitative
RP-HPLC=reverse phase-high pressure liquid chromatography
rt or RT=room temperature
s-=sec-=secondary
t-=tert-=tertiary
THF=tetrahydrofuran
TLC=thin layer chromatography
UV=ultraviolet As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH$_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

As used herein, "formyl" refers to the group —C(O)H.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —$CONR^bR^c$, where $R^b$ is chosen from H, optionally substituted $C_1$-$C_6$ alkyl, optionally substituted cycloalkyl, optionally substituted heterocycloalkyl, optionally substituted aryl, and optionally substituted heteroaryl, optionally substituted alkoxy; and $R^c$ is chosen from hydrogen and optionally substituted $C_1$-$C_4$ alkyl; or $R^b$ and $R^c$ taken together with the nitrogen to which they are bound, form an optionally substituted 4- to 8-membered nitrogen-containing heterocycloalkyl which optionally includes 1 or 2 additional heteroatoms chosen from O, N, and S in the heterocycloalkyl ring;

where each substituted group is independently substituted with one or more substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—NH2.

As used herein, "substituted carbamimidoyl" refers to the group —C(=$NR^e$)—$NR^fR^g$ where $R^e$ is chosen from hydrogen, cyano, optionally substituted alkyl, optionally substituted cycloalkyl, optionally substituted aryl, optionally substituted heteroaryl, and optionally substituted heterocycloalkyl; and $R^f$ and $R^g$ are independently chosen from hydrogen optionally substituted alkyl, optionally substituted cycloalkyl, optionally substituted aryl, optionally substituted heteroaryl, and optionally substituted heterocycloalkyl;

provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —OP(O)($OR^b$)$OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted C1-C6 alkyl, optionally substituted aryl, and optionally substituted heteroaryl;

$R^b$ is chosen from H, optionally substituted C1-C6 alkyl, optionally substituted aryl, and optionally substituted heteroaryl; and $R^c$ is chosen from hydrogen and optionally substituted C1-C4 alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)C$_1$-C$_4$ alkyl, —SO2(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein.

Substituted heteroaryl also includes ring systems substituted with one or more oxide (—O$^-$) substituents, such as pyridinyl N-oxides.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, 2,5-piperazinyl, pyrrolidinyl, azetidinyl, pyranyl, 2,3-dihydrofuranyl, or 2,5-dihydrofuranyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteroatoms independently chosen from oxygen, sulfur, and nitrogen and is not aromatic.

As used herein, "sulfanyl" refers to the groups: —S-(optionally substituted (C$_1$-C$_6$)alkyl), —S-(optionally substituted cycloalkyl), —S-(optionally substituted aryl), —S-(optionally substituted heteroaryl), and —S-(optionally substituted heterocycloalkyl). Hence, sulfanyl includes the group C$_1$-C$_6$ alkylsulfanyl.

As used herein, "sulfinyl" refers to the groups: —S(O)-(optionally substituted (C$_1$-C$_6$)alkyl), —S(O)-(optionally substituted cycloalkyl), —S(O)-(optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S(O$_2$)-(optionally substituted (C$_1$-C$_6$)alkyl), —S(O$_2$)-(optionally substituted cycloalkyl), —S(O$_2$)-(optionally substituted aryl), —S(O$_2$)-(optionally substituted heteroaryl), —S(O$_2$)-(optionally substituted heterocycloalkyl), and —S(O$_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, azido, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted cycloalkyl, optionally substituted heterocycloalkyl, optionally substituted alkenyl, optionally substituted alkynyl, optionally substituted aryl, and optionally substituted heteroaryl; R$^b$ is chosen from hydrogen, optionally substituted C$_1$-C$_6$ alkyl, optionally substituted cycloalkyl, optionally substituted heterocycloalkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO₂NH(phenyl), —NHSO₂(C₁-C₄ alkyl), —NHSO₂(phenyl), and —NHSO₂(C₁-C₄ haloalkyl).

In some embodiments, a substituted alkoxy group is "polyalkoxy" or —O-(optionally substituted alkylene)-(optionally substituted alkoxy), and includes groups such as —OCH₂CH₂OCH₃, and residues of glycol ethers such as polyethyleneglycol, and —O(CH₂CH₂O)ₓCH₃, where x is an integer of 2-20, such as 2-10, and for example, 2-5. Another substituted alkoxy group is hydroxyalkyl or —OCH₂(CH₂)ᵧOH, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from —Rᵃ, —ORᵇ, optionally substituted amino (including —NRᶜCORᵇ, —NRᶜCO₂Rᵃ, —NRᶜCONRᵇRᶜ, —NRᵇC(NRᶜ)NRᵇRᶜ, —NRᵇC(NCN)NRᵇRᶜ, and —NRᶜSO₂Rᵃ), halo, cyano, nitro, oxo (as a substituent for cycloalkyl or heterocycloalkyl), optionally substituted acyl (such as —CORᵇ), optionally substituted alkoxycarbonyl (such as —CO₂Rᵇ), aminocarbonyl (such as —CONRᵇRᶜ), —OCORᵇ, —OCO₂Rᵃ, —OCONRᵇRᶜ, —OP(O)(ORᵇ) ORᶜ, sulfanyl (such as SRᵇ), sulfinyl (such as —SORᵃ), and sulfonyl (such as —SO₂Rᵃ and —SO₂NRᵇRᶜ), where Rᵃ is chosen from optionally substituted C₁-C₆ alkyl, optionally substituted alkenyl, optionally substituted alkynyl, optionally substituted aryl, and optionally substituted heteroaryl;

Rᵇ is chosen from H, optionally substituted C₁-C₆ alkyl, optionally substituted cycloalkyl, optionally substituted heterocycloalkyl, optionally substituted aryl, and optionally substituted heteroaryl; and Rᶜ is chosen from hydrogen and optionally substituted C₁-C₄ alkyl; or Rᵇ and Rᶜ, and the nitrogen to which they are attached, form an optionally substituted heterocycloalkyl group; and where each optionally substituted group is unsubstituted or independently substituted with one or more, such as one, two, or three, substituents independently chosen from C₁-C₄ alkyl, aryl, heteroaryl, aryl-C₁-C₄ alkyl-, heteroaryl-C₁-C₄ alkyl-, C₁-C₄ haloalkyl, —OC₁-C₄ alkyl, —OC₁-C₄ alkyl-phenyl, —C₁-C₄ alkyl-OH, —OC₁-C₄ haloalkyl, halo, —OH, —NH₂, —C₁-C₄ alkyl-NH₂, —N(C₁-C₄ alkyl)(C₁-C₄ alkyl), —NH(C₁-C₄ alkyl), —N(C₁-C₄ alkyl)(C₁-C₄ alkylphenyl), —NH(C₁-C₄ alkylphenyl), cyano, nitro, oxo (as a substituent for cycloalkyl or heterocycloalkyl), —CO₂H, —C(O)OC₁-C₄ alkyl, —CON(C₁-C₄ alkyl)(C₁-C₄ alkyl), —CONH(C₁-C₄ alkyl), —CONH₂, —NHC(O)(C₁-C₄ alkyl), —NHC(O)(phenyl), —N(C₁-C₄ alkyl)C(O)(C₁-C₄ alkyl), —N(C₁-C₄ alkyl)C(O)(phenyl), —C(O)C₁-C₄ alkyl, —C(O)C₁-C₄ alkylphenyl, —C(O)C₁-C₄ haloalkyl, —OC(O)C₁-C₄ alkyl, —SO₂(C₁-C₄ alkyl), —SO₂(phenyl), —SO₂(C₁-C₄ haloalkyl), —SO₂NH₂, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl).

As used herein, "substituted amino" refers to the group —NHRᵈ or —NRᵈRe wherein Rᵈ is chosen from hydroxyl, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein Rᵉ is chosen from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —Rᵃ, —ORᵇ, optionally substituted amino (including —NRᶜCORᵇ, —NRᶜCO₂Rᵃ, —NRᶜCONRᵇRᶜ, —NRᵇC(NRᶜ)NRᵇRᶜ, —NRᵇC(NCN)NRᵇRᶜ, and —NRᶜSO₂Rᵃ), halo, cyano, nitro, oxo (as a substituent for cycloalkyl or heterocycloalkyl), optionally substituted acyl (such as —CORᵇ), optionally substituted alkoxycarbonyl (such as —CO₂Rᵇ), aminocarbonyl (such as —CONRᵇRᶜ), —OCORᵇ, —OCO₂Rᵃ, —OCONRᵇRᶜ, —OP(O)(ORᵇ) ORᶜ, sulfanyl (such as SRᵇ), sulfinyl (such as —SORᵃ), and sulfonyl (such as —SO₂Rᵃ and —SO₂NRᵇRᶜ), where Rᵃ is chosen from optionally substituted C₁-C₆ alkyl, optionally substituted alkenyl, optionally substituted alkynyl, optionally substituted aryl, and optionally substituted heteroaryl;

Rᵇ is chosen from H, optionally substituted C₁-C₆ alkyl, optionally substituted cycloalkyl, optionally substituted heterocycloalkyl, optionally substituted aryl, and optionally substituted heteroaryl; and Rᶜ is chosen from hydrogen and optionally substituted C₁-C₄ alkyl; or Rᵇ and Rᶜ, and the nitrogen to which they are attached, form an optionally substituted heterocycloalkyl group; and where each optionally substituted group is unsubstituted or independently substituted with one or more, such as one, two, or three, substituents independently chosen from C₁-C₄ alkyl, aryl, heteroaryl, aryl-C₁-C₄ alkyl-, heteroaryl-C₁-C₄ alkyl-, C₁-C₄ haloalkyl, —OC₁-C₄ alkyl, —OC₁-C₄ alkyl-phenyl, —C₁-C₄ alkyl-OH, —OC₁-C₄ haloalkyl, halo, —OH, —NH₂, —C₁-C₄ alkyl-NH₂, —N(C₁-C₄ alkyl)(C₁-C₄ alkyl), —NH(C₁-C₄ alkyl), —N(C₁-C₄ alkyl)(C₁-C₄ alkylphenyl), —NH(C₁-C₄ alkylphenyl), cyano, nitro, oxo (as a substituent for cycloalkyl or heterocycloalkyl), —CO₂H, —C(O)OC₁-C₄ alkyl, —CON(C₁-C₄ alkyl)(C₁-C₄ alkyl), —CONH(C₁-C₄ alkyl), —CONH₂, —NHC(O)(C₁-C₄ alkyl), —NHC(O)(phenyl), —N(C₁-C₄ alkyl)C(O)(C₁-C₄ alkyl), —N(C₁-C₄ alkyl)C(O)(phenyl), —C(O)C₁-C₄ alkyl, —C(O)C₁-C₄ alkylphenyl, —C(O)C₁-C₄ haloalkyl, —OC(O)C₁-C₄ alkyl, —SO₂(C₁-C₄ alkyl), —SO₂(phenyl), —SO₂(C₁-C₄ haloalkyl), —SO₂NH₂, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl); and wherein optionally substituted acyl, optionally substituted alkoxycarbonyl, sulfinyl and sulfonyl are as defined herein.

The term "substituted amino" also refers to N-oxides of the groups —NHRᵈ, and NRᵈRd each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable forms" of compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, pharmaceutically acceptable salts include "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen. group containing a ring nitrogen or a heteroaryl group containing a ring nitrogen.

The compounds disclosed herein can be used in different enriched isotopic forms, e.g., enriched in the content of $^2H$, $^3H$, $^{11}C$, $^{13}C$ and/or $^{14}C$. In one particular embodiment, the compound is deuterated at at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein, the terms "group", "radical" or "fragment" are synonymous and are intended to indicate functional groups or fragments of molecules attachable to a bond or other fragments of molecules.

As used herein, the term "leaving group" refers to the meaning conventionally associated with it in synthetic organic chemistry, i.e., an atom or group displaceable under nucleophilic displacement conditions. Examples of leaving groups include, but are not limited to, dimethylhydroxylamino (e.g. Weinreb amide), halogen, alkane- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

As used herein, the term "protective group" or "protecting group" refers to a group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block certain reactive sites present in the reactants. Examples of protecting groups can be found in Wuts et al., *Green's Protective Groups in Organic Synthesis*, (J. Wiley, 4th ed. 2006).

As used herein, the term "deprotection" or "deprotecting" refers to a process by which a protective group is removed after a selective reaction is completed. Certain protective groups may be preferred over others due to their convenience or relative ease of removal. Without being limiting, deprotecting reagents for protected amino or anilino group include strong acid such as trifluoroacetic acid (TFA), concentrated HCl, $H_2SO_4$, or HBr, and the like.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anti-cancer therapeutic.

As used herein, "significant" refers to any detectable change that is statistically significant in a standard parametric test of statistical significance such as Student's T-test, where $p<0.05$.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

As used herein, the terms "BRAF", "B-raf", "B-Raf" and the like are used interchangeably to refer to the gene or protein product of the gene.

A. Compounds

In one aspect, provided herein is a compound of Formula I

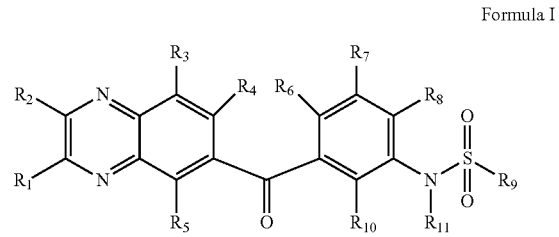

Formula I or a pharmaceutically acceptable salt thereof, wherein
$R_1$, $R_2$, $R_3$, $R_4$, $R_5$, $R_6$, $R_7$, $R_8$, and $R_{10}$ are independently hydrogen, cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or optionally substituted alkynyl;

$R_9$ is optionally substituted alkyl, optionally substituted cycloalkyl, optionally substituted heterocycloalkyl, optionally substituted aryl, or optionally substituted heteroaryl; and $R_{11}$ is hydrogen, optionally substituted alkyl, optionally substituted cycloalkyl, optionally substituted heterocycloalkyl, optionally substituted aryl, or optionally substituted heteroaryl.

In some embodiments, when $R_{10}$ is fluoro, then $R_7$ is not hydrogen, or $R_8$ is not hydrogen, or $R_6$ is not hydrogen, lower alkyl or halo.

In some embodiments, $R_1$ is hydrogen, cyano, halo, hydroxy, carboxy, optionally substituted alkoxy, optionally substituted aryloxy, optionally substituted alkoxycarbonyl, optionally substituted alkyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or optionally substituted alkynyl. In a further embodiment, $R_1$ is hydrogen, cyano, optionally substituted alkoxy, optionally substituted aryloxy, optionally substituted amino, optionally substituted alkyl, optionally substituted aryl, optionally substituted heterocycloalkyl, or optionally substituted heteroaryl. In another further embodiment, $R_1$ is optionally substituted aryl, optionally substituted heterocycloalkyl, or optionally substituted heteroaryl. In yet another embodiment, $R_1$ is optionally substituted morpholinyl, optionally substituted piperazinyl, optionally substituted imidazolyl, optionally substituted pyrazolyl, or optionally substituted pyridyl. In other embodiments, $R_1$ is chosen from hydrogen, cyano, lower alkyl, lower alkoxy, amino, 1H-imidazol-1-yl optionally substituted with lower alkyl, 1H-pyrazol-4-yl optionally substituted with lower alkyl, 1H-pyrazol-3-yl optionally substituted with lower alkyl, pyridin-2-yl optionally substituted with lower alkyl, pyridin-3-yl optionally substituted with lower alkyl, and pyridin-4-yl optionally substituted with lower alkyl. In some embodiments, $R_1$ is chosen from hydrogen, methyl, cyano, methoxy, 1H-imidazol-1-yl, 2-methyl-1H-imidazol-1-yl, 5-methyl-1H-imidazol-1-yl, 4-methyl-1H-imidazol-1-yl, 1H-pyrazol-4-yl, 1H-pyrazol-3-yl, pyridin-3-yl, 6-methylpyridin-3-yl, pyridin-4-yl, morpholinyl, and piperazinyl. In other embodiments, $R_1$ is optionally substituted heteroaryl. For example, $R_1$ is 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, or 5,6,7,8-tetrahydroisoquinolinyl. In yet other embodiments, $R_1$ is optionally substituted heterocycloalkyl. For example, $R_1$ is pyrrolidinyl such as 2-pyrrolidinyl, imidazolidinyl such as 2,4-imidazolidinyl, pyrazolidinyl such as 2,3-pyrazolidinyl, piperidyl such as 2-piperidyl, 3-piperidyl, or 4-piperidyl, piperazinyl such as 2,5-piperazinyl, pyrrolidinyl, azetidinyl, pyranyl, dihydrofuranyl such as 2,3-dihydrofuranyl, or 2,5-dihydrofuranyl, morpholinyl such as 2-morpholinyl or 3-morpholinyl, piperidinyl N-oxide, morpholinyl-N-oxide, 1-oxo-1-thiomorpholinyl or 1,1-dioxo-1-thiomorpholinyl.

In some embodiments, each of $R_2$, $R_3$, $R_4$, and $R_5$ is independently hydrogen, halo, optionally substituted alkoxy, or optionally substituted alkyl. In some embodiments, $R_2$ is chosen from hydrogen, halo, alkoxy, and alkyl. In some embodiments, $R_2$ is hydrogen.

In some embodiments, $R_3$ is hydrogen, halo, alkoxy, or alkyl. In some embodiments, $R_3$ is hydrogen. In some embodiments, $R_4$ is hydrogen, halo, alkoxy, or alkyl. In some embodiments, $R_4$ is hydrogen. In some embodiments, $R_5$ is hydrogen, halo, alkoxy, or alkyl. In some embodiments, $R_5$ is hydrogen.

In some embodiments, $R_2$, $R_3$, $R_4$, and $R_5$ are hydrogen.

In some embodiments, each of $R_6$, $R_7$, $R_8$, and $R_{10}$ is independently hydrogen, cyano, halo, optionally substituted alkoxy, optionally substituted alkyl, optionally substituted acyl, optionally substituted alkoxycarbonyl, optionally substituted aminocarbonyl, or optionally substituted aminosulfonyl. In a further embodiment, each of $R_6$, $R_7$, $R_8$, and $R_{10}$ is independently hydrogen, cyano, or halo. In another embodiment, $R_7$ is halo. In yet another embodiment, $R_7$ is fluoro. In a further embodiment, $R_7$ and $R_8$ are hydrogen.

In some embodiments, $R_6$ is hydrogen, cyano, or halo. In some embodiments, $R_6$ is halo. In some embodiments, $R_6$ is fluoro. In some embodiments, $R_8$ is hydrogen, cyano, or halo. In some embodiments, $R_8$ is hydrogen. In some embodiments, $R_{10}$ is hydrogen, cyano, or halo. In some embodiments, $R_{10}$ is hydrogen, fluoro or chloro. In some embodiments, $R_7$ is hydrogen, cyano, or halo. In some embodiments, $R_7$ is hydrogen or halo. In some embodiments, $R_7$ is hydrogen or fluoro. In some embodiments, $R_7$ is halo. In some embodiments, $R_7$ is fluoro.

In some embodiments, $R_6$ and $R_7$ are fluoro. For example, $R_6$ and $R_7$ are fluoro and $R_{10}$ is hydrogen. In other embodiments, $R_6$, $R_7$ and $R_{10}$ are fluoro. In some embodiments, $R_6$ is fluoro and $R_{10}$ is chloro. For example, $R_6$ is fluoro, $R_{10}$ is chloro and $R_7$ is hydrogen.

In some embodiments, $R_9$ is optionally substituted alkyl, optionally substituted cycloalkyl, optionally substituted aryl, or optionally substituted heteroaryl. In one embodiment, $R_9$ is optionally substituted lower alkyl, optionally substituted aryl, or optionally substituted heteroaryl. In some embodiments, $R_9$ is lower alkyl or aryl, said lower alkyl or aryl being optionally substituted with one or two groups independently chosen from halo, cyano, optionally substituted lower alkyl, optionally substituted amino, and optionally substituted lower alkoxy, and heteroaryl. In a further embodiment, $R_9$ is optionally substituted lower alkyl.

In some embodiments, $R_{11}$ is hydrogen, optionally substituted lower alkyl, optionally substituted aryl, or optionally substituted heteroaryl. In a further embodiment, $R_{11}$ is hydrogen or optionally substituted lower alkyl. In another further embodiment, $R_{11}$ is hydrogen. In some embodiments, $R_{11}$ is optionally substituted lower alkyl.

In some embodiments, $R_6$, $R_7$, $R_8$, and $R_{10}$ are independently hydrogen, cyano, or halo. In one embodiment, each of $R_6$ and $R_{10}$ is independently halo. In a further embodiment, $R_7$ is halo. In yet a further embodiment, $R_8$ is hydrogen. In another embodiment, $R_6$, $R_7$, and $R_{10}$ are fluoro. In a further embodiment, $R_8$ is hydrogen.

In some embodiments, $R_1$ is optionally substituted morpholinyl, optionally substituted piperazinyl, optionally substituted imidazolyl, optionally substituted pyrazolyl, or optionally substituted pyridyl, and each of $R_6$ and $R_{10}$ is independently halo. In one embodiment, $R_7$ is halo. In another embodiment, at least two groups from $R_6$, $R_7$, and $R_{10}$ are fluoro. In a further embodiment, $R_6$, $R_7$, and $R_{10}$ are fluoro.

In some embodiments, each of $R_6$ and $R_{10}$ is independently halo and $R_9$ is optionally substituted lower alkyl. In one embodiment, $R_7$ is halo. In a further embodiment, $R_6$, $R_7$, and $R_{10}$ are fluoro and $R_9$ is optionally substituted lower alkyl.

In some embodiments, $R_1$ is optionally substituted morpholinyl, optionally substituted piperazinyl, optionally substituted imidazolyl, optionally substituted pyrazolyl, or optionally substituted pyridyl, and $R_9$ is optionally substituted lower alkyl.

In some embodiments, $R_1$ is optionally substituted morpholinyl, optionally substituted piperazinyl, optionally substituted imidazolyl, optionally substituted pyrazolyl, or optionally substituted pyridyl, each of $R_6$, $R_7$, and $R_{10}$ is independently halo, and $R_9$ is optionally substituted lower alkyl. In one embodiment, $R_1$ is optionally substituted morpholinyl, optionally substituted pyrazolyl, or optionally substituted piperazinyl, each of $R_6$, $R_7$, and $R_{10}$ is fluoro, and $R_9$ is optionally substituted lower alkyl. In a further embodiment, $R_{11}$ is hydrogen. In yet a further embodiment, $R_8$ is hydrogen.

In another aspect, the present disclosure provides a compound or pharmaceutically acceptable salt chosen from the group consisting of:

- N-(3,4-difluoro-5-(quinoxaline-6-carbonyl)phenyl)propane-1-sulfonamide,
- N-(3,4-difluoro-5-(3-methylquinoxaline-6-carbonyl)phenyl)propane-1-sulfonamide,
- N-(3-(3-cyanoquinoxaline-6-carbonyl)-4,5-difluorophenyl)propane-1-sulfonamide,
- N-(3,4-difluoro-5-(3-methoxyquinoxaline-6-carbonyl)phenyl)propane-1-sulfonamide,
- N-(3,4-difluoro-5-(3-phenylquinoxaline-6-carbonyl)phenyl)propane-1-sulfonamide,
- N-(3-(3-(4-chlorophenyl)quinoxaline-6-carbonyl)-4,5-difluorophenyl)propane-1-sulfonamide,
- N-(3,4-difluoro-5-(3-(4-fluorophenyl)quinoxaline-6-carbonyl)phenyl)propane-1-sulfonamide,
- N-(3-(3-(1H-imidazol-1-yl)quinoxaline-6-carbonyl)-4,5-difluorophenyl)propane-1-sulfonamide,
- N-(3,4-difluoro-5-(3-(2-methyl-1H-imidazol-1-yl)quinoxaline-6-carbonyl)phenyl)propane-1-sulfonamide,
- N-(3,4-difluoro-5-(3-(5-methyl-1H-imidazol-1-yl)quinoxaline-6-carbonyl)phenyl)propane-1-sulfonamide,
- N-(3,4-difluoro-5-(3-(4-methyl-1H-imidazol-1-yl)quinoxaline-6-carbonyl)phenyl)propane-1-sulfonamide,
- N-(3,4-difluoro-5-(3-(pyridin-3-yl)quinoxaline-6-carbonyl)phenyl)propane-1-sulfonamide,
- N-(3,4-difluoro-5-(3-(6-methylpyridin-3-yl)quinoxaline-6-carbonyl)phenyl)propane-1-sulfonamide,
- N-(3,4-difluoro-5-(3-(pyridin-4-yl)quinoxaline-6-carbonyl)phenyl)propane-1-sulfonamide,
- N-(2,4,5-trifluoro-3-(quinoxaline-6-carbonyl)phenyl)propane-1-sulfonamide,
- N-(2,4,5-trifluoro-3-(3-methylquinoxaline-6-carbonyl)phenyl)propane-1-sulfonamide,
- N-(3-(3-cyanoquinoxaline-6-carbonyl)-2,4,5-trifluorophenyl)propane-1-sulfonamide,
- N-(2,4,5-trifluoro-3-(3-methoxyquinoxaline-6-carbonyl)phenyl)propane-1-sulfonamide,
- N-(2,4,5-trifluoro-3-(3-phenylquinoxaline-6-carbonyl)phenyl)propane-1-sulfonamide,
- N-(3-(3-(4-chlorophenyl)quinoxaline-6-carbonyl)-2,4,5-trifluorophenyl)propane-1-sulfonamide,
- N-(2,4,5-trifluoro-3-(3-(4-fluorophenyl)quinoxaline-6-carbonyl)phenyl)propane-1-sulfonamide,
- N-(3-(3-(1H-imidazol-1-yl)quinoxaline-6-carbonyl)-2,4,5-trifluorophenyl)propane-1-sulfonamide,
- N-(2,4,5-trifluoro-3-(3-(2-methyl-1H-imidazol-1-yl)quinoxaline-6-carbonyl)phenyl)propane-1-sulfonamide,
- N-(2,4,5-trifluoro-3-(3-(5-methyl-1H-imidazol-1-yl)quinoxaline-6-carbonyl)phenyl)propane-1-sulfonamide,
- N-(2,4,5-trifluoro-3-(3-(4-methyl-1H-imidazol-1-yl)quinoxaline-6-carbonyl)phenyl)propane-1-sulfonamide,
- N-(2,4,5-trifluoro-3-(3-(pyridin-3-yl)quinoxaline-6-carbonyl)phenyl)propane-1-sulfonamide,
- N-(2,4,5-trifluoro-3-(3-(6-methylpyridin-3-yl)quinoxaline-6-carbonyl)phenyl)propane-1-sulfonamide,
- N-(2,4,5-trifluoro-3-(3-(pyridin-4-yl)quinoxaline-6-carbonyl)phenyl)propane-1-sulfonamide,
- N-(2-chloro-4-fluoro-3-(quinoxaline-6-carbonyl)phenyl)propane-1-sulfonamide,
- N-(2-chloro-4-fluoro-3-(3-methylquinoxaline-6-carbonyl)phenyl)propane-1-sulfonamide,
- N-(2-chloro-3-(3-cyanoquinoxaline-6-carbonyl)-4-fluorophenyl)propane-1-sulfonamide,
- N-(2-chloro-4-fluoro-3-(3-methoxyquinoxaline-6-carbonyl)phenyl)propane-1-sulfonamide,
- N-(2-chloro-4-fluoro-3-(3-phenylquinoxaline-6-carbonyl)phenyl)propane-1-sulfonamide,
- N-(2-chloro-3-(3-(4-chlorophenyl)quinoxaline-6-carbonyl)-4-fluorophenyl)propane-1-sulfonamide,
- N-(2-chloro-4-fluoro-3-(3-(4-fluorophenyl)quinoxaline-6-carbonyl)phenyl)propane-1-sulfonamide,
- N-(3-(3-(1H-imidazol-1-yl)quinoxaline-6-carbonyl)-2-chloro-4-fluorophenyl)propane-1-sulfonamide,
- N-(2-chloro-4-fluoro-3-(3-(2-methyl-1H-imidazol-1-yl)quinoxaline-6-carbonyl)phenyl)propane-1-sulfonamide,
- N-(2-chloro-4-fluoro-3-(3-(5-methyl-1H-imidazol-1-yl)quinoxaline-6-carbonyl)phenyl)propane-1-sulfonamide,
- N-(2-chloro-4,5-difluoro-3-(quinoxaline-6-carbonyl)phenyl)propane-1-sulfonamide,
- N-(2-chloro-4,5-difluoro-3-(3-methylquinoxaline-6-carbonyl)phenyl)propane-1-sulfonamide,
- N-(2-chloro-3-(3-cyanoquinoxaline-6-carbonyl)-4,5-difluorophenyl)propane-1-sulfonamide,
- N-(2-chloro-4,5-difluoro-3-(3-methoxyquinoxaline-6-carbonyl)phenyl)propane-1-sulfonamide,
- N-(2-chloro-4,5-difluoro-3-(3-(methylamino)quinoxaline-6-carbonyl)phenyl)propane-1-sulfonamide,
- N-(3-(3-aminoquinoxaline-6-carbonyl)-2-chloro-4,5-difluorophenyl)propane-1-sulfonamide,
- N-(2-chloro-4,5-difluoro-3-(3-phenylquinoxaline-6-carbonyl)phenyl)propane-1-sulfonamide,
- N-(2-chloro-3-(3-(4-chlorophenyl)quinoxaline-6-carbonyl)-4,5-difluorophenyl)propane-1-sulfonamide,
- N-(2-chloro-4,5-difluoro-3-(3-(4-fluorophenyl)quinoxaline-6-carbonyl)phenyl)propane-1-sulfonamide,
- N-(3-(3-(1H-imidazol-1-yl)quinoxaline-6-carbonyl)-2-chloro-4,5-difluorophenyl)propane-1-sulfonamide,
- N-(2-chloro-4,5-difluoro-3-(3-(2-methyl-1H-imidazol-1-yl)quinoxaline-6-carbonyl)phenyl)propane-1-sulfonamide,
- N-(2-chloro-4,5-difluoro-3-(3-(5-methyl-1H-imidazol-1-yl)quinoxaline-6-carbonyl)phenyl)propane-1-sulfonamide,
- N-(2-chloro-4,5-difluoro-3-(3-(4-methyl-1H-imidazol-1-yl)quinoxaline-6-carbonyl)phenyl)propane-1-sulfonamide,
- N-(2-chloro-4,5-difluoro-3-(3-(pyridin-3-yl)quinoxaline-6-carbonyl)phenyl)propane-1-sulfonamide,
- N-(2-chloro-4,5-difluoro-3-(3-(6-methylpyridin-3-yl)quinoxaline-6-carbonyl)phenyl)propane-1-sulfonamide,
- N-(2-chloro-4,5-difluoro-3-(3-(pyridin-4-yl)quinoxaline-6-carbonyl)phenyl)propane-1-sulfonamide,
- N-(2-chloro-4,5-difluoro-3-(3-morpholinoquinoxaline-6-carbonyl)phenyl)propane-1-sulfonamide, N-(2-chloro-4,5-difluoro-3-(3-(piperazin-1-yl)quinoxa-line-6-carbonyl)phenyl)propane-1-sulfonamide,
N-(3-(3-((2-aminoethyl)amino)quinoxaline-6-carbonyl)-2-chloro-4,5-difluorophenyl)propane-1-sulfonamide,
N-(2-chloro-4,5-difluoro-3-(3-((2-hydroxyethyl)amino) quinoxaline-6-carbonyl)phenyl)propane-1-sulfonamide,
N-(2-chloro-4,5-difluoro-3-(3-((2-methoxyethyl)amino) quinoxaline-6-carbonyl)phenyl)propane-1-sulfonamide,
N-(2-chloro-4,5-difluoro-3-(3-(2-methoxyethoxy)qui-noxaline-6-carbonyl)phenyl)propane-1-sulfonamide,
N-(2-chloro-4,5-difluoro-3-(3-(2-hydroxyethoxy)qui-noxaline-6-carbonyl)phenyl)propane-1-sulfonamide,
N-(3-(3-(1H-pyrazol-4-yl)quinoxaline-6-carbonyl)-2-chloro-4,5-difluorophenyl)propane-1-sulfonamide,
N-(3-(3-(1H-pyrazol-3-yl)quinoxaline-6-carbonyl)-2-chloro-4,5-difluorophenyl)propane-1-sulfonamide,
N-(3-(3-(1H-pyrazol-3-yl)quinoxaline-6-carbonyl)-2,4,5-trifluorophenyl)propane-1-sulfonamide,
N-(3-(3-aminoquinoxaline-6-carbonyl)-2,4,5-trifluoro-phenyl)propane-1-sulfonamide,
N-(2,4,5-trifluoro-3-(3-(methylamino)quinoxaline-6-car-bonyl)phenyl)propane-1-sulfonamide,
N-(2,4,5-trifluoro-3-(3-(2-hydroxyethoxy)quinoxaline-6-carbonyl)phenyl)propane-1-sulfonamide,
N-(2,4,5-trifluoro-3-(3-(2-methoxyethoxy)quinoxaline-6-carbonyl)phenyl)propane-1-sulfonamide,
N-(2,4,5-trifluoro-3-(3-((2-methoxyethyl)amino)qui-noxaline-6-carbonyl)phenyl)propane-1-sulfonamide,
N-(3-(3-((2-aminoethyl)amino)quinoxaline-6-carbonyl)-2,4,5-trifluorophenyl)propane-1-sulfonamide, and
N-(2,4,5-trifluoro-3-(3-((2-hydroxyethyl)amino)quinoxa-line-6-carbonyl)phenyl)propane-1-sulfonamide,
N-(2-chloro-4-fluoro-3-(3-(4-methyl-1H-imidazol-1-yl) quinoxaline-6-carbonyl)phenyl)propane-1-sulfona-mide,
N-(2-chloro-4-fluoro-3-(3-(pyridin-3-yl)quinoxaline-6-carbonyl)phenyl)propane-1-sulfonamide,
N-(2-chloro-4-fluoro-3-(3-(6-methylpyridin-3-yl)qui-noxaline-6-carbonyl)phenyl)propane-1-sulfonamide,
N-(2-chloro-4-fluoro-3-(3-(pyridin-4-yl)quinoxaline-6-carbonyl)phenyl)propane-1-sulfonamide,
N-(3,4-difluoro-5-(quinoxaline-6-carbonyl)phenyl)ben-zenesulfonamide,
N-(3,4-difluoro-5-(3-methylquinoxaline-6-carbonyl)phe-nyl)benzenesulfonamide,
N-(3-(3-cyanoquinoxaline-6-carbonyl)-4,5-difluorophe-nyl)benzenesulfonamide,
N-(3,4-difluoro-5-(3-methoxyquinoxaline-6-carbonyl) phenyl)benzenesulfonamide,
N-(3,4-difluoro-5-(quinoxaline-6-carbonyl)phenyl)-3-fluorobenzenesulfonamide,
N-(3,4-difluoro-5-(3-methylquinoxaline-6-carbonyl)phe-nyl)-3-fluorobenzenesulfonamide,
N-(3-(3-cyanoquinoxaline-6-carbonyl)-4,5-difluorophe-nyl)-3-fluorobenzenesulfonamide,
N-(3,4-difluoro-5-(3-methoxyquinoxaline-6-carbonyl) phenyl)-3-fluorobenzenesulfonamide,
N-(2,4,5-trifluoro-3-(quinoxaline-6-carbonyl)phenyl) benzenesulfonamide,
N-(2,4,5-trifluoro-3-(3-methylquinoxaline-6-carbonyl) phenyl)benzene sulfonamide,
N-(3-(3-cyanoquinoxaline-6-carbonyl)-2,4,5-trifluoro-phenyl)benzenesulfonamide,
N-(2,4,5-trifluoro-3-(3-methoxyquinoxaline-6-carbonyl) phenyl)benzene sulfonamide,
3-fluoro-N-(2,4,5-trifluoro-3-(quinoxaline-6-carbonyl) phenyl)benzenesulfonamide,
3-fluoro-N-(2,4,5-trifluoro-3-(3-methylquinoxaline-6-carbonyl)phenyl)benzenesulfonamide,
N-(3-(3-cyanoquinoxaline-6-carbonyl)-2,4,5-trifluoro-phenyl)-3-fluorobenzenesulfonamide,
3-fluoro-N-(2,4,5-trifluoro-3-(3-methoxyquinoxaline-6-carbonyl)phenyl)benzenesulfonamide,
N-(2-chloro-4-fluoro-3-(quinoxaline-6-carbonyl)phenyl) benzenesulfonamide,
N-(2-chloro-4-fluoro-3-(3-methylquinoxaline-6-carbo-nyl)phenyl)benzene sulfonamide,
N-(2-chloro-3-(3-cyanoquinoxaline-6-carbonyl)-4-fluo-rophenyl)benzenesulfonamide,
N-(2-chloro-4-fluoro-3-(3-methoxyquinoxaline-6-carbo-nyl)phenyl)benzenesulfonamide,
N-(2-chloro-4-fluoro-3-(quinoxaline-6-carbonyl)phenyl)-3-fluorobenzenesulfonamide,
N-(2-chloro-4-fluoro-3-(3-methylquinoxaline-6-carbo-nyl)phenyl)-3-fluorobenzenesulfonamide,
N-(2-chloro-3-(3-cyanoquinoxaline-6-carbonyl)-4-fluo-rophenyl)-3-fluorobenzenesulfonamide,
N-(2-chloro-4-fluoro-3-(3-methoxyquinoxaline-6-carbo-nyl)phenyl)-3-fluorobenzenesulfonamide,
N-(2-chloro-4,5-difluoro-3-(quinoxaline-6-carbonyl)phe-nyl)propane-1-sulfonamide,
N-(4-fluoro-3-(quinoxaline-6-carbonyl)phenyl)propane-1-sulfonamide,
N-(3-fluoro-5-(quinoxaline-6-carbonyl)phenyl)propane-1-sulfonamide,
N-(4-fluoro-3-(3-morpholinoquinoxaline-6-carbonyl) phenyl)propane-1-sulfonamide,
N-(2,4,5-trifluoro-3-(3-(2-methoxyethoxy)quinoxaline-6-carbonyl)phenyl)propane-1-sulfonamide,
N-(2,4,5-trifluoro-3-(3-(piperazin-1-yl)quinoxaline-6-carbonyl)phenyl)propane-1-sulfonamide,
N-(2,4,5-trifluoro-3-(3-(2-oxopiperazin-1-yl)quinoxa-line-6-carbonyl)phenyl)propane-1-sulfonamide,
N-(3-(3-(1H-pyrazol-4-yl)quinoxaline-6-carbonyl)-2,4,5-trifluorophenyl)propane-1-sulfonamide,
N-(2,4,5-trifluoro-3-(3-morpholinoquinoxaline-6-carbo-nyl)cyclopropanesulfonamide,
N-(2,4,5-trifluoro-3-(3-(3-oxopiperazin-1-yl)quinoxa-line-6-carbonyl)phenyl)propane-1-sulfonamide,
N-(3-(3-(diethylamino)quinoxaline-6-carbonyl)-2,4,5-tri-fluorophenyl)propane-1-sulfonamide,
N-(2,4,5-trifluoro-3-(3-fluoroquinoxaline-6-carbonyl) phenyl)propane-1-sulfonamide,
N-(2,4-difluoro-3-(3-morpholinoquinoxaline-6-carbonyl) phenyl)propane-1-sulfonamide,
N-(2,4,5-trifluoro-3-(3-(3-(hydroxymethyl)morpholino) quinoxaline-6-carbonyl)phenyl)propane-1-sulfona-mide,
N-(2-chloro-4-fluoro-3-(3-morpholinoquinoxaline-6-car-bonyl)phenyl)propane-1-sulfonamide,
N-(2,4,5-trifluoro-3-(3-morpholinoquinoxaline-6-carbo-nyl)phenyl)benzene sulfonamide,
4-Methyl-N-(2,4,5-trifluoro-3-(3-morpholinoquinoxa-line-6-carbonyl)phenyl)benzenesulfonamide,
N-(2,5-difluoro-4-(methylthio)-3-(quinoxaline-6-carbo-nyl)phenyl)propane-1-sulfonamide,
N-(2,4,5-trifluoro-3-(3-morpholinoquinoxaline-6-carbo-nyl)phenyl)propane-1-sulfonamide,
N-(3-(3-chloroquinoxaline-6-carbonyl)-2,4,5-trifluoro-phenyl)propane-1-sulfonamide, N-(3-(3-((2-(dimethylamino)ethyl)(methyl)amino)qui-
noxaline-6-carbonyl)-2,4,5-trifluorophenyl)propane-1-
sulfonamid
N-(2-chloro-4-fluoro-3-(quinoxaline-6-carbonyl)phenyl)
propane-1-sulfonamide,
N-(2-chloro-4-fluoro-3-(3-methylquinoxaline-6-carbo-
nyl)phenyl)propane-1-sulfonamide,
N-(2-chloro-3-(3-cyanoquinoxaline-6-carbonyl)-4-fluo-
rophenyl)propane-1-sulfonamide,
N-(2-chloro-4-fluoro-3-(3-methoxyquinoxaline-6-carbo-
nyl)phenyl)propane-1-sulfonamide,
N-(2-chloro-4-fluoro-3-(3-phenylquinoxaline-6-carbo-
nyl)phenyl)propane-1-sulfonamide,
N-(2-chloro-3-(3-(4-chlorophenyl)quinoxaline-6-carbo-
nyl)-4-fluorophenyl)propane-1-sulfonamide,
N-(2-chloro-4-fluoro-3-(3-(4-fluorophenyl)quinoxaline-
6-carbonyl)phenyl)propane-1-sulfonamide,
N-(3-(3-(1H-imidazol-1-yl)quinoxaline-6-carbonyl)-2-
chloro-4-fluorophenyl)propane-1-sulfonamide,
N-(2-chloro-4-fluoro-3-(3-(2-methyl-1H-imidazol-1-yl)
quinoxaline-6-carbonyl)phenyl)propane-1-sulfona-
mide,
N-(2-chloro-4-fluoro-3-(3-(5-methyl-1H-imidazol-1-yl)
quinoxaline-6-carbonyl)phenyl)propane-1-sulfona-
mide,
N-(2-chloro-4-fluoro-3-(3-(4-methyl-1H-imidazol-1-yl)
quinoxaline-6-carbonyl)phenyl)propane-1-sulfona-
mide,
N-(2-chloro-4-fluoro-3-(3-(pyridin-3-yl)quinoxaline-6-
carbonyl)phenyl)propane-1-sulfonamide,
N-(2-chloro-4-fluoro-3-(3-(6-methylpyridin-3-yl)qui-
noxaline-6-carbonyl)phenyl)propane-1-sulfonamide,
N-(2-chloro-4-fluoro-3-(3-(pyridin-4-yl)quinoxaline-6-
carbonyl)phenyl)propane-1-sulfonamide,
N-(2-chloro-4-fluoro-3-(quinoxaline-6-carbonyl)phenyl)
benzenesulfonamide,
N-(2-chloro-4-fluoro-3-(3-methylquinoxaline-6-carbo-
nyl)phenyl)benzene sulfonamide,
N-(2-chloro-3-(3-cyanoquinoxaline-6-carbonyl)-4-fluo-
rophenyl)benzenesulfonamide,
N-(2-chloro-4-fluoro-3-(3-methoxyquinoxaline-6-carbo-
nyl)phenyl)benzenesulfonamide,
N-(2-chloro-4-fluoro-3-(quinoxaline-6-carbonyl)phenyl)-
3-fluorobenzenesulfonamide,
N-(2-chloro-4-fluoro-3-(3-methylquinoxaline-6-carbo-
nyl)phenyl)-3-fluorobenzene sulfonamide,
N-(2-chloro-3-(3-cyanoquinoxaline-6-carbonyl)-4-fluo-
rophenyl)-3-fluorobenzenesulfonamide,
N-(2,4-difluoro-3-(quinoxaline-6-carbonyl)phenyl)ben-
zenesulfonamide,
N-(2,4-difluoro-3-(3-methylquinoxaline-6-carbonyl)phe-
nyl)benzenesulfonamide,
N-(3-(3-cyanoquinoxaline-6-carbonyl)-2,4-difluorophe-
nyl)benzenesulfonamide,
N-(2,4-difluoro-3-(3-methoxyquinoxaline-6-carbonyl)
phenyl)benzenesulfonamide,
N-(2,4-difluoro-3-(quinoxaline-6-carbonyl)phenyl)-3-
fluorobenzenesulfonamide,
N-(2,4-difluoro-3-(3-methylquinoxaline-6-carbonyl)phe-
nyl)-3-fluorobenzenesulfonamide,
N-(3-(3-cyanoquinoxaline-6-carbonyl)-2,4-difluorophe-
nyl)-3-fluorobenzenesulfonamide,
N-(2,4-difluoro-3-(3-methoxyquinoxaline-6-carbonyl)
phenyl)-3-fluorobenzenesulfonamide,
N-(2,4-difluoro-3-(3-morpholinoquinoxaline-6-carbonyl)
phenyl)-3-fluorobenzenesulfonamide,
N-(2,4-difluoro-3-(3-(piperazin-1-yl)quinoxaline-6-car-
bonyl)phenyl)-3-fluorobenzenesulfonamide,
N-(2,4-difluoro-3-(3-(2-hydroxyethoxy)quinoxaline-6-
carbonyl)phenyl)-3-fluorobenzenesulfonamide,
N-(2,4-difluoro-3-(3-(2-methoxyethoxy)quinoxaline-6-
carbonyl)phenyl)-3-fluorobenzenesulfonamide,
N-(3-(3-(1H-pyrazol-4-yl)quinoxaline-6-carbonyl)-2,4-
difluorophenyl)-3-fluorobenzenesulfonamide,
N-(2,4-difluoro-3-(3-(pyridin-3-yl)quinoxaline-6-carbo-
nyl)phenyl)-3-fluorobenzenesulfonamide,
N-(2,4-difluoro-3-(quinoxaline-6-carbonyl)phenyl)pro-
pane-1-sulfonamide,
N-(2,4-difluoro-3-(3-methylquinoxaline-6-carbonyl)phe-
nyl)propane-1-sulfonamide,
N-(3-(3-cyanoquinoxaline-6-carbonyl)-2,4-difluorophe-
nyl)propane-1-sulfonamide,
N-(2,4-difluoro-3-(3-methoxyquinoxaline-6-carbonyl)
phenyl)propane-1-sulfonamide,
N-(2,4-difluoro-3-(3-(piperazin-1-yl)quinoxaline-6-car-
bonyl)phenyl)propane-1-sulfonamide,
N-(2,4-difluoro-3-(3-(2-methoxyethoxy)quinoxaline-6-
carbonyl)phenyl)propane-1-sulfonamide,
N-(2,4-difluoro-3-(3-(2-hydroxyethoxy)quinoxaline-6-
carbonyl)phenyl)propane-1-sulfonamide,
N-(2,4-difluoro-3-(3-phenylquinoxaline-6-carbonyl)phe-
nyl)propane-1-sulfonamide,
N-(3-(3-(4-chlorophenyl)quinoxaline-6-carbonyl)-2,4-di-
fluorophenyl)propane-1-sulfonamide,
N-(2,4-difluoro-3-(3-(4-fluorophenyl)quinoxaline-6-car-
bonyl)phenyl)propane-1-sulfonamide,
N-(3-(3-(1H-imidazol-1-yl)quinoxaline-6-carbonyl)-2,4-
difluorophenyl)propane-1-sulfonamide,
N-(2,4-difluoro-3-(3-(2-methyl-1H-imidazol-1-yl)qui-
noxaline-6-carbonyl)phenyl)propane-1-sulfonamide,
N-(2,4-difluoro-3-(3-(5-methyl-1H-imidazol-1-yl)qui-
noxaline-6-carbonyl)phenyl)propane-1-sulfonamide,
N-(2,4-difluoro-3-(3-(4-methyl-1H-imidazol-1-yl)qui-
noxaline-6-carbonyl)phenyl)propane-1-sulfonamide,
N-(2,4-difluoro-3-(3-(1-methyl-1H-pyrazol-4-yl)qui-
noxaline-6-carbonyl)phenyl)propane-1-sulfonamide,
N-(3-(3-(1H-pyrazol-4-yl)quinoxaline-6-carbonyl)-2,4-
difluorophenyl)propane-1-sulfonamide,
N-(2,4-difluoro-3-(3-(pyridin-3-yl)quinoxaline-6-carbo-
nyl)phenyl)propane-1-sulfonamide,
N-(2,4-difluoro-3-(3-(6-methylpyridin-3-yl)quinoxaline-
6-carbonyl)phenyl)propane-1-sulfonamide,
N-(2,4-difluoro-3-(3-(pyridin-4-yl)quinoxaline-6-carbo-
nyl)phenyl)propane-1-sulfonamide, In yet another aspect, the present disclosure provides a compound chosen from the compounds set forth in Table 1 below and pharmaceutically acceptable salts thereof.

TABLE 1

Illustrative Compounds of the Present Invention

| Compound No. | Chemical Name |
|---|---|
| C01 | N-(2,4-difluoro-3-(quinoxaline-6-carbonyl)phenyl)-propane-1-sulfonamide |
| C02 | N-(3-(3-(4-chlorophenyl)quinoxaline-6-carbonyl)-2,4-difluorophenyl)propane-1-sulfonamide |
| C03 | N-(2,4-difluoro-3-(3-methoxyquinoxaline-6-carbonyl)-phenyl)propane-1-sulfonamide |
| C04 | N-(2,4,5-trifluoro-3-(quinoxaline-6-carbonyl)phenyl)-propane-1-sulfonamide |
| C05 | N-(3-(3-cyanoquinoxaline-6-carbonyl)-2,4-difluorophenyl)-propane-1-sulfonamide |

TABLE 1-continued

Illustrative Compounds of the Present Invention

| Compound No. | Chemical Name |
|---|---|
| C06 | N-(2-chloro-4-fluoro-3-(quinoxaline-6-carbonyl)phenyl)-propane-1-sulfonamide |
| C07 | N-(3,4-difluoro-5-(quinoxaline-6-carbonyl)phenyl)-propane-1-sulfonamide |
| C08 | N-(2,5-difluoro-4-(methylthio)-3-(quinoxaline-6-carbonyl)phenyl)propane-1-sulfonamide |
| C09 | N-(2,4,5-trifluoro-3-(3-morpholinoquinoxaline-6-carbonyl)phenyl)propane-1-sulfonamide |
| C10 | N-(2,4,5-trifluoro-3-(3-methoxyquinoxaline-6-carbonyl)phenyl)propane-1-sulfonamide |
| C11 | N-(3-(3-chloroquinoxaline-6-carbonyl)-2,4,5-trifluorophenyl)propane-1-sulfonamide |
| C12 | N-(3-(3-(4-chlorophenyl)quinoxaline-6-carbonyl)-2,4,5-trifluorophenyl)propane-1-sulfonamide |
| C13 | N-(3-(3-((2-(dimethylamino)ethyl)(methyl)amino)-quinoxaline-6-carbonyl)-2,4,5-trifluorophenyl)propane-1-sulfonamide |
| C14 | N-(2-chloro-4,5-difluoro-3-(quinoxaline-6-carbonyl)phenyl)propane-1-sulfonamide |
| C15 | N-(4-fluoro-3-(quinoxaline-6-carbonyl)phenyl)propane-1-sulfonamide |
| C16 | N-(3-fluoro-5-(quinoxaline-6-carbonyl)phenyl)propane-1-sulfonamide |
| C17 | N-(4-fluoro-3-(3-morpholinoquinoxaline-6-carbonyl)phenyl)propane-1-sulfonamide |
| C18 | N-(3-fluoro-5-(3-morpholinoquinoxaline-6-carbonyl)phenyl)propane-1-sulfonamide |
| C19 | N-(2,4,5-trifluoro-3-(3-methylquinoxaline-6-carbonyl)phenyl)propane-1-sulfonamide |
| C20 | N-(2,4,5-trifluoro-3-(3-(2-methyl-1H-imidazol-1-yl)-quinoxaline-6-carbonyl)phenyl)propane-1-sulfonamide |
| C21 | N-(2,4,5-trifluoro-3-(3-(4-methyl-1H-imidazol-1-yl)-quinoxaline-6-carbonyl)phenyl)propane-1-sulfonamide |
| C22 | N-(2,4,5-trifluoro-3-(3-(2-methoxyethoxy)quinoxaline-6-carbonyl)phenyl)propane-1-sulfonamide |
| C23 | N-(3-(3-(1H-imidazol-1-yl)quinoxaline-6-carbonyl)-2,4,5-trifluorophenyl)propane-1-sulfonamide |
| C24 | N-(2,4,5-trifluoro-3-(3-(piperazin-1-yl)quinoxaline-6-carbonyl)phenyl)propane-1-sulfonamide |
| C25 | N-(2,4,5-trifluoro-3-(3-(2-oxopiperazin-1-yl)quinoxaline-6-carbonyl)phenyl)propane-1-sulfonamide |
| C26 | N-(2,4,5-trifluoro-3-(3-phenylquinoxaline-6-carbonyl)phenyl)propane-1-sulfonamide |
| C27 | N-(3-(3-(1H-pyrazol-4-yl)quinoxaline-6-carbonyl)-2,4,5-trifluorophenyl)propane-1-sulfonamide |
| C28 | N-(2,4,5-trifluoro-3-(3-(4-fluorophenyl)quinoxaline-6-carbonyl)phenyl)propane-1-sulfonamide |
| C29 | N-(2,4,5-trifluoro-3-(3-morpholinoquinoxaline-6-carbonyl)phenyl)cyclopropanesulfonamide |
| C30 | N-(2,4,5-trifluoro-3-(3-(pyridin-3-yl)quinoxaline-6-carbonyl)phenyl)propane-1-sulfonamide |
| C31 | N-(2,4,5-trifluoro-3-(3-(3-oxopiperazin-1-yl)quinoxaline-6-carbonyl)phenyl)propane-1-sulfonamide |
| C32 | N-(3-(3-(diethylamino)quinoxaline-6-carbonyl)-2,4,5-trifluorophenyl)propane-1-sulfonamide |
| C33 | N-(2,4,5-trifluoro-3-(3-(pyridin-4-yl)quinoxaline-6-carbonyl)phenyl)propane-1-sulfonamide |
| C34 | N-(2,4,5-trifluoro-3-(3-(6-methylpyridin-3-yl)-quinoxaline-6-carbonyl)phenyl)propane-1-sulfonamide |
| C35 | N-(2,4,5-trifluoro-3-3-fluoroquinoxaline-6-carbonyl)phenyl)propane-1-sulfonamide |
| C36 | N-(3-(3-cyanoquinoxaline-6-carbonyl)-2,4,5-trifluorophenyl)propane-1-sulfonamide |
| C37 | N-(3,4-difluoro-5-(3-morpholinoquinoxaline-6-carbonyl)phenyl)propane-1-sulfonamide |
| C38 | N-(2,4-difluoro-3-(3-morpholinoquinoxaline-6-carbonyl)phenyl)propane-1-sulfonamide |
| C39 | N-(2,4,5-trifluoro-3-(3-(3-(hydroxymethyl)morpholino)quinoxaline-6-carbonyl)phenyl)propane-1-sulfonamide |
| C40 | N-(2,4,5-trifluoro-3-(3-(5-methyl-1H-imidazol-1-yl)-quinoxaline-6-carbonyl)phenyl)propane-1-sulfonamide |
| C41 | N-(2-chloro-4-fluoro-3-(3-morpholinoquinoxaline-6-carbonyl)phenyl)propane-1-sulfonamide |
| C42 | N-(2,4,5-trifluoro-3-(3-morpholinoquinoxaline-6-carbonyl)phenyl)benzenesulfonamide |
| C43 | 4-methyl-N-(2,4,5-trifluoro-3-(3-morpholinoquinoxaline-6-carbonyl)phenyl)benzenesulfonamide |

In some embodiments, a compound of Formula I binds to a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I binds to a kinase selected from the group consisting of A-Raf, B-Raf, B-Raf V600E mutant, B-RafV600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, and any mutated versions thereof. In some embodiments, the compound of Formula I binds to a kinase selected from the group consisting of A-Raf, B-Raf, B-Raf V600E mutant, B-Raf V600E/T5291 mutant, or c-Raf-1. For example, the compound of Formula I binds to a kinase which is B-Raf or B-RafV600E mutant. In some embodiments, a compound of Formula I binds to a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof, with a Kd which is lower than 50 μM, 25 μM, 10 μM, 5 μM, or 1 μM as measured in an in vitro assay. For example, the compound of Formula I binds to a kinase selected from the group consisting of A-Raf, B-Raf, B-RafV600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, and any mutated versions thereof with a Kd which is lower than 50 μM, 25 μM, 10 μM, 5 μM, or 1 μM as measured in an in vitro assay. In some embodiments, the compound of Formula I binds to a kinase selected from the group consisting of A-Raf, B-Raf, B-Raf V600E mutant, B-Raf V600E/T5291 mutant, or c-Raf-1 with a Kd which is lower than 50 μM, 25 μM, 10 μM, 5 μM, or 1 μM as measured in an in vitro assay. For example, the compound of Formula I binds to a kinase which is B-Raf or B-Raf V600E mutant with a Kd which is lower than 50 µM, 25 µM, 10 µM, 5 µM, or 1 µM as measured in an in vitro assay.

In some embodiments, a compound of Formula I inhibits a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I inhibits a kinase selected from the group consisting of A-Raf, B-Raf, B-Raf V600E mutant, B-RafV600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, and any mutated versions thereof. In some embodiments, the compound of Formula I inhibits a kinase selected from the group consisting of A-Raf, B-Raf, B-Raf V600E mutant, B-Raf V600E/T5291 mutant, or c-Raf-1. For example, the compound of Formula I inhibits a kinase which is B-Raf or B-Raf V600E mutant. In some embodiments, a compound of Formula I inhibits a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof with an $IC_{50}$ in an in vitro assay of 10 µM, 5 µM, 2 µM, 1 µM, 500 nM, 200 nM, 100 nM, 50 nM, 25 nM, 10 nM, 5 nM or less as ascertained in an in vitro kinase assay. For example, the compound of Formula I inhibits a kinase selected from the group consisting of A-Raf, B-Raf, B-RafV600E mutant, B-RafV600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, and any mutated versions thereof with an $IC_{50}$ in an in vitro assay of 10 µM, 5 µM, 2 µM, 1 µM, 500 nM, 200 nM, 100 nM, 50 nM, 25 nM, 10 nM, 5 nM or less as ascertained in an in vitro kinase assay.

In some embodiments, the compound of Formula I inhibits a kinase selected from the group consisting of A-Raf, B-Raf, B-RafV600E mutant, B-RafV600E/T5291 mutant, or c-Raf-1 with an $IC_{50}$ in an in vitro assay of 10 µM, 5 µM, 2 µM, 1 µM, 500 nM, 200 nM, 100 nM, 50 nM, 25 nM, 10 nM, 5 nM or less as ascertained in an in vitro kinase assay. For example, the compound of Formula I inhibits a kinase which is B-Raf or B-Raf V600E mutant with an $IC_{50}$ in an in vitro assay of 10 µM, 5 µM, 2 µM, 1 µM, 500 nM, 200 nM, 100 nM, 50 nM, 25 nM, 10 nM, 5 nM or less as ascertained in an in vitro kinase assay.

In some embodiments, the compound of Formula I inhibits the activity of one or more kinases selected from the group consisting of A-Raf, B-Raf, B-Raf V600E mutant, B-Raf V600E/T5291 mutant, and c-Raf-1 with an $IC_{50}$ in an in vitro assay of 1 µM, 500 nM, 200 nM, 100 nM, 50 nM, 25 nM, 10 nM, 5 nM or less as ascertained in an in vitro kinase assay.

In some embodiments, the compound of Formula I selectively inhibits the activity of one or more kinases selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof.

For example, the compound of Formula I selectively inhibits the activity of one or more kinases selected from the group consisting of A-Raf, B-Raf, B-Raf V600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret. In some embodiments, the compound of Formula I selectively inhibits the activity of one or more kinases selected from the group consisting of A-Raf, B-Raf, B-Raf V600E mutant, B-Raf V600E/T5291 mutant, and c-Raf-1.

In some embodiments, the compound of Formula I selectively inhibits the activity of B-Raf or B-Raf V600E mutant relative to one or more kinases selected from the group consisting of ABL1, AKT1 (PKB alpha), AURKB (Aurora B), BLK, BTK, CDK1/cyclin B, CHEK1 (CHK1), CSF1R (FMS), CSNK1G2 (CK1 gamma 2), EGFR (ErbB1), FGFR1, FGR, FLT3, FRAP1 (mTOR), FYN, IGF1R, IKBKB (IKK beta), INSR, KDR (VEGFR2), KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRc, SRMS (Srm), and YES1. In some embodiments, the compound of Formula I selectively inhibits the activity of one or more kinases selected from the group consisting of A-Raf, B-Raf, B-Raf V600E mutant, B-Raf V600E/T5291 mutant, and c-Raf-1 with an $IC_{50}$ which is ½, ⅓$^{rd}$, ¼$^{th}$, ⅕$^{th}$, 1/7$^{th}$, 1/10$^{th}$, 1/15$^{th}$, 1/20$^{th}$, 1/25$^{th}$, 1/30$^{th}$, 1/40$^{th}$, 1/50$^{th}$, 1/100$^{th}$, 1/150$^{th}$, 1/200$^{th}$, 1/300$^{th}$, 1/400$^{th}$, 1/500$^{th}$, 1/1000$^{th}$, 1/2000$^{th}$ or less than the $IC_{50}$ for a kinase selected from the group consisting of ABL1, AKT1 (PKB alpha), AURKB (Aurora B), BLK, BTK, CDK1/cyclin B, CHEK1 (CHK1), CSF1R (FMS), CSNK1G2 (CK1 gamma 2), EGFR (ErbB1), FGFR1, FGR, FLT3, FRAP1 (mTOR), FYN, IGF1R, IKBKB (IKK beta), INSR, KDR (VEGFR2), KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2

(PKC beta II), PTK2B (FAK2), PTK6 (Brk), RAF1 (cRAF) Y340D Y341D, RET, RPS6KB1 (p70S6K), SRc, SRMS (Srm), and YES1.

In some embodiments, one or more compounds of Formula I are capable of inhibiting cellular proliferation. For example, in some cases, one or more compounds of Formula I inhibit proliferation of tumor cells or tumor cell lines. For example, such cell lines express a kinase which is B-raf or B-raf V600E mutant. In some cases, the compounds of Formula I inhibit A375 or SK-MEL-28 cell proliferation in vitro or in an in vivo model such as a xenograft mouse model. In some cases, in vitro cultured A375 or SK-MEL-28 cell proliferation may be inhibited with an $IC_{50}$ of less than 100 nM, 75 nM, 50 nM, 25 nM, 15 nM, 10 nM, 5 nM, 3 nM, 2 nM, 1 nM, 0.5 nM, 0.1 nM or less by one or more compounds of Formula I, such as the compounds listed in Table 1.

B. Methods of Making

Compounds disclosed herein may be prepared by the routes described below. Materials used herein are either commercially available or prepared by synthetic methods generally known in the art. These schemes are not limited to the compounds listed or by any particular substituents, which are employed for illustrative purposes. Although various steps of are described and depicted in Schemes A-C, the steps in some cases may be performed in a different order than the order shown in Schemes A-C. Various modifications to these synthetic reaction schemes may be made and will be suggested to one skilled in the art having referred to the disclosure contained in this Application. Numbering does not necessarily correspond to that of claims or other tables.

In Scheme A, compounds of Formula I are synthesized by activating the carboxyl group in A-1 to provide A-2 with a leaving group attached to the carbonyl. Examples of leaving groups include, but are not limited to, dimethylhydroxylamino (e.g. Weinreb amide), halogen, alkane- or arylsulfonyloxy, or acyloxy, and the like. In a further embodiment, A-2 is a Weinreb amide. In a separate reaction vessel, aryl A-3 is subjected to a metallation reaction to form metallated aryl A-4. Suitable reagents for carrying out the metallation reaction include, but are not limited to, n-BuLi, sec-BuLi, t-BuLi, t-BuOK, or i-PrMgCl lithium chloride complex, and the like. Suitable solvents include, but are not limited to, tetrahydrofuran, diethyl ether, petane, 1,4-dioxane, methyl t-butyl ether, and a mixture thereof. Typically without isolation, metallated aryl A-4 is reacted with compound A-2 to give diaryl ketone A-5. The reaction is generally carried out at a low temperature, for example, −20 to −100° C. After removing the protecting group in A-5, the anilino nitrogen is sulfonated to give target compound Formula I. Examples of protecting group include, but are not limited to —C(=O)Ot-Bu and —C(=O)t-Bu. The deprotection can be carried out with strong acids, such as HCl, HBr, trifluoroaceti acid, and $H_2SO_4$, or strong bases, such as NaOH, KOH, or CsOH.

Scheme A

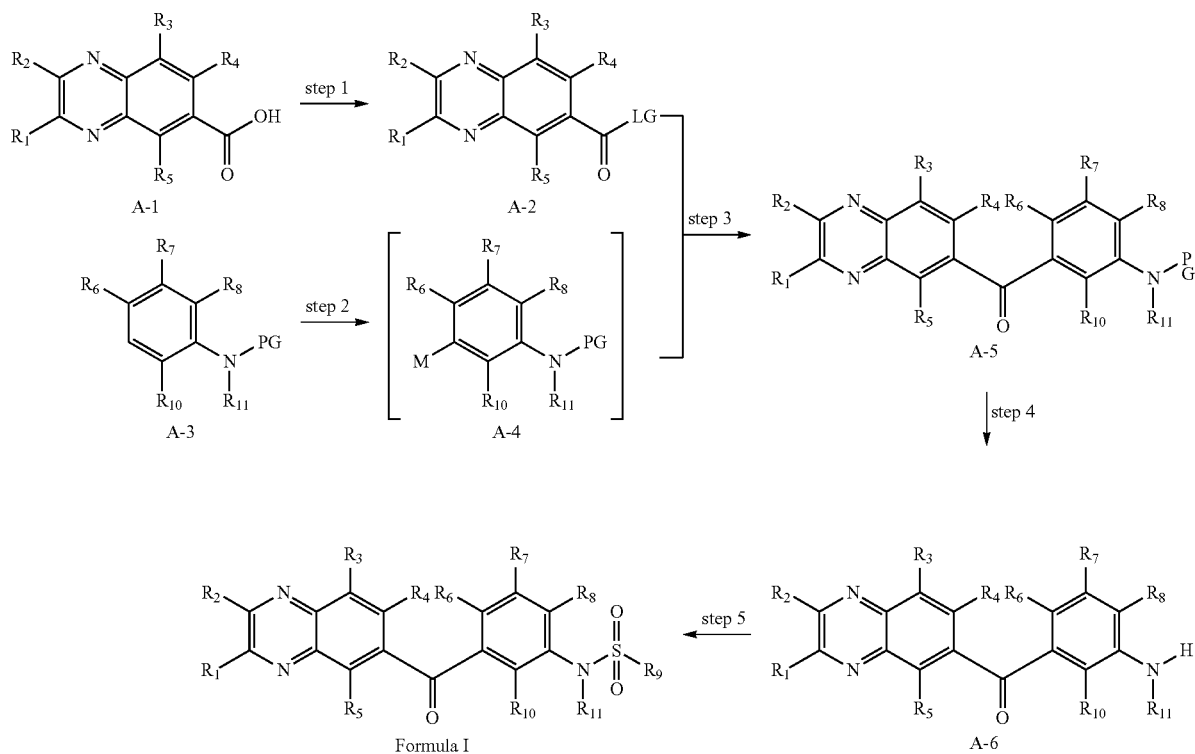

LG = Leaving Group
PG = Protecting Group

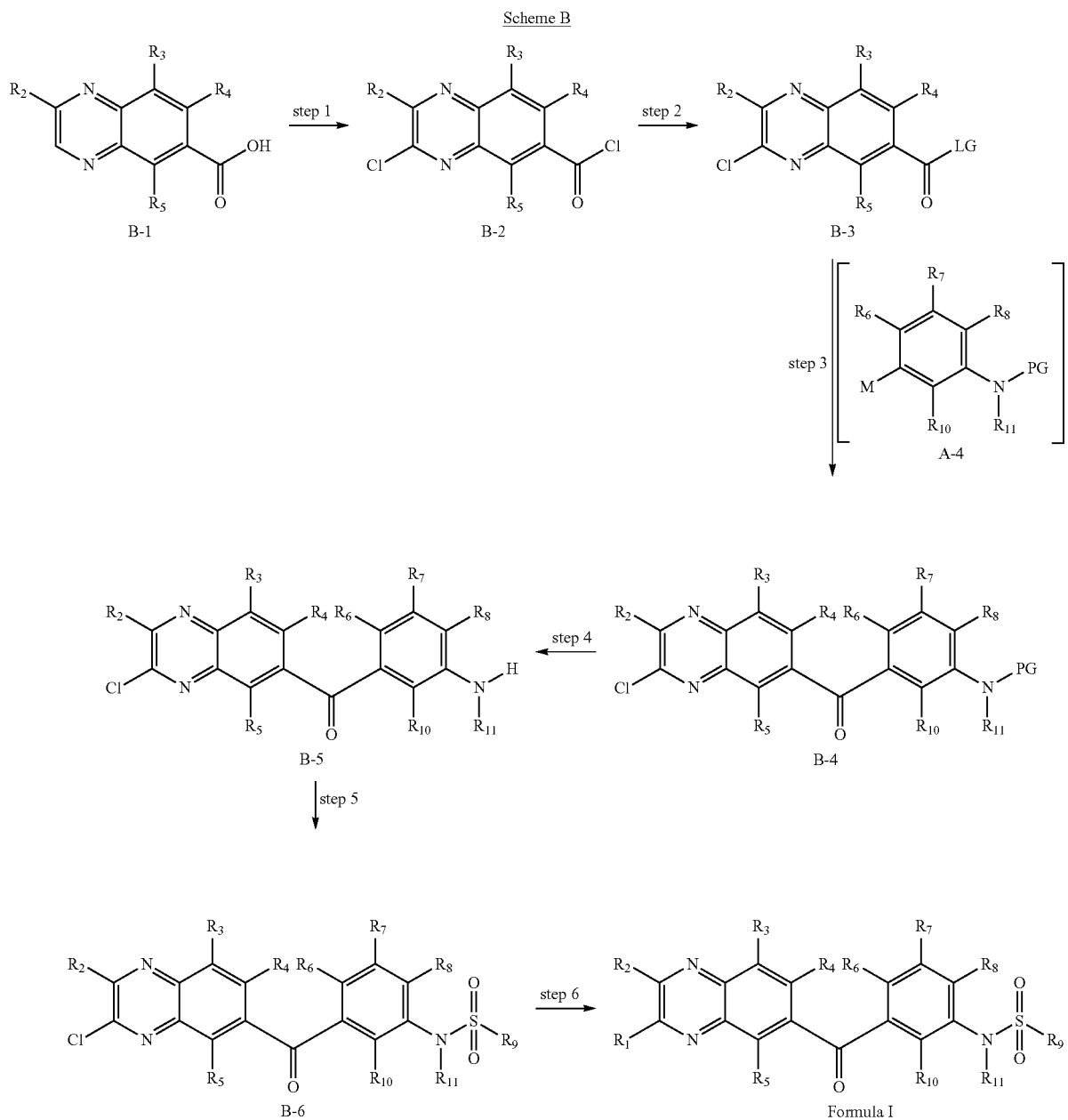

Scheme B

In Scheme B, carboxylic acid B-1 is used as the starting material. Chlorination of B-1 yields acid chloride B-2. Depending upon the substituents on the quinoxaline ring, the heteroaryl may be selectively chlorinated. Following similar procedures as described in Scheme A, activated carbonyl compound B-3 is converted to diaryl ketone B-6. $R_1$ group is then introduced under nucleophilic displacement or transition metal catalyzed cross-coupling conditions to give target Formula I. Examples of nucleophiles under nucleophilic displacement conditions include alcohols, amines, amides, alkylthiols, cyanide, halogen, and heteroaryls. Under the nucleophilic displacement conditions, a strong base may be added to facilitate the transformation. Suitable strong bases include $Cs_2CO_3$, NaH, KH, t-BuOK, LiH, and $CaH_2$. Suitable solvents include, but are not limited to, DMF, DMSO, DMA, and N-methyl piperidone. The reaction are generally carried out at a temperature ranging from 25-240° C. Exemplary transition metal catalyzed cross-coupling reactions include, Negishi, Suzuki, Stille and Heck coupling reactions (see *Cross-Coupling Reactions: A Practical Guide*, Norio Miyaura et al., Springer; $1^{st}$ edition 2002, and is herein incorporated by reference). In a further embodiment, Suzuki cross-coupling reaction with aryl, heteroaryl, or alkyl boronic acid or ester as nucleophile, in the presence of a base, such as $Na_2CO_3$, $K_2CO_3$, $Cs_2CO_3$, and a Pd catalyst, is used to introduce $R_1$ group. The reaction is generally carried out at a temperature ranging from 35 to 180° C. in a suitable solvent such as 1,4-dioxane, water, tetrahydrofuran, or a mixture thereof.

Scheme C

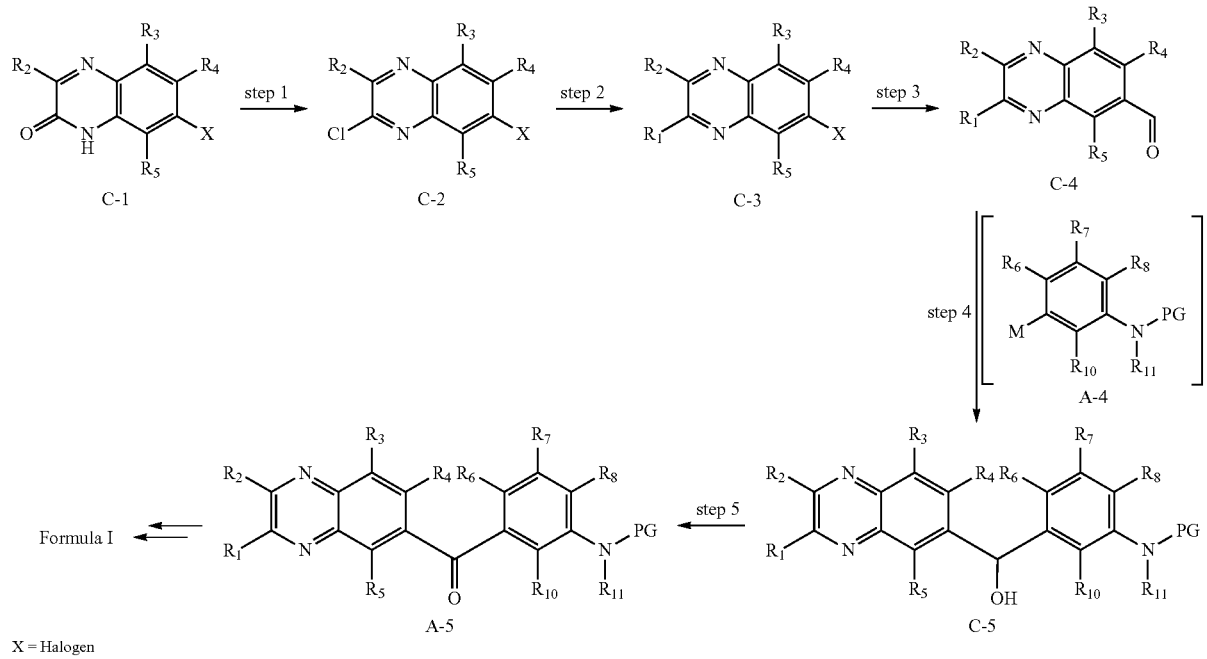

X = Halogen

In Scheme C, the synthesis commences with dihydroquinoxalinone C-1. Chlorination of C-1 yields chloride C-2. $R_1$ group is introduced at this stage via a displacement or cross coupling reaction as described in Scheme B. The remaining aryl halide in C-3 is converted to a formyl group via a transition metal catalyzed formylation reaction. Suitable formylation conditions include reacting the substrate in the presence of CO gas, a reducing reagent, such as a trialkyl silane, an amine base, a Pd catalyst and a ligand at a temperature ranging from 40 to 160° C. Reaction of formyl C-4 with A-4 gives alcohol C-5, which yields diaryl ketone A-5 upon oxidation. As described in Scheme A, A-5 is converted to a compound of Formula I.

C. Pharmaceutical Compositions and Formulations

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound of Formula I, and a pharmaceutically acceptable diluent(s), excipient(s), or carrier(s). In certain embodiments, the compounds described are administered as pharmaceutical compositions in which compounds of Formula I, are mixed with other active ingredients, as in combination therapy. Encompassed herein are all combinations of actives set forth in the combination therapies section below and throughout this disclosure. In specific embodiments, the pharmaceutical compositions include one or more compounds of Formula I.

A pharmaceutical composition, as used herein, refers to a mixture of a compound of Formula I, with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Formula I, provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of Formula I, is formulated in an aqueous solution. In specific embodiments, the aqueous solution is selected from, by way of example only, a physiologically compatible buffer, such as Hank's solution, Ringer's solution, or physiological saline buffer. In other embodiments, one or more compound of Formula I, is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including compounds of Formula I, are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a compound of Formula I is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Formula I are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula I are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula I, is accomplished by means of iontophoretic patches and the like. In certain embodiments, transdermal patches provide controlled delivery of the compounds of Formula I. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Formula I, are formulated for administration by inhalation. Various forms suitable for administration by inhalation include, but are not limited to, aerosols, mists or powders. Pharmaceutical compositions of Formula I, are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of Formula I, are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Formula I, are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula I, described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising at least one compound of Formula I, illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Formula I. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

D. Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

E. Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, Compositions containing a compound provided herein formulated in a compatible pharmaceutical carrier are prepared, placed in an appropriate container, and labeled for treatment of an indicated condition.

F. Methods of Use

The chemical entities described herein are useful in the treatment, or in the preparation of a medicament for the treatment of various disorders. For example, compounds of Formula I are useful as inhibitors of protein kinases. In some embodiments, the chemical entities described herein are inhibitors of one or more kinases. For example, compounds of Formula I are inhibitors of A-Raf, B-Raf, C-Raf and of mutants of such kinases, including the B-Raf V600E mutant. Thus, without wishing to be bound by any particular theory, the compounds of Formula I are particularly useful for treating or lessening the severity of a disease, condition, or disorder where activation of one or more kinases, such as Raf kinases, which is implicated in the disease, condition, or disorder. When activation of Raf kinases is implicated in a particular disease, condition, or disorder, the disease, condition, or disorder may also be referred to as "Raf-mediated disease" or disease symptom. Accordingly, in another aspect, the present invention provides a method for treating or lessening the severity of a disease, condition, or disorder where activation or one or more of Raf kinases is implicated in the disease state.

The inhibition of Raf kinases may be assayed in vitro, in vivo or in a cell line. In vitro assays include assays that determine inhibition of either the phosphorylation activity or ATPase activity of activated Raf kinase. Alternate in vitro assays quantitate the ability of the inhibitor to bind to Raf kinase. Inhibitor binding may be measured by radiolabelling the inhibitor prior to binding, isolating the inhibitor, complex and determining the amount of radiolabel bound. Alternatively, inhibitor binding may be determined by running a competition experiment where new inhibitors are incubated with Raf kinase bound to known radioligands.

The chemical entities described herein may be prepared in substantially pure form, typically by standard chromatographic methods, prior to formulation in a pharmaceutically acceptable form.

The chemical entities described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the chemical entities described herein are used for the treatment of cancers of the
i. digestive system including, without limitation, the esophagus, stomach, small intestine, colon (including colorectal), liver & intrahepatic bile duct, gallbladder & other biliary, pancreas, and other digestive organs;
ii. respiratory system, including without limitation, larynx, lung & bronchus, and other respiratory organs;
iii. skin;
iv. thyroid;
v. breast;
vi. genital system, including without limitation, uterine cervix, ovary, and prostate;
vii. urinary system, including without limitation, urinary bladder and kidney and renal pelvis; and
viii. oral cavity & pharynx, including without limitation, tongue, mouth, pharynx, and other oral cavity.

In some embodiments, the chemical entities described herein are used for the treatment of colon cancer, liver cancer, lung cancer, melanoma, thyroid cancer, breast cancer, ovarian cancer, and oral cancer.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3 methylenedioxyanilino)-7-[2-(4-methylpiperazin-1-yl)ethoxy]-5-tetrahydropyran-4yloxy-quinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chem., 2004, 47, 66586661) and bosutinib (SK1-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifamib (RI15777) and lonafarnib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4.{4-fluoro-2-methylindol-5-yloxy)-6-methoxy-7-(3pyrrolidin-1-ylpropoxy) quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combretastatin A4 and compounds disclosed in International Patent Applications WO 99/02166, WO 00/40529, WO 00/41669, WO 01/92224, WO02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

In certain embodiments, the at least one chemical entity is administered in combination with one or more agents chosen from pacliataxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

When a chemical entity described herein is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one chemical entity is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the chemical entity, such as including, e.g., from about 1 mg to about 1000 mg. The quantity of the at least one chemical entity in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one chemical entity described herein is not the sole active ingredient, it may be possible to administer lesser amounts of the at least one chemical entity and still have therapeutic or prophylactic effect.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The amount and frequency of administration of the at least one chemical entities described herein, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one chemical entities described herein need not be administered in the same pharmaceutical composition as a chemotherapeutic agent, and may, because of different physical and chemical characteristics, be administered by a different route. For example, the chemical entities/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemical entity (and where appropriate, chemotherapeutic agent and/or radiation) will depend upon the diagnosis of the attending physicians and their judgment of the condition of the subject and the appropriate treatment protocol.

The chemical entities described herein (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the chemical entity/composition.

In combinational applications and uses, the chemical entity/composition and the chemotherapeutic agent and/or radiation need not be administered simultaneously or essentially simultaneously, and the initial order of administration of the chemical entity/composition, and the chemotherapeutic agent and/or radiation, may not be important. Thus, the at least one chemical entity described herein may be administered first followed by the administration of the chemotherapeutic agent and/or radiation; or the chemotherapeutic agent and/or radiation may be administered first followed by the administration of the at least one chemical entity described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one chemical entity described herein followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Example 1

Preparation of N-(2,4,5-trifluoro-3-(quinoxaline-6-carbonyl)phenyl)propane-1-sulfonamide

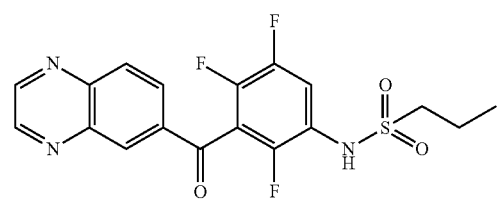 [SMILES: CCCS(=O)(=O)Nc1cc(F)c(F)c(C(=O)c2ccc3nccnc3c2)c1F]

N-(2,4,5-trifluoro-3-(quinoxaline-6-carbonyl)phenyl) propane-1-sulfonamide

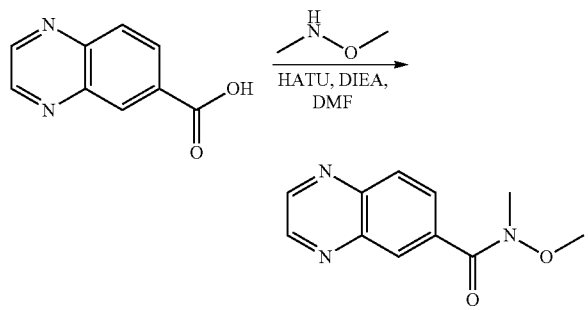

To a solution of quinoxaline-6-carboxylic acid (5.1 g, 29.3 mmol, 1.0 eq) in DMF (100 mL) were added HATU (13.3 g, 35 mmol. 1.2 eq), DIEA (20 mL, 117.2 mmol, 4.0 eq) and O,N-dimethyl-hydroxylamine hydrochloride salt (3.38 g, 35 mmol, 1.2 eq). The mixture was stirred at rt overnight, then the solvent was evaporated. The resulting residue was purified by flash column chromatography (PE/EA=2/1, v/v) to afford N-methoxy-N-methylquinoxaline-6-carboxamide as yellow solid (5.1 g, 80%).

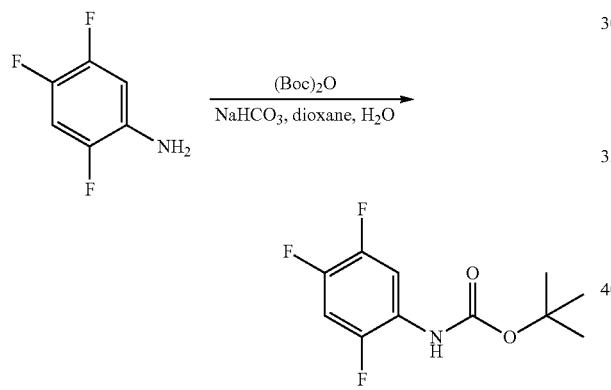

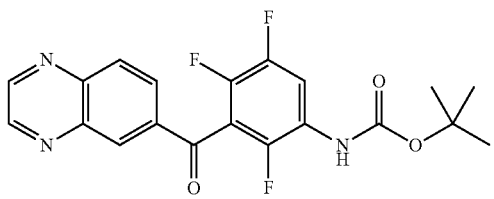

To a solution of tert-butyl (2,4,5-trifluorophenyl)carbamate (2.72 g, 11 mmol, 1.1 eq.) in THF (150 mL) cooled at −78° C. was added n-BuLi (9.17 mL, 22 mmol, 2.2 eq.) dropwise. The resulting mixture was stirred at −78° C. for 30 min, then a solution of N-methoxy-N-methylquinoxaline-6-carboxamide (2.17 g, 10 mmol, 1.0 eq.) in THF (50 mL) was added dropwise. The resulting mixture was stirred at −78° C. for 1 h, then quenched by the addition of NH4Cl solution. The mixture was extracted with EA (100 mL×3). The combined organic layers were dried over Na2SO4 and concentrated. The resulting residue was purified by flash column chromatography (PE/EA=4/1, v/v) to afford tert-butyl (2,4,5-trifluoro-3-(quinoxaline-6-carbonyl)phenyl)carbamate as yellow foam (600 mg, 14.9%)

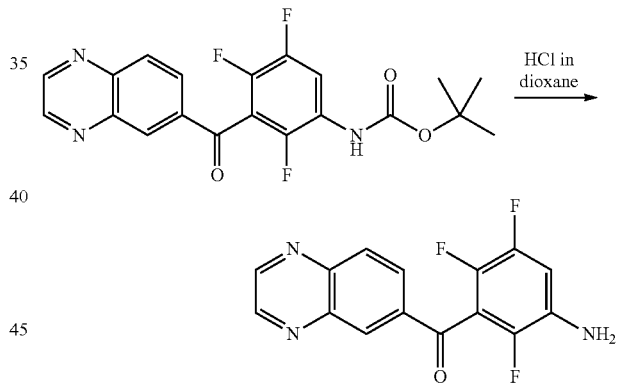

To a solution of 2,4,5-trifluoroaniline (25 g, 0.17 mol, 1 eq.) in dioxane (150 mL) and H₂O (150 mL) was added NaHCO₃ (57 g, 0.68 mmol, 4 eq.) and (Boc)₂O (74 g, 0.34 mol, 2 eq.). The resulting mixture was stirred at rt overnight, then the solvent was evaporated. The aqueous phase was extracted with EA (100 mL×3). The combined organic layers were dried over Na₂SO₄, filtered and concentrated. The resulting residue was purified by flash column chromatography (PE) to afford tert-butyl (2,4,5-trifluorophenyl) carbamate as a white solid (15 g, 35.7%).

A solution of tert-butyl (2,4,5-trifluoro-3-(quinoxaline-6-carbonyl)phenyl)carbamate (400 mg, 1 mmol, 1 eq.) in 6 N HCl/dioxane (50 mL) was stirred at rt for 3 h. The solvent was evaporated, and the resulting residue was used in the next step without further purification.

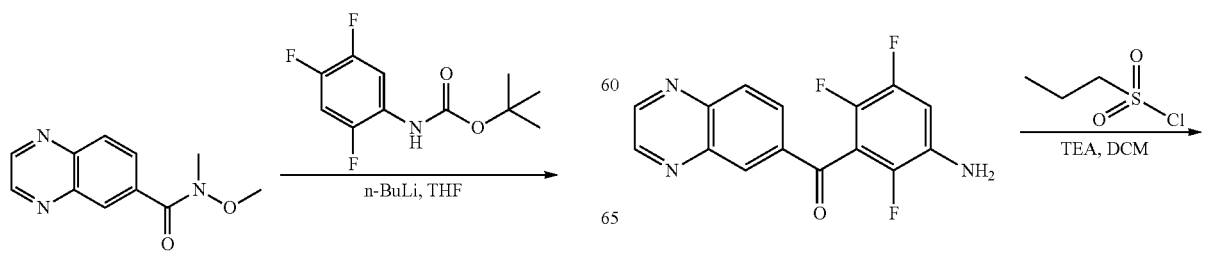

-continued

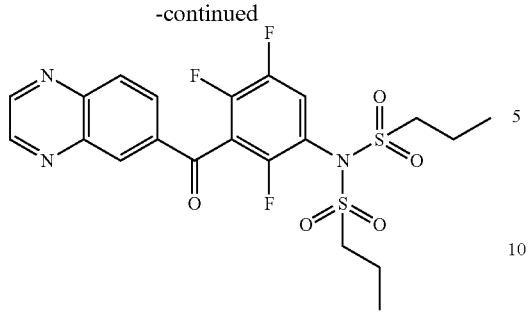

To a solution of (3-amino-2,5,6-trifluorophenyl)(quinoxalin-6-yl)methanone (300 mg, 1 mmol, 1 eq.) in DCM (30 mL) was added TEA (1.0 g mg, 10 mmol, 10 eq.), followed by propane-1-sulfonyl chloride (713 mg, 5 mmol, 5 eq.). After the resulting mixture was stirred at rt for 1 h, the mixture was washed with water and extracted with DCM (20 mL×3). The combined organic layers were dried over Na2SO4, filtered and concentrated. The resulting residue was purified by flash column chromatography (PE/EA=2/1, v/v) to afford N-(propylsulfonyl)-N-(2,4,5-trifluoro-3-(quinoxaline-6-carbonyl)phenyl)propane-1-sulfonamide (170 mg, 33.0%).

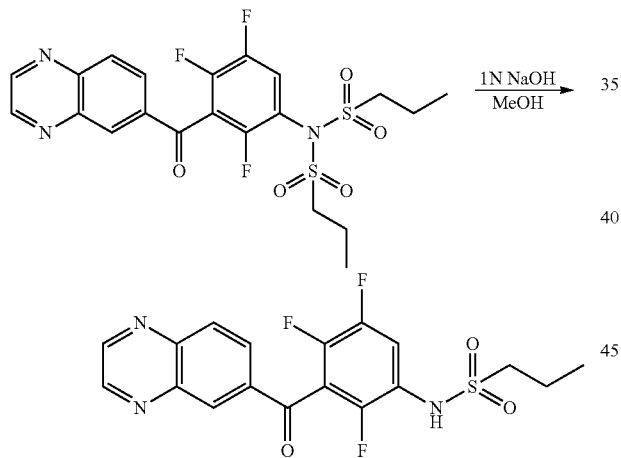

To a solution of N-(propylsulfonyl)-N-(2,4,5-trifluoro-3-(quinoxaline-6-carbonyl)phenyl)propane-1-sulfonamide (60 mg, 0.12 mmol, 1 eq.) in MeOH (5 mL) was added NaOH (1N, 0.24 mL, 0.24 mmol, 2 eq.). The resulting mixture was stirred at rt for 1 h, then concentrated. The resulting residue was purified by flash column chromatography (PE/EA=1/1, v/v) to afford N-(2,4,5-trifluoro-3-(quinoxaline-6-carbonyl)phenyl)propane-1-sulfonamide (31.2 mg, 63.7%). LRMS (M−H+) m/z calculated 408.4. found 408.1. 1H NMR (CDCl3, 400 MHz) δ 8.95-8.99 (dd, 2 H), 8.45 (s, 1 H), 8.38-8.41 (dd, 1 H), 8.27-8.29 (d, 1 H), 7.70-7.77 (m, 1 H), 6.74 (s, 1 H), 3.13-3.17 (m, 2 H), 1.87-1.93 (m, 2 H), 1.06-1.10 (s, 3 H).

Example 2

Preparation of N-(2-chloro-4,5-difluoro-3-(quinoxaline-6-carbonyl)phenyl)propane-1-sulfonamide

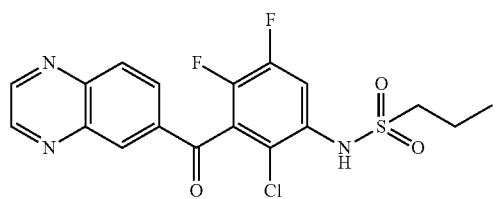

N-(2-chloro-4,5-difluoro-3-(quinoxaline-6-carbonyl)phenyl)propane-1-sulfonamide

N-(2-chloro-4,5-difluoro-3-(quinoxaline-6-carbonyl)phenyl)propane-1-sulfonamide was prepared as described for N-(2,4,5-trifluoro-3-(quinoxaline-6-carbonyl)phenyl)propane-1-sulfonamide. LRMS (M+H+) m/z calculated 426.0. found 426.0. 1H NMR (CDCl3, 400 MHz) δ 8.95-8.99 (dd, 2 H), 8.39-8.43 (m, 2 H), 8.29-8.31 (m, 1 H), 7.79-7.84 (m, 1 H), 6.87 (m, 1 H), 3.14-3.18 (m, 2 H), 1.89-1.95 (m, 2 H), 1.08-1.12 (t, 3 H).

Example 3

Preparation of N-(2-chloro-4-fluoro-3-(quinoxaline-6-carbonyl)phenyl)propane-1-sulfonamide

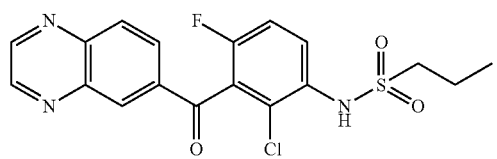 [SMILES: CCCS(=O)(=O)Nc1ccc(F)c(C(=O)c2ccc3nccnc3c2)c1Cl]

N-(2-chloro-4-fluoro-3-(quinoxaline-6-carbonyl)phenyl)propane-1-sulfonamide

N-(2-chloro-4-fluoro-3-(quinoxaline-6-carbonyl)phenyl)propane-1-sulfonamide was prepared as described for N-(2,4,5-trifluoro-3-(quinoxaline-6-carbonyl)phenyl)propane-1-sulfonamide. LRMS (M+H+) m/z calculated 408.1. found 408.0. 1H NMR (CDCl3, 400 MHz) δ 8.93-8.98 (dd, 2 H), 8.38-8.43 (m, 2 H), 8.27-8.29 (d, 1 H), 7.86-7.90 (m, 1 H), 7.20-7.27 (m, 1H), 6.78 (s, 1 H), 3.110-3.14 (m, 2 H), 1.87-1.93 (m, 2 H), 1.02-1.10 (s, 3 H).

Example 4

Preparation of N-(2,4-difluoro-3-(quinoxaline-6-carbonyl)phenyl)propane-1-sulfonamide

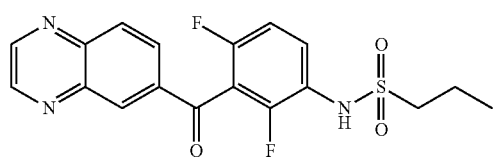 [SMILES: CCCS(=O)(=O)Nc1ccc(F)c(C(=O)c2ccc3nccnc3c2)c1F]

N-(2,4-difluoro-3-(quinoxaline-6-carbonyl)phenyl)propane-1-sulfonamide

N-(2,4-difluoro-3-(quinoxaline-6-carbonyl)phenyl)propane-1-sulfonamide was prepared as described for N-(2,4,5-trifluoro-3-(quinoxaline-6-carbonyl)phenyl)propane-1-sulfonamide. LRMS (M–H⁺) m/z calculated 390.1. found 389.8. ¹H NMR (CDCl₃, 400 MHz) δ8.93-8.98 (dd, 2H), 8.45 (s, 1H), 8.38-8.41 (m, 1H), 8.25-8.28 (m, 1H), 7.79-7.82 (m, 1H), 7.07-7.11 (t, 1H), 6.71 (s, 1H), 3.10-3.14 (m, 2H), 1.87-1.92 (m, 2H), 1.04-1.08 (t, 3H).

Example 5

Preparation of N-(2,5-difluoro-4-(methylthio)-3-(quinoxaline-6-carbonyl)phenyl)propane-1-sulfonamide

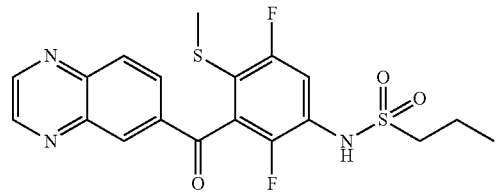 [SMILES: CCCS(=O)(=O)Nc1cc(F)c(SC)c(C(=O)c2ccc3nccnc3c2)c1F]

N-(2,5-difluoro-4-(methylthio)-3-(quinoxaline-6-carbonyl)phenyl)propane-1-sulfonamide

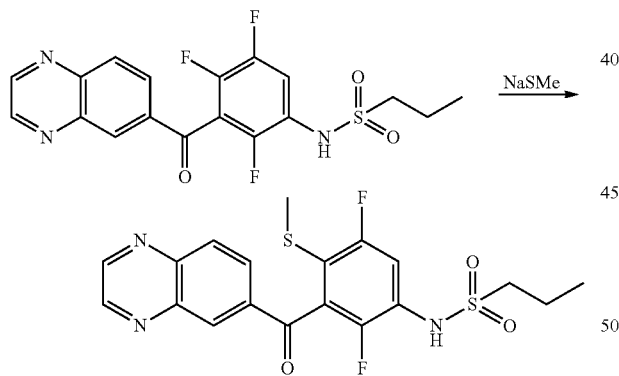

To a solution of N-(2,4,5-trifluoro-3-(quinoxaline-6-carbonyl)phenyl)propane-1-sulfonamide (40 mg, 0.1 mmol, 1.0 eq.) in THF (10 mL) was added NaSCH₃ (28.4 mg, 0.4 mmol, 4.0 eq.). The resulting mixture was stirred at rt overnight, then concentrated. The resulting residue was purified by flash column chromatography (PE/EA=1/1, v/v) to afford N-(2,5-difluoro-4-(methylthio)-3-(quinoxaline-6-carbonyl)phenyl)propane-1-sulfonamide (12.1 mg, 27.7%). LRMS (M–H⁺) m/z calculated 436.1. found 436.1. ¹H NMR (CDCl₃, 400 MHz) δ 8.92-8.97 (dd, 2 H), 8.26-8.42 (m, 3 H), 8.17-8.26 (m, 2 H), 7.57-7.61 (m, 1 H), 7.03 (s, 1 H), 3.18-3.22 (m, 2 H), 2.29 (s, 3 H), 1.87-1.96 (m, 2 H), 1.07-1.11 (t, 3 H).

Example 6

Preparation of N-(2,4,5-trifluoro-3-(3-morpholinoquinoxaline-6-carbonyl)phenyl)propane-1-sulfonamide

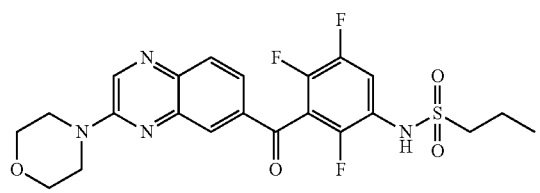 [SMILES: CCCS(=O)(=O)Nc1cc(F)c(F)c(C(=O)c2ccc3ncc(N4CCOCC4)nc3c2)c1F]

N-(2,4,5-trifluoro-3-(3-morpholinoquinoxaline-6-carbonyl)phenyl)propane-1-sulfonamide

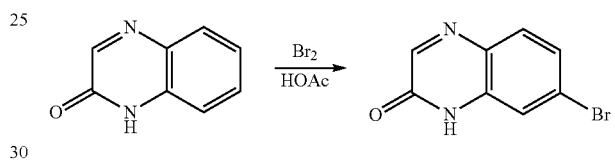

To a solution of quinoxalin-2(1H)-one (54.64 g, 374 mmol, 1.0 eq.) in HOAc (1000 mL) was added a solution of Br₂ (19.18 mL, 374 mmol, 1.0 eq.) in HOAc (200 mL) dropwise. The resulting mixture was stirred at rt for 12 h, then poured into ice-water. The precipitate was collected by filtration and dried to afford 7-bromoquinoxalin-2(1H)-one as an off-white solid (74 g, 88%).

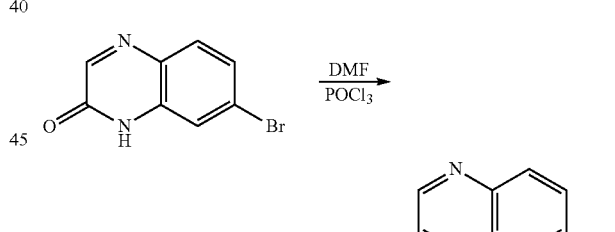

To a suspension of 7-bromoquinoxalin-2(1H)-one (224 g, 1 mol, 1.0 eq.) in POCl₃ (1000 mL) was added DMF (3.65 g, 0.05 mol, 0.05 eq.). The resulting mixture was stirred at 120° C. for 2 h, then cooled to rt and slowly poured into ice-water with vigorous stirring. The precipitate was collected by filtration and dried to afford 7-bromo-2-chloroquinoxaline as brown solid (180 g, 75%).

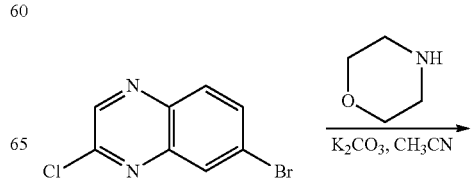

-continued

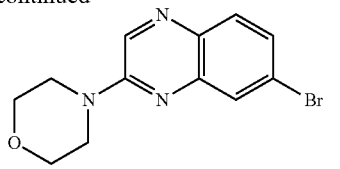

To a solution of 7-bromo-2-chloroquinoxaline (50 g, 0.2 mol, 1.0 eq.) in CH₃CN (200 mL) were added morpholine (89 g, 1.02 mol, 5.0 eq.) and K₂CO₃ (85 g, 0.61 mol, 3.0 eq). The resulting mixture was stirred at 90° C. for 2 h, then cooled and filtered. The filtrate was concentrated and the residue was re-crystallized from EA to afford 4-(7-bromo-quinoxalin-2-yl)morpholine (59 g, 98.3%).

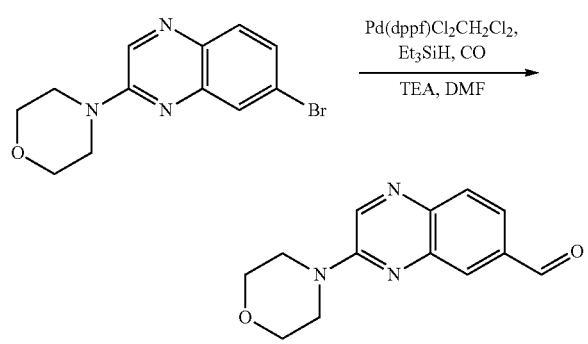

To a solution of 4-(7-bromoquinoxalin-2-yl)morpholine (59 g, 0.2 mol, 1.0 eq.) in DMF (500 mL) was added TEA (139 mL, 1.0 mol, 5.0 eq.), Et₃SiH (127 mL, 0.8 mol, 4.0 eq) and Pd(dppf)Cl₂.CH₂Cl₂ (8.16 g, 0.01 mol, 0.05 eq.). The resulting mixture was stirred at 90° C. for 12 h in an autoclave under CO (1 MPa), then cooled and concentrated. The resulting residue was purified by flash column chromatography (EA/PE=1/1) to afford 3-morpholinoquinoxaline-6-carbaldehyde as a yellow solid (40 g, 82.3%).

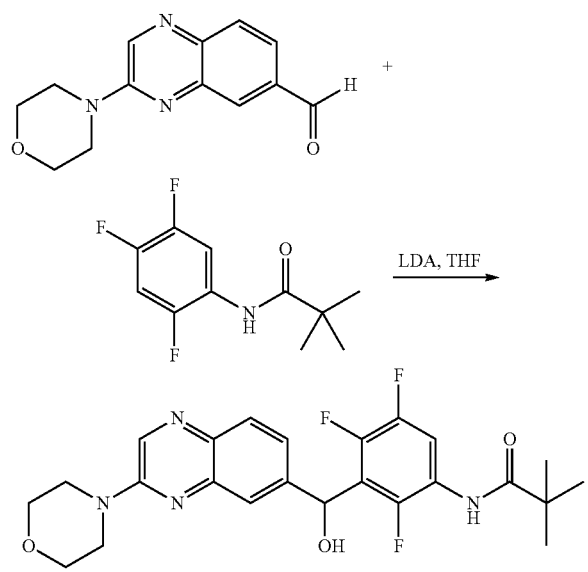

To a solution of N-(2,4,5-trifluorophenyl)pivalamide (550 mg, 2.4 mmol, 1.2 eq.) in THF (30 mL) cooled at −78° C.
was added LDA (4.1 mL, 4.8 mmol, 2.4 eq.) dropwise. The resulting mixture was stirred at −78° C. for 1 h, then a solution of 3-morpholinoquinoxaline-6-carbaldehyde (486 mg, 2.0 mmol, 1.0 eq.) in THF (20 mL) was added dropwise. The resulting mixture was stirred at −78° C. for 1 h, then quenched by the addition of NH₄Cl solution. The mixture was extracted with EA (20 mL×3) and the combined organic layers were dried over Na₂SO₄ and concentrated. The resulting residue was purified by flash column chromatography (MeOH/DCM=1/50, v/v) to afford N-(2,4,5-trifluoro-3-(hydroxy(3-morpholinoquinoxalin-6-yl)methyl)phenyl)pivalamide (620 mg, 65.2%).

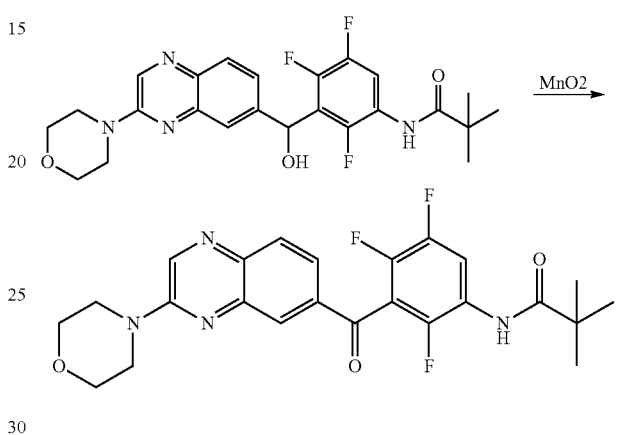

The solution of N-(2,4,5-trifluoro-3-(hydroxy(3-morpholinoquinoxalin-6-yl)methyl)phenyl)pivalamide (620 mg, 1.3 mmol, 1.0 eq.) in DCM (10 mL) was added MnO₂ (358 mg, 6.5 mmol, 5.0 eq.). The resulting mixture was stirred at 50° C. overnight, then cooled and filtered. The filtrate was concentrated and the residue was purified by flash column chromatography (PE/EA=1/2, v/v) to afford N-(2,4,5-trifluoro-3-(3-morpholinoquinoxaline-6-carbonyl)phenyl)pivalamide (560 mg, 90%).

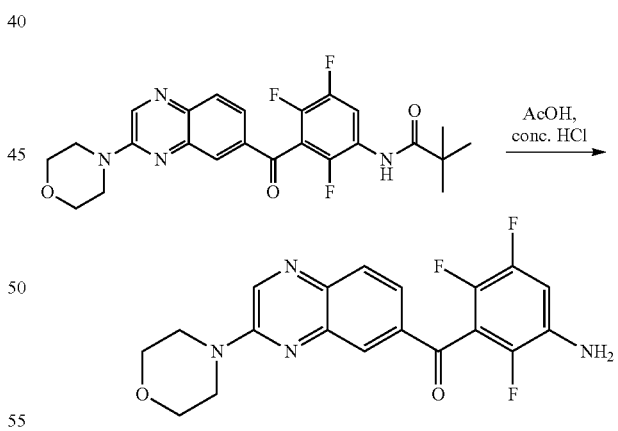

To a solution of N-(2,4,5-trifluoro-3-(3-morpholinoquinoxaline-6-carbonyl)phenyl)pivalamide (560 mg, 1.2 mmol, 1.0 eq.) in HOAc (10 mL) was added conc. HCl (50 mL). The mixture was stirred at 110° C. for 4 h, then poured onto ice. The mixture was adjusted to pH 10 by the addition of 1N NaOH solution, then extracted with DCM (100 mL×3). The combined organic layers were dried over Na₂SO₄ and concentrated. The resulting residue was purified by flash column chromatography (PE/EA=1/4, v/v) to afford (3-amino-2,5,6-trifluorophenyl)(3-morpholinoquinoxalin-6-yl)methanone as brown solid (410 mg, 88% yield).

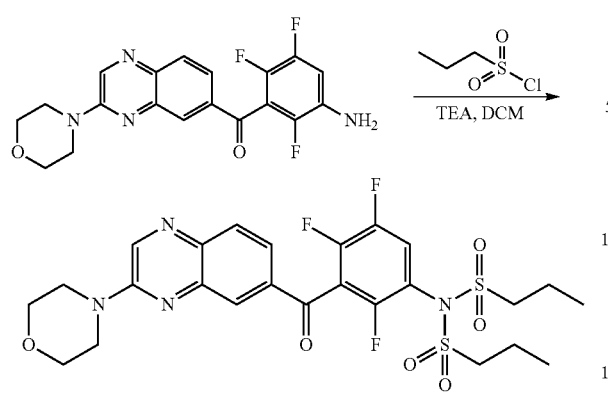 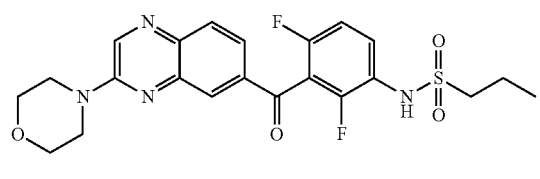 [SMILES: CCCS(=O)(=O)Nc1ccc(F)c(C(=O)c2ccc3ncc(N4CCOCC4)nc3c2)c1F]

To a solution of (3-amino-2,5,6-trifluorophenyl)(3-morpholinoquinoxalin-6-yl)methanone (40 mg, 0.1 mmol, 1.0 eq.) in DCM (10 mL) was added TEA (101 mg, 1 mol, 10 eq.) and propane-1-sulfonyl chloride (0.5 mL, 0.5 mmol, 5.0 eq.). The resulting mixture was stirred at rt for 1 h, then washed with water and extracted with DCM (10 mL×3). The combined organic layers were dried over Na2SO4, filtered and concentrated. The resulting residue was purified by flash column chromatography (PE/EA=2/1, v/v) to afford N-(propylsulfonyl)-N-(2,4,5-trifluoro-3-(3-morpholinoquinoxaline-6-carbonyl)phenyl)propane-1-sulfonamide (41 mg, 62.2%).

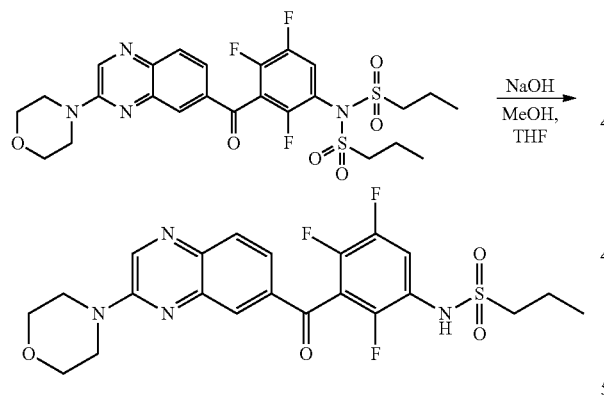 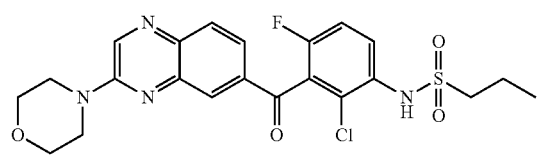 [SMILES: CCCS(=O)(=O)Nc1ccc(F)c(C(=O)c2ccc3ncc(N4CCOCC4)nc3c2)c1Cl]

To a solution of N-(propylsulfonyl)-N-(2,4,5-trifluoro-3-(3-morpholinoquinoxaline-6-carbonyl)phenyl)propane-1-sulfonamide (41 mg, 0.068 mmol, 1.0 eq.) in MeOH/THF (10 mL/10 mL) was added 1 N NaOH (0.15 mmol, 2.2 eq.). The resulting mixture was stirred at rt for 1 h, then concentrated. The resulting residue was purified by flash column chromatography (PE/EA=1/1, v/v) to afford N-(2,4,5-trifluoro-3-(3-morpholinoquinoxaline-6-carbonyl)phenyl)propane-1-sulfonamide (23 mg, 68.9%). LRMS (M+H$^+$) m/z calculated 495.1. found 495.1. $^1$H NMR (CDCl$_3$, 400 MHz) δ 8.67 (s, 1 H), 7.98-8.03 (m, 3 H), 7.66-7.73 (m, 1 H), 6.72 (s, 1 H), 3.78-3.88 (m, 8H), 3.12-3.16 (t, 2 H), 1.87-1.92 (q, 2 H), 1.05-1.09 (t, 3 H).

Example 7

Preparation of N-(2,4-difluoro-3-(3-morpholinoquinoxaline-6-carbonyl)phenyl)propane-1-sulfonamide N-(2,4-difluoro-3-(3-morpholinoquinoxaline-6-carbonyl)phenyl)propane-1-sulfonamide N-(2,4-difluoro-3-(3-morpholinoquinoxaline-6-carbonyl)phenyl)propane-1-sulfonamide was prepared as described for N-(2,4,5-trifluoro-3-(3-morpholinoquinoxaline-6-carbonyl)phenyl)propane-1-sulfonamide. LRMS (M+H$^+$) m/z calculated 477.1. found 477.0. $^1$H NMR (CDCl$_3$, 400 MHz) δ 9.85 (s, 1 H), 8.97 (s, 1 H), 8.03-8.01 (d, 1 H), 7.71-7.65 (d, 1 H), 7.67 (s, 1 H), 7.71-7.65 (m, 1 H), 7.38-7.33 (m, 1 H), 3.77-3.76 (m, 4 H), 3.73-3.72 (m, 4 H), 3.16-3.12 (m, 2 H), 1.76-1.70 (m, 2 H), 0.97-0.93 (t, 3 H).

Example 8

Preparation of N-(2-chloro-4-fluoro-3-(3-morpholinoquinoxaline-6-carbonyl)phenyl)propane-1-sulfonamide N-(2-chloro-4-fluoro-3-(3-morpholinoquinoxaline-6-carbonyl)phenyl)propane-1-sulfonamide N-(2-chloro-4-fluoro-3-(3-morpholinoquinoxaline-6-carbonyl)phenyl)propane-1-sulfonamide was prepared as described for N-(2,4,5-trifluoro-3-(3-morpholinoquinoxaline-6-carbonyl)phenyl)propane-1-sulfonamide. LRMS (M+H$^+$) m/z calculated 493.1. found 493.1. $^1$H NMR (DMSO-d6, 400 MHz) δ10.02 (s, 1 H), 8.94 (s, 1 H), 7.99-7.97 (d, 1 H), 7.86-7.84 (d, 1 H), 7.77 (s, 1 H), 7.45-7.41 (m, 1H), 6.91-6.87 (m, 1 H), 3.74-3.73 (m,8 H), 3.10-3.06 (m, 2 H), 1.76-1.70 (m, 2 H), 0.96-0.92 (t, 3 H).

Example 9

Preparation of N-(2,4,5-trifluoro-3-(3-morpholino-quinoxaline-6-carbonyl)phenyl)cyclopropanesulfonamide

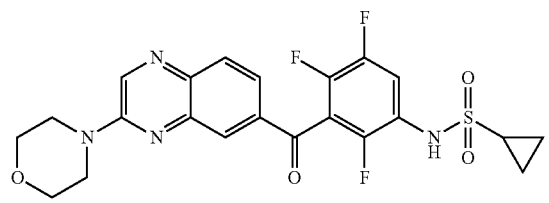 [SMILES: O=C(c1ccc2ncc(N3CCOCC3)nc2c1)c1c(F)c(F)cc(NS(=O)(=O)C2CC2)c1F]

N-(2,4,5-trifluoro-3-(3-morpholinoquinoxaline-6-carbonyl)phenyl)cyclopropanesulfonamide N-(2,4,5-trifluoro-3-(3-morpholinoquinoxaline-6-carbonyl)phenyl)cyclopropanesulfonamide was prepared as described for N-(2,4,5-trifluoro-3-(3-morpholinoquinoxaline-6-carbonyl)phenyl)propane-1-sulfonamide. LRMS (M+H$^+$) m/z calculated 491.1. found 490.8. $^1$H NMR (DMSO-d6, 400 MHz) δ 10.08 (brs, 1 H), 8.99 (s, 1 H), 8.04 (d, 1 H), 7.97 (s, 1 H), 7.89 (d, 1 H), 7.75 (m, 1 H), 3.87 (brs, 4 H), 3.74 (brs, 4 H), 2.80 (m, 1 H), 1.00 (m, 2 H), 0.98 (m, 2 H).

Example 10

Preparation of N-(2,4,5-trifluoro-3-(3-morpholino-quinoxaline-6-carbonyl)phenyl)benzenesulfonamide

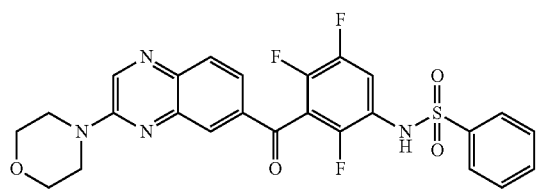 [SMILES: O=C(c1ccc2ncc(N3CCOCC3)nc2c1)c1c(F)c(F)cc(NS(=O)(=O)c2ccccc2)c1F]

N-(2,4,5-trifluoro-3-(3-morpholinoquinoxaline-6-carbonyl)phenyl)benzenesulfonamide N-(2,4,5-trifluoro-3-(3-morpholinoquinoxaline-6-carbonyl)phenyl)benzenesulfonamide was prepared as described for N-(2,4,5-trifluoro-3-(3-morpholinoquinoxaline-6-carbonyl)phenyl)propane-1-sulfonamide. LRMS (M+H$^+$) m/z calculated 529.1. found 529.1. $^1$H NMR (CDCl$_3$, 400 MHz) δ 10.61 (s, 1 H), 8.98 (s, 1 H), 7.99-7.97 (d, 1 H), 7.82 (s, 1 H), 7.77-7.72 (m, 3 H), 7.68-7.64 (m, 1 H), 7.60-7.58 (m, 3 H), 3.81-3.80 (m, 4 H), 3.76-3.75 (m, 4 H).

Example 11

Preparation of 4-methyl-N-(2,4,5-trifluoro-3-(3-morpholinoquinoxaline-6-carbonyl)phenyl)benzenesulfonamide

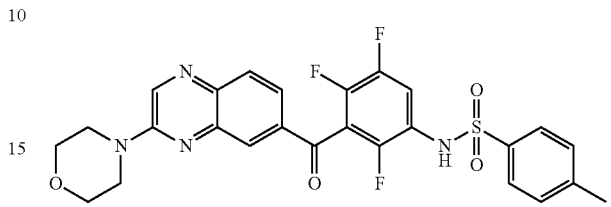

4-methyl-N-(2,4,5-trifluoro-3-(3-morpholinoquinoxaline-6-carbonyl)phenyl)benzenesulfonamide N-(2,4,5-trifluoro-3-(3-morpholinoquinoxaline-6-carbonyl)phenyl)benzenesulfonamide was prepared as described for N-(2,4,5-trifluoro-3-(3-morpholinoquinoxaline-6-carbonyl)phenyl)propane-1-sulfonamide. LRMS (M+H$^+$) m/z calculated 543.1. found 543.0. $^1$H NMR (CDCl$_3$, 400 MHz) δ 10.51 (s, 1 H), 8.99 (s, 1 H), 7.99-7.97 (d, 1 H), 7.85 (s, 1 H), 7.75-7.73 (m, 1 H), 7.65-7.63 (m, 3 H), 7.37-7.35 (d, 1 H), 4.05-4.00 (m, 4 H), 3.85-3.75 (m, 4 H), 2.50 (s, 1 H).

Example 12

Preparation of N-(2,4,5-trifluoro-3-(3-methylquinoxaline-6-carbonyl)phenyl)propane-1-sulfonamide

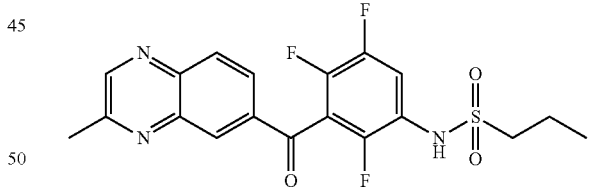

N-(2,4,5-trifluoro-3-(3-methylquinoxaline-6-carbonyl)phenyl)propane-1-sulfonamide N-(2,4,5-trifluoro-3-(3-methylquinoxaline-6-carbonyl)phenyl)propane-1-sulfonamide was prepared as described for N-(2,4,5-trifluoro-3-(3-morpholinoquinoxaline-6-carbonyl)phenyl)propane-1-sulfonamide. LRMS (M+H$^+$) m/z calculated 424.1. found 423.9. $^1$H NMR (DMSO-d6, 400 MHz) δ 10.13 (s, 1 H), 9.02 (s, 1 H), 8.54 (s, 1 H), 8.33 (d, 1 H), 8.20 (d, 1H,), 7.77 (m, 1 H), 2.78 (s, 3 H), 3.23 (m, 2 H), 1.75 (m, 2 H), 0.97 (s, 3 H).

Example 13

Preparation of N-(3-(3-chloroquinoxaline-6-carbonyl)-2,4,5-trifluorophenyl)propane-1-sulfonamide

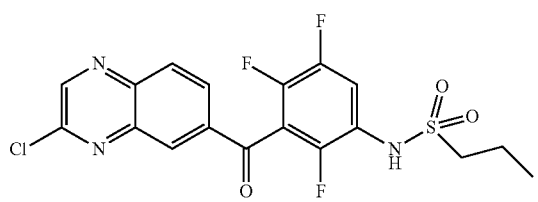 [SMILES: CCCS(=O)(=O)Nc1cc(F)c(F)c(C(=O)c2ccc3ncc(Cl)nc3c2)c1F]

N-(3-(3-chloroquinoxaline-6-carbonyl)-2,4,5-trifluorophenyl)propane-1-sulfonamide

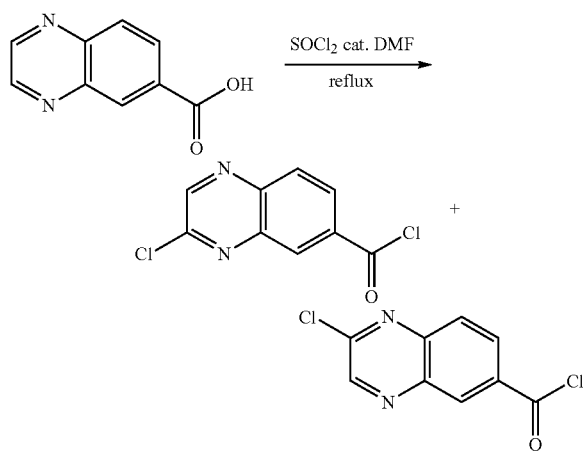

To a solution of quinoxaline-6-carboxylic acid (60 g, 0.34 mol) in SOCl$_2$ (300 mL) was added DMF (5 mL). The resulting mixture was heated under reflux overnight, then cooled and concentrated to afford crude mixture of 3-chloroquinoxaline-6-carbonyl chloride and 2-chloro-quinoxaline-6-carbonyl chloride (62 g, 94%).

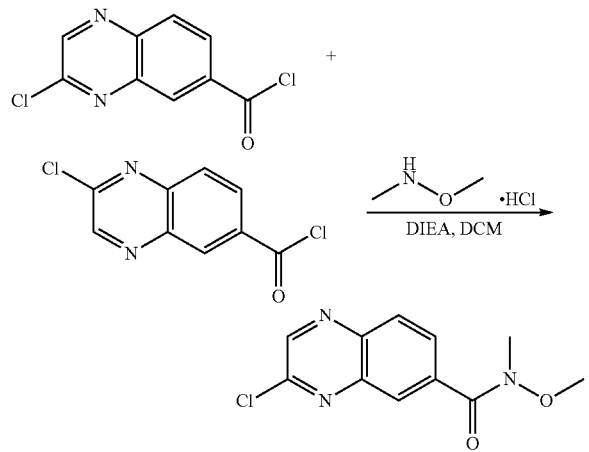

To a solution of O,N-dimethyl-hydroxylamine hydrochloride salt (29 g, 0.30 mol, 1.1 eq) and DIEA (182 mL, 1.08 mol, 4.0 eq) in DCM (300 mL) was added the mixture of 3-chloro-quinoxaline-6-carbonyl chloride and 2-chloro-quinoxaline-6-carbonyl chloride (52 g, 0.27 mol, 1.0 eq) at 0° C. The mixture was stirred at rt overnight, then concentrated. The resulting residue was washed with water (300 mL×2) and extracted with EA (300 mL×2). The combined organic layers were dried over anhydrous Na$_2$SO$_4$, filtered and concentrated. The resulting solid was triturated with EA/PE=1/1 (300 mL) to afford 3-chloro-N-methoxy-N-methylquinoxaline-6-carboxamide (16.5 g, 24.3%).

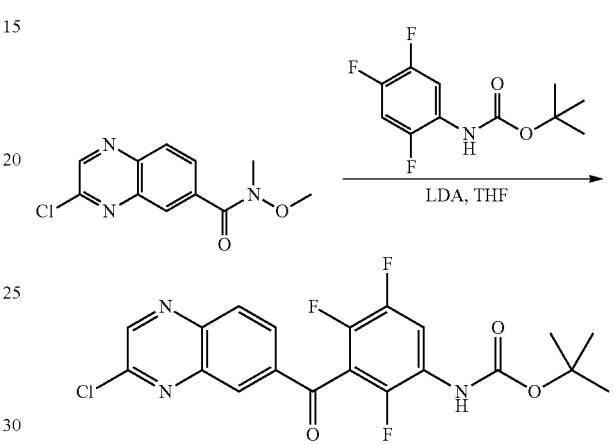

To a solution of N-(2,4,5-trifluorophenyl)pivalamide (9 g, 36.4 mmol, 1.2 eq.) in THF (250 mL) cooled at −78° C. was added LDA (36.4 mL, 72.8 mmol, 2.4 eq.) dropwise. The resulting mixture was stirred at −78° C. for 30 min, then a solution of 3-chloro-N-methoxy-N-methylquinoxaline-6-carboxamide (7.51 g, 29.9 mmol, 1.0 eq.) in THF (100 mL) was added dropwise. The resulting mixture was stirred at −78° C. for 1 h, then quenched by the addition of NH4Cl solution. The mixture was extracted with EA (100 mL×3). The combined organic layers were dried over Na$_2$SO$_4$, filtered and concentrated. The resulting residue was purified by flash column chromatography (PE/EA=4/1, v/v) to afford tert-butyl (3-(3-chloroquinoxaline-6-carbonyl)-2,4,5-trifluorophenyl)carbamate (755 mg, 5.8%).

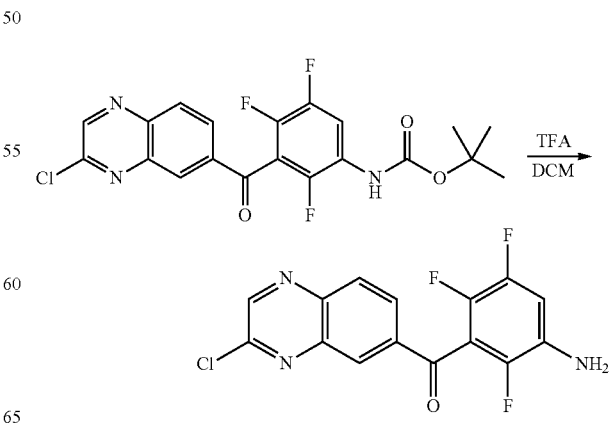

To a solution of tert-butyl (3-(3-chloroquinoxaline-6-carbonyl)-2,4,5-trifluorophenyl)carbamate (128 mg, 0.29 mmol, 1.0 eq.) in DCM (5 mL) was added TFA (5 mL). After the resulting mixture was stirred at rt for 0.5 h, the solvent was evaporated. The resulting residue was washed with saturated NaHCO₃ and extracted with EA (20 mL×3). The combined organic layers were dried over MgSO₄, filtered and concentrated. The resulting residue was purified by flash column chromatography (PE/EA=2/1, v/v) to afford (3-amino-2,5,6-trifluorophenyl)(3-chloroquinoxalin-6-yl)methanone (40 mg, 40.9%).

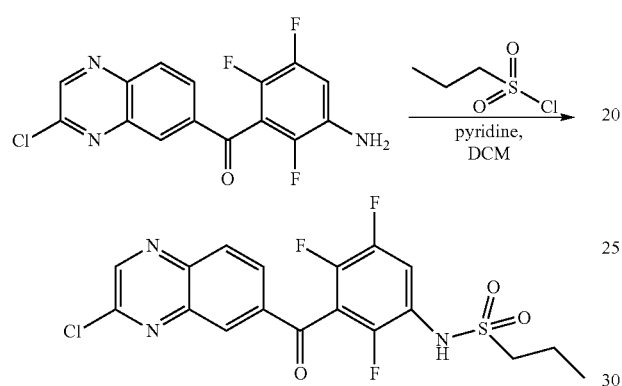

To a solution of (3-amino-2,5,6-trifluorophenyl)(3-chloroquinoxalin-6-yl)methanone (40 mg, 0.119 mmol, 1.0 eq.) in DCM (5 mL) was added propane-1-sulfonyl chloride (84.6 mg, 0.593 mmol, 5.0 eq.) and pyridine (94 mg, 1.19 mmol, 10.0 eq.). The mixture was heated under reflux overnight, then concentrated. The resulting residue was purified by flash column chromatography (PE/EA=4/1, v/v) and Prep-TLC to afford N-(3-(3-chloroquinoxaline-6-carbonyl)-2,4,5-trifluorophenyl)propane-1-sulfonamide (8 mg, 15.2%). LRMS (M–H⁻) m/z calculated 442.0. found 442.0. ¹H NMR (CDCl₃, 400 MHz) δ 8.91 (s, 1 H), 8.27-8.41 (m, 3 H), 7.71-7.77 (m, 1 H), 6.63 (s, 1 H), 3.13-3.17 (t, 2 H), 1.86-1.94 (q, 2 H), 1.07-1.11 (t, 3 H).

Example 14

Preparation of N-(3-(3-(4-chlorophenyl)quinoxaline-6-carbonyl)-2,4,5-trifluorophenyl)propane-1-sulfonamide

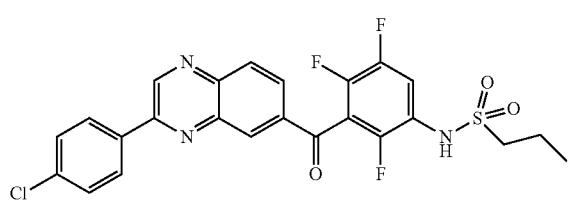 [SMILES: CCCS(=O)(=O)Nc1cc(F)c(F)c(C(=O)c2ccc3ncc(-c4ccc(Cl)cc4)nc3c2)c1F]

N-(3-(3-(4-chlorophenyl)quinoxaline-6-carbonyl)-2,4,5-trifluorophenyl)propane-1-sulfonamide A mixture of 3-chloro-N-methoxy-N-methylquinoxaline-6-carboxamide (5 g, 0.02 mol, 1.0 eq.), (4-chlorophenyl)boronic acid (3.43 g, 0.022 mol, 1.1 eq.) Pd(dppf)2Cl2 (816 mg, 0.001 mol, 0.05 eq.) and Na2CO3 (4.24 g, 0.04 mol, 2.0 eq.) in dioxane and water (90 mL/10 mL) was heated at 80° C. for 4 hs under N2 protection, then cooled and concentrated. The resulting residue was purified by flash column chromatography (PE/EA=4/1, v/v) to afford 3-(4-chlorophenyl)-N-methoxy-N-methylquinoxaline-6-carboxamide (4 g, 61.0%).

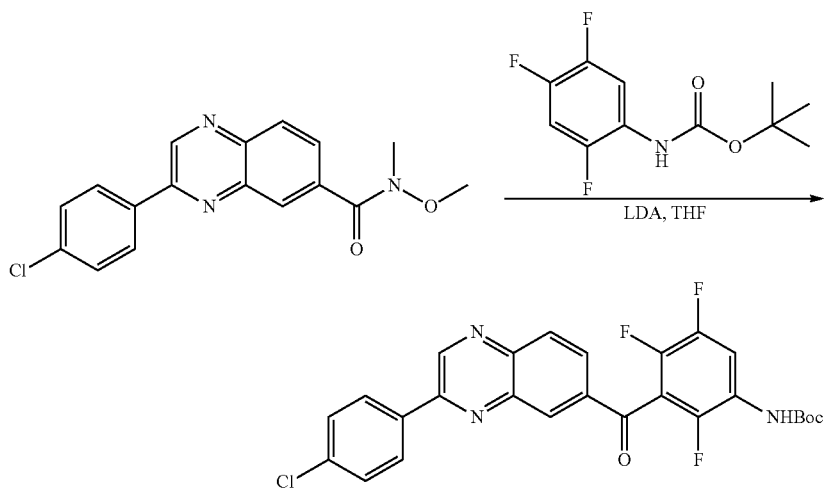

To a solution of N-(2,4,5-trifluorophenyl)pivalamide (2.96 g, 12 mmol, 1.2 eq.) in THF (100 mL) cooled at −78° C. was added LDA (12 mL, 24 mmol, 2.4 eq.) dropwise. The resulting mixture was stirred at −78° C. for 30 min, then a solution of 3-(4-chlorophenyl)-N-methoxy-N-methylquinoxaline-6-carboxamide (3.28 g, 10 mmol, 1.0 eq.) in THF (50 mL) was added dropwise. The resulting mixture was stirred at −78° C. for 1 h, then quenched by the addition of NH$_4$Cl solution. The mixture was extracted with EA (100 mL×3). The combined organic layers were dried over Na$_2$SO$_4$, filtered and concentrated. The resulting residue was purified by flash column chromatography (PE/EA=4/1, v/v) to afford tert-butyl (3-(3-(4-chlorophenyl)quinoxaline-6-carbonyl)-2,4,5-trifluorophenyl)carbamate (440 mg, 8.6%).

-continued

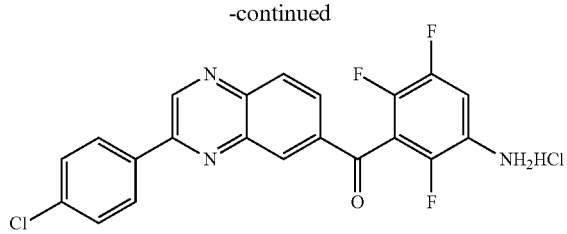

A solution of tert-butyl (3-(3-(4-chlorophenyl)quinoxaline-6-carbonyl)-2,4,5-trifluorophenyl)carbamate (440 mg, 0.86 mmol, 1.0 eq.) in 6 N HCl/dioxane (10 mL) was stirred at rt for 3 h, then concentrated and the resulting solid was used in the next step without further purification.

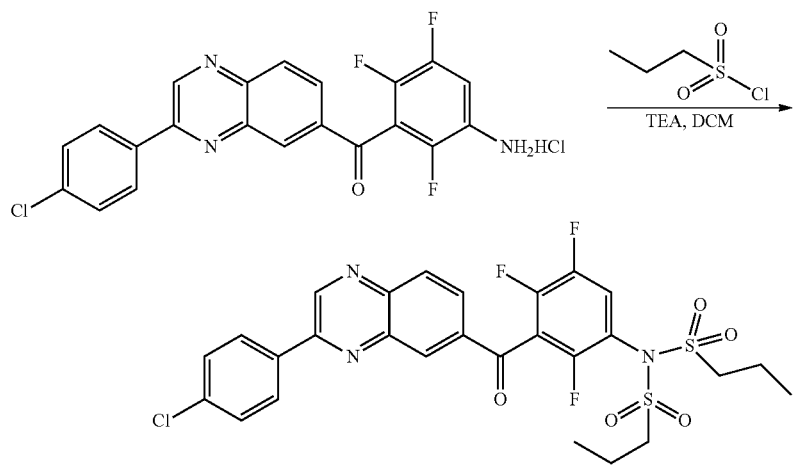

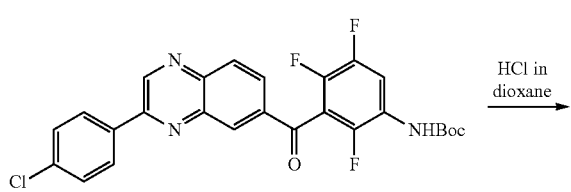

To a solution of (3-amino-2,5,6-trifluorophenyl)(3-(4-chlorophenyl)quinoxalin-6-yl)methanone hydrochloride (100 mg, 0.24 mmol, 1.0 eq.) in DCM (10 mL) were added TEA (242 mg, 2.4 mmol, 10.0 eq.) and propane-1-sulfonyl chloride (172 mg, 1.2 mmol, 5.0 eq.). The resulting mixture was stirred at rt for 1 h, then concentrated. The resulting residue was dissolved in EA (10 mL) and washed with saturated NaHCO$_3$ solution, dried over anhydrous Na$_2$SO$_4$, filtered and concentrated. The resulting residue was purified by flash column chromatography (PE/EA=4/1, v/v) to afford N-(3-(3-(4-chlorophenyl)quinoxaline-6-carbonyl)-2,4,5-trifluorophenyl)-N-(propylsulfonyl)propane-1-sulfonamide (50 mg, 40.3%).

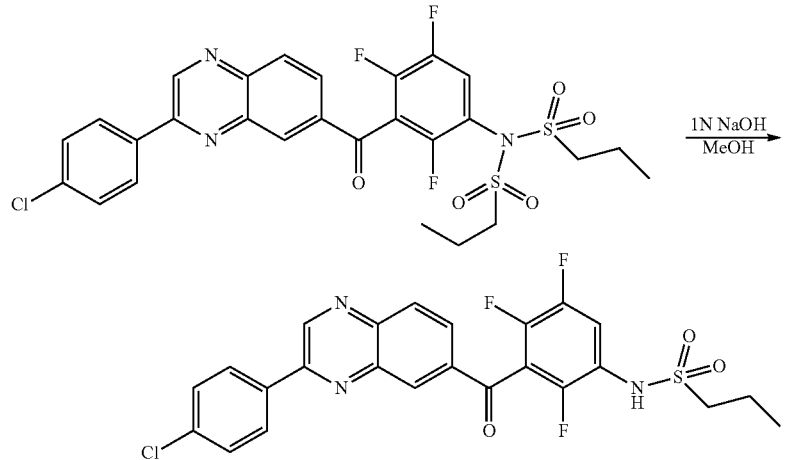

To a N-(3-(3-(4-chlorophenyl)quinoxaline-6-carbonyl)-2,4,5-trifluorophenyl)-N-(propylsulfonyl)propane-1-sulfonamide (50 mg, 0.08 mmol, 1.0 eq.) in MeOH (5 mL) was added NaOH aqueous solution (1 N, 0.16 mL, 0.16 mmol, 2.0 eq.). The resulting mixture was stirred at rt for 1 h, then concentrated. The resulting residue was purified by flash column chromatography (PE/EA=2/1, v/v) to afford N-(3-(3-(4-chlorophenyl)quinoxaline-6-carbonyl)-2,4,5-trifluorophenyl)propane-1-sulfonamide (25 mg, 60.2%). LRMS (M−H$^+$) m/z calculated 518.1. found 518.0. $^1$H NMR (CDCl$_3$, 400 MHz) δ 9.42 s,), 8.44 (s, 1 H), 8.27-8.38 (m, 2 H), 8.14-8.16 (dd, 2 H), 7.73-7.76 (m, 1 H), 7.55-7.57 (dd, 2 H), 6.55 (s, 1 H), 3.14-3.18 (m, 2H), 1.88-1.94 (q, 2 H), 1.06-1.10 (t, 3 H).

Example 15

Preparation of N-(3-(3-(4-chlorophenyl)quinoxaline-6-carbonyl)-2,4-difluorophenyl)propane-1-sulfonamide N-(3-(3-(4-chlorophenyl)quinoxaline-6-carbonyl)-2,4-difluorophenyl)propane-1-sulfonamide N-(3-(3-(4-chlorophenyl)quinoxaline-6-carbonyl)-2,4-difluorophenyl)propane-1-sulfonamide was prepared as described for N-(3-(3-(4-chlorophenyl)quinoxaline-6-carbonyl)-2,4,5-trifluorophenyl)propane-1-sulfonamide. LRMS (M+H$^+$) m/z calculated 501.9. found 501.8. $^1$H NMR (CDCl$_3$, 400 MHz) δ 9.41 (s, 1 H), 8.44 (m, 1 H), 8.35-8.38 (m, 1 H), 8.25-8.27 (m, 1 H), 8.13-8.16 (m, 2 H), 7.80-7.83 (m, 1 H), 7.54-7.57 (m, 2 H), 7.09-7.13 (m, 1 H), 6.58 (m, 1 H), 3.11-3.15 (m, 2 H), 1.87-1.93 (m, 2 H), 1.04-1.28 (t, 3 H).

Example 16

Preparation of N-(2,4,5-trifluoro-3-(3-(2-methyl-1H-imidazol-1-yl)quinoxaline-6-carbonyl)phenyl)propane-1-sulfonamide N-(2,4,5-trifluoro-3-(3-(2-methyl-1H-imidazol-1-yl)quinoxaline-6-carbonyl)phenyl)propane-1-sulfonamide

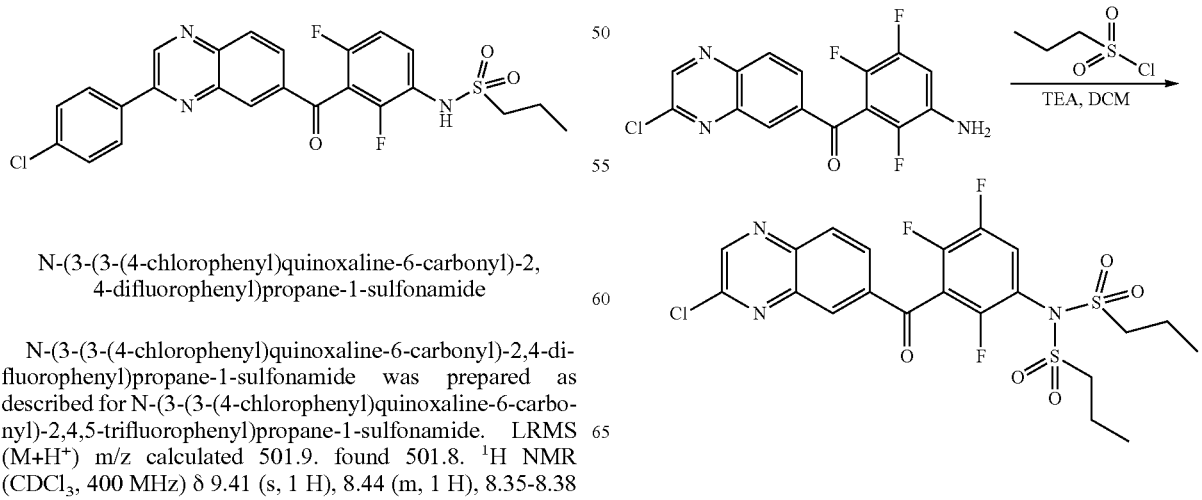

To a solution of (3-amino-2,5,6-trifluorophenyl)(3-chloroquinoxalin-6-yl)methanone (700 mg, 2.0 mmol, 1 eq.) in DCM (35 mL) was added TEA (5.6 mL, 400 mmol, 22 eq.) and propane-1-sulfonyl chloride (2.1 mL, 20 mmol, 10 eq.). The resulting mixture was stirred at rt for 1 h, washed with water and extracted with DCM (20 mL×3). The combined organic layers were dried over Na₂SO₄, filtered and concentrated. The resulting residue was purified by flash column chromatography (PE/EA=2/1, v/v) to afford N-(3-(3-chloroquinoxaline-6-carbonyl)-2,4,5-trifluorophenyl)-N-(propylsulfonyl)propane-1-sulfonamide (980 mg, 90%).

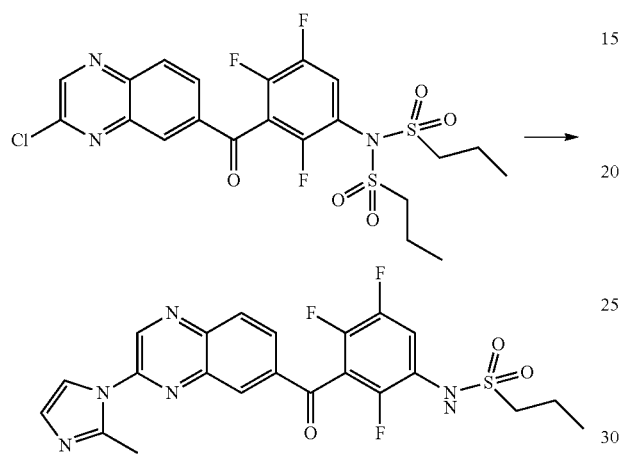

To a solution of N-(3-(3-chloroquinoxaline-6-carbonyl)-2,4,5-trifluorophenyl)-N-(propylsulfonyl)propane-1-sulfonamide (50 mg, 9.6 mmol, 1.0 eq.) in DMF (2 mL) was added 2-methyl-1H-imidazole (18 mg, 24 mmol, 2.5 eq.) and Cs2CO3 (59 mg, 19.2 mmol, 2.0 eq.). The resulting mixture was stirred at 90° C. for 4 h, then washed with water and extracted with EA (20 mL×3). The combined organic phase was dried over Na2SO4, filtered and concentrated. The resulting residue was purified by flash column chromatography (DCM/MeOH=30/1, v/v) to afford N-(2,4,5-trifluoro-3-(3-(2-methyl-1H-imidazol-1-yl)quinoxaline-6-carbonyl)phenyl)propane-1-sulfonamide (34 mg, 73%). LRMS (M+H⁺) m/z calculated 490.1. found 489.9. ¹H NMR (DMSO, 400 MHz) δ 10.13 (brs, 1 H), 9.46 (s, 1 H), 8.56 (s, 1 H), 7.95 (s, 1 H), 8.36 (brs, 2 H), 7.77 (m, 1 H), 7.94 (s, 1 H), 2.69 (s, 3 H), 3.21 (m, 2 H), 1.75 (m, 2 H), 0.97 (s, 3 H).

Example 17

Preparation of N-(2,4,5-trifluoro-3-(3-(4-methyl-1H-imidazol-1-yl)quinoxaline-6-carbonyl)phenyl)propane-1-sulfonamide

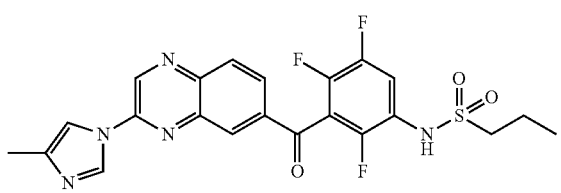 [SMILES: CCCS(=O)(=O)Nc1cc(F)c(F)c(C(=O)c2ccc3ncc(-n4cnc(C)c4)nc3c2)c1F]

N-(2,4,5-trifluoro-3-(3-(4-methyl-1H-imidazol-1-yl)quinoxaline-6-carbonyl)phenyl)propane-1-sulfonamide N-(2,4,5-trifluoro-3-(3-(4-methyl-1H-imidazol-1-yl)quinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 490.1. found 490.0. ¹H NMR (DMSO-d6, 400 MHz) δ 10.15 (s, 1 H), 9.64 (s, 1 H), 8.75 (s, 1 H), 8.46 (s, 1 H), 8.36 (brs, 2 H), 7.79 (m, 1 H), 7.94 (s, 1 H), 2.22 (s, 3 H), 3.21 (m, 2 H), 1.75 (m, 2H), 0.97 (s, 3 H).

Example 18

Preparation of N-(3-(3-(1H-imidazol-1-yl)quinoxaline-6-carbonyl)-2,4,5-trifluorophenyl)propane-1-sulfonamide

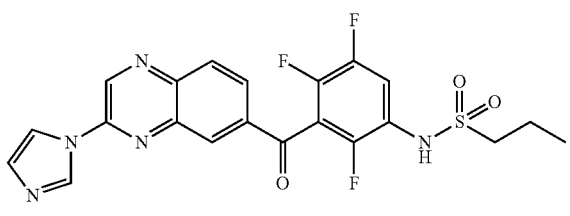 [SMILES: CCCS(=O)(=O)Nc1cc(F)c(F)c(C(=O)c2ccc3ncc(-n4ccnc4)nc3c2)c1F]

N-(3-(3-(1H-imidazol-1-yl)quinoxaline-6-carbonyl)-2,4,5-trifluorophenyl)propane-1-sulfonamide N-(3-(3-(1H-imidazol-1-yl)quinoxaline-6-carbonyl)-2,4,5-trifluorophenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 476.1. found 475.9. ¹H NMR (DMSO-d6, 400 MHz) δ 10.16 (brs, 1 H), 9.71 (s, 1 H), 8.87 (s, 1 H), 8.52 (s, 1 H), 8.35 (brs, 2 H), 8.21 (s, 1 H), 7.77 (m, 1 H), 7.26 (s, 1 H), 2.69 (s, 3 H), 3.24 (m, 2 H), 1.72 (m, 2 H), 0.97 (s, 3 H).

Example 19

Preparation of N-(2,4,5-trifluoro-3-(3-(5-methyl-1H-imidazol-1-yl)quinoxaline-6-carbonyl)phenyl)propane-1-sulfonamide

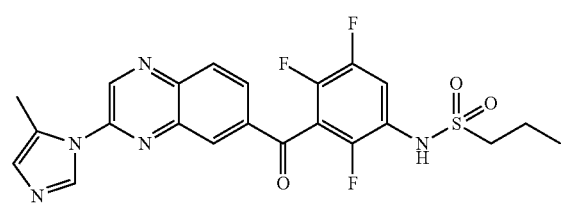 [SMILES: CCCS(=O)(=O)Nc1cc(F)c(F)c(C(=O)c2ccc3ncc(-n4cncc4C)nc3c2)c1F]

N-(2,4,5-trifluoro-3-(3-(5-methyl-1H-imidazol-1-yl)quinoxaline-6-carbonyl)phenyl)propane-1-sulfonamide N-(2,4,5-trifluoro-3-(3-(5-methyl-1H-imidazol-1-yl)quinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 490.1. found 490.0. ¹H NMR (DMSO-d6, 400 MHz) δ 8.99 (s, 1 H), 8.75 (d, 1 H), 7.92 (brs, 2 H), 7.57 (m, 1 H), 3.87 (brs, 4 H), 3.03 (brs, 4 H), 2.95 (t, 2 H), 1.68 (m, 2 H), 0.93 (t, 3 H).

Example 20

Preparation of N-(2,4,5-trifluoro-3-(3-(piperazin-1-yl)quinoxaline-6-carbonyl)phenyl)propane-1-sulfonamide

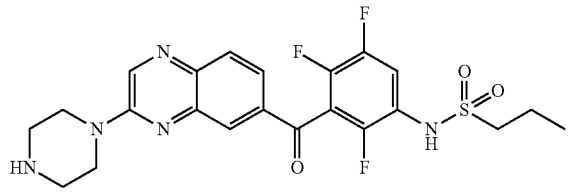 [SMILES: CCCS(=O)(=O)Nc1cc(F)c(F)c(C(=O)c2ccc3ncc(N4CCNCC4)nc3c2)c1F]

N-(2,4,5-trifluoro-3-(3-(piperazin-1-yl)quinoxaline-6-carbonyl)phenyl)propane-1-sulfonamide N-(2,4,5-trifluoro-3-(3-(piperazin-1-yl)quinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 494.1. found 494.0. ¹H NMR (DMSO-d6, 400 MHz) δ 8.99 (s, 1 H), 8.75 (d, 1 H), 7.92 (brs, 2 H), 7.57 (m, 1 H), 3.87 (brs, 4 H), 3.03 (brs, 4 H), 2.95 (t, 2 H), 1.68 (m, 2H), 0.93 (t, 3 H).

Example 21

Preparation of N-(2,4,5-trifluoro-3-(3-(2-oxopiperazin-1-yl)quinoxaline-6-carbonyl)phenyl)propane-1-sulfonamide

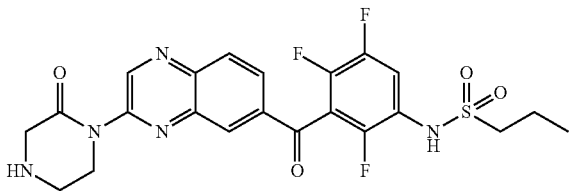 [SMILES: CCCS(=O)(=O)Nc1cc(F)c(F)c(C(=O)c2ccc3ncc(N4CCNCC4=O)nc3c2)c1F]

N-(2,4,5-trifluoro-3-(3-(2-oxopiperazin-1-yl)quinoxaline-6-carbonyl)phenyl)propane-1-sulfonamide N-(2,4,5-trifluoro-3-(3-(2-oxopiperazin-1-yl)quinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 508.1. found 508.0. ¹H NMR (DMSO-d6, 400 MHz) δ 9.51 (s, 1 H), 8.39 (s, 1 H), 8.26 (brs, 2 H), 7.74 (m, 1 H), 5.75 (brs, 1 H), 3.99 (brs, 2 H), 3.61 (s, 2 H), 3.12 (brs, 2 H), 3.21 (t, 2 H), 1.72 (m, 2 H), 0.96 (t, 3 H).

Example 22

Preparation of N-(2,4,5-trifluoro-3-(3-(3-oxopiperazin-1-yl)quinoxaline-6-carbonyl)phenyl)propane-1-sulfonamide

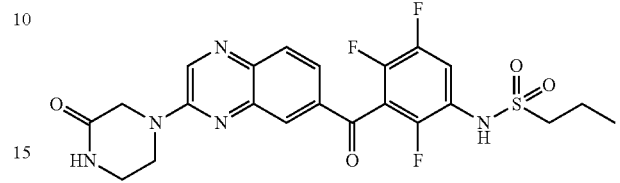

N-(2,4,5-trifluoro-3-(3-(3-oxopiperazin-1-yl)quinoxaline-6-carbonyl)phenyl)propane-1-sulfonamide N-(2,4,5-trifluoro-3-(3-(3-oxopiperazin-1-yl)quinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 508.1. found 508.0. ¹H NMR (DMSO-d6, 400 MHz) δ 10.10 (brs, 1 H), 8.96 (s, 1 H), 8.22 (s, 1 H), 8.02 (brs, 2 H), 7.91 (d, 1 H), 7.74 (m, 1 H), 4.31 (s, 2 H), 3.99 (brs, 2 H), 3.60 (brs, 2 H), 3.19 (t, 2 H), 1.75 (m, 2 H), 0.96 (t, 3 H).

Example 23

Preparation of N-(3-(3-(diethylamino)quinoxaline-6-carbonyl)-2,4,5-trifluorophenyl)propane-1-sulfonamide

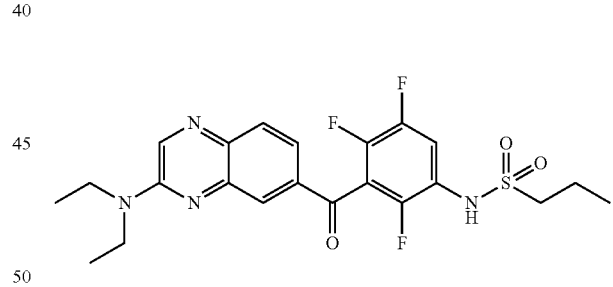

N-(3-(3-(diethylamino)quinoxaline-6-carbonyl)-2,4,5-trifluorophenyl)propane-1-sulfonamide N-(3-(3-(diethylamino)quinoxaline-6-carbonyl)-2,4,5-trifluorophenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H⁺) m/z calculated 481.1. found 480.0. ¹H NMR (DMSO-d6, 400 MHz) δ 8.53 (s, 1 H), 7.98 (s, 1 H), 7.94 (d, 1 H), 7.88 (d, 1 H), 7.68 (m, 1 H), 6.57 (brs, 1 H), 3.70 (m, 4 H), 1.28 (m, 6 H), 3.14 (t, 2 H), 1.89 (m, 2 H), 1.07 (t, 3 H).

Example 24

Preparation of N-(2,4,5-trifluoro-3-(3-(3-(hydroxymethyl)morpholino)quinoxaline-6-carbonyl)phenyl)propane-1-sulfonamide

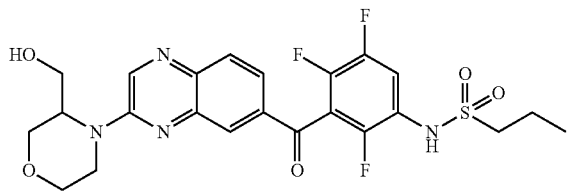 [SMILES: CCCS(=O)(=O)Nc1cc(F)c(F)c(C(=O)c2ccc3ncc(N4CCOCC4CO)nc3c2)c1F]

N-(2,4,5-trifluoro-3-(3-(3-(hydroxymethyl)morpholino)quinoxaline-6-carbonyl)phenyl)propane-1-sulfonamide N-(2,4,5-trifluoro-3-(3-(3-(hydroxymethyl)morpholino)quinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H$^+$) m/z calculated 525.1. found 525.1. $^1$H NMR (CDCl$_3$, 400 MHz) δ 10.06 (s, 1 H), 8.93 (s, 1 H), 8.00-7.97 (d, 1 H), 7.93 (m, 1 H), 7.88-7.86 (d, 1 H), 7.74-7.72 (m, 1 H), 4.87-4.90 (m, 1 H), 4.52 (m, 1 H), 4.33-4.30 (d, 1 H), 3.98-3.96 (m, 2 H), 3.72-3.70 (m, 2 H), 3.60 (d, 1 H), 3.60 (t, 1 H), 3.20-3.16 (m, 6 H), 1.98 (m, 1 H), 1.75-1.70 (m, 3 H), 0.98-0.94 (t, 3 H).

Example 25

Preparation of N-(3-(3-((2-(dimethylamino)ethyl)(methyl)amino)quinoxaline-6-carbonyl)-2,4,5-trifluorophenyl)propane-1-sulfonamide

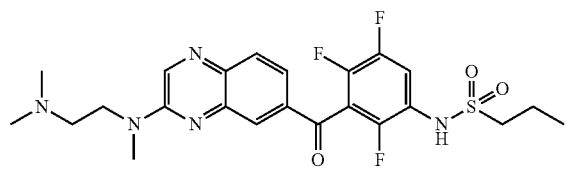 [SMILES: CCCS(=O)(=O)Nc1cc(F)c(F)c(C(=O)c2ccc3ncc(N(C)CCN(C)C)nc3c2)c1F]

N-(3-(3-((2-(dimethylamino)ethyl)(methyl)amino)quinoxaline-6-carbonyl)-2,4,5-trifluorophenyl)propane-1-sulfonamide N-(3-(3-((2-(dimethylamino)ethyl)(methyl)amino)quinoxaline-6-carbonyl)-2,4,5-trifluorophenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M+H$^+$) m/z calculated 510.5. found 510.2. $^1$H NMR (CDCl$_3$, 400 MHz) δ 8.62 (s, 1 H), 7.88-7.99 (m, 3 H), 7.62-7.64 (m, 1 H), 3.94-3.97 (t, 2 H), 3.32 (s, 3 H), 3.11-3.14 (m, 2 H), 2.84-2.87 (t, 2 H), 2.51 (s, 6 H), 1.85-1.91 (m, 2 H), 1.03-1.07 (t, 3 H).

Example 26

Preparation of N-(2,4,5-trifluoro-3-(3-(2-methoxyethoxy)quinoxaline-6-carbonyl)phenyl)propane-1-sulfonamide

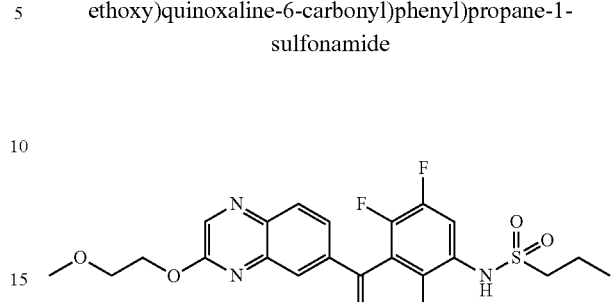

N-(2,4,5-trifluoro-3-(3-(2-methoxyethoxy)quinoxaline-6-carbonyl)phenyl)propane-1-sulfonamide

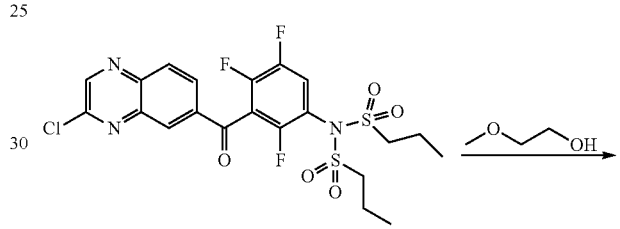

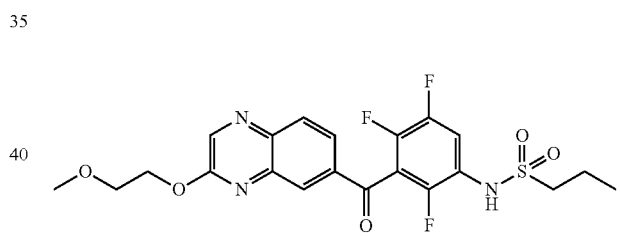

To a solution of N-(3-(3-chloroquinoxaline-6-carbonyl)-2,4,5-trifluorophenyl)-N-(propylsulfonyl)propane-1-sulfonamide (50 mg, 9.6 mmol, 1.0 eq.) in DMF (2 mL) was added 2-methoxyethanol (17.5 mg, 24 mmol, 2.5 eq.) and Cs$_2$CO$_3$ (87 mg, 24 mmol, 2.0 eq.). The resulting mixture was stirred at 90° C. for 7.5 h, then cooled, washed with water and extracted with EA (20 mL×3). The combined organic phase was dried over Na2SO4, filtered and concentrated. The resulting residue was purified by flash column chromatography (PE/EA=4/1, v/v) to afford N-(2,4,5-trifluoro-3-(3-(2-methoxyethoxy)quinoxaline-6-carbonyl)phenyl)propane-1-sulfonamide (28 mg, 61%). LRMS (M+H$^+$) m/z calculated 484.1. found 483.9. $^1$H NMR (DMSO-d6, 400 MHz) δ10.12 (s, 1 H), 8.81 (s, 1H), 8.26 (s, 1 H), 8.22 (d, 1 H), 8.15 (d, 1 H), 7.79 (m, 1 H), 4.58 (brs, 2 H), 3.75 (brs, 2 H), 3.33 (s, 3H), 3.23 (m, 2 H), 1.75 (m, 2 H), 0.97 (s, 3 H).

Example 27

N-(2,4,5-trifluoro-3-(3-methoxyquinoxaline-6-carbonyl)phenyl)propane-1-sulfonamide

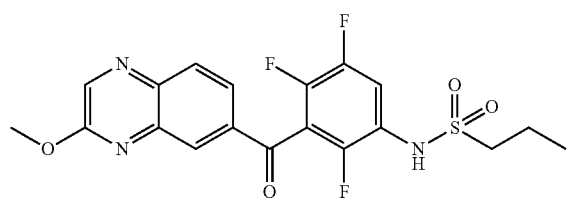 [SMILES: CCCS(=O)(=O)Nc1cc(F)c(F)c(C(=O)c2ccc3ncc(OC)nc3c2)c1F]

N-(2,4,5-trifluoro-3-(3-methoxyquinoxaline-6-carbonyl)phenyl)propane-1-sulfonamide N-(2,4,5-trifluoro-3-(3-methoxyquinoxaline-6-carbonyl)phenyl)propane-1-sulfonamide (58 mg, 65%) was prepared as described for N-(2,4,5-trifluoro-3-(3-(2-methoxyethoxy)quinoxaline-6-carbonyl)phenyl)propane-1-sulfonamide. LRMS (M–H$^+$) m/z calculated 438.1. found 437.8. $^1$H NMR (DMSO-d6, 400 MHz) δ 10.15 (s, 1 H), 8.78 (s, 1 H), 8.28 (s, 1 H), 8.21 (d, 1 H), 8.15 (d, 1 H), 7.77 (m, 1 H), 4.06 (s, 3 H), 3.24 (m, 2 H), 1.73 (m, 2 H), 0.97 (s, 3 H).

Example 28

Preparation of N-(2,4-difluoro-3-(3-methoxyquinoxaline-6-carbonyl)phenyl)propane-1-sulfonamide

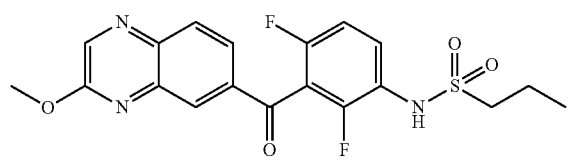 [SMILES: CCCS(=O)(=O)Nc1ccc(F)c(C(=O)c2ccc3ncc(OC)nc3c2)c1F]

N-(2,4-difluoro-3-(3-methoxyquinoxaline-6-carbonyl)phenyl)propane-1-sulfonamide

N-(2,4-difluoro-3-(3-methoxyquinoxaline-6-carbonyl)phenyl)propane-1-sulfonamide was prepared as described for N-(2,4,5-trifluoro-3-(3-(2-methoxyethoxy)quinoxaline-6-carbonyl)phenyl)propane-1-sulfonamide. LRMS (M–H$^+$) m/z calculated 420.4. found 420.0. $^1$H NMR (CDCl$_3$, 400 MHz) δ 8.58 (s, 1 H), 8.15-8.18 (m, 3 H), 7.76-7.82 (m, 1 H), 7.07-7.11 (m, 1 H), 6.49 (s, 1 H), 4.11 (s, 3 H), 3.10-3.14 (m, 2 H), 1.85-1.94 (m, 2 H), 0.86-0.90 (t, 3 H).

Example 29

Preparation of N-(2,4,5-trifluoro-3-(3-fluoroquinoxaline-6-carbonyl)phenyl)propane-1-sulfonamide

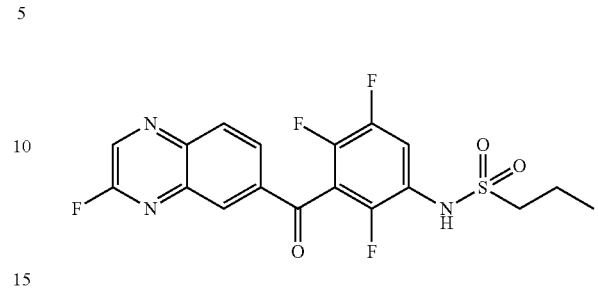

N-(2,4,5-trifluoro-3-(3-fluoroquinoxaline-6-carbonyl)phenyl)propane-1-sulfonamide N-(2,4,5-trifluoro-3-(3-fluoroquinoxaline-6-carbonyl)phenyl)propane-1-sulfonamide was prepared as described for N-(2,4,5-trifluoro-3-(3-(2-methyl-1H-imidazol-1-yl)quinoxaline-6-carbonyl)phenyl)propane-1-sulfonamide. LRMS (M–H$^+$) m/z calculated 426.1. found 425.9. $^1$H NMR (DMSO-d6, 400 MHz) δ 10.11 (brs, 1 H), 9.16 (d, 1 H), 8.50 (s, 1 H), 8.37 (m, 2 H), 7.79 (m, 1 H), 3.22 (t, 2 H), 1.72 (m, 2 H), 0.95 (t, 3 H).

Example 30

Preparation of N-(2,4,5-trifluoro-3-(3-phenylquinoxaline-6-carbonyl)phenyl)propane-1-sulfonamide

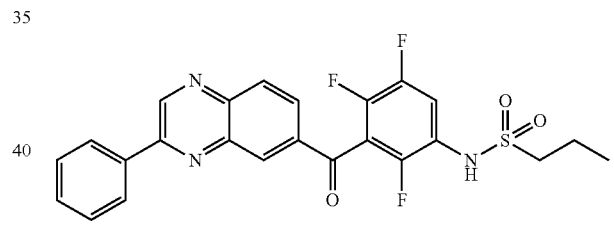

N-(2,4,5-trifluoro-3-(3-phenylquinoxaline-6-carbonyl)phenyl)propane-1-sulfonamide

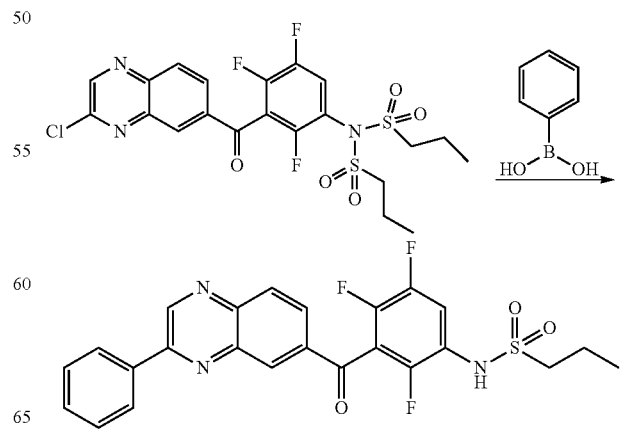

A mixture of N-(3-(3-chloroquinoxaline-6-carbonyl)-2,4,5-trifluorophenyl)-N-(propylsulfonyl)propane-1-sulfonamide (50 mg, 0.1 mmol, 1.0 eq.), phenylboronic acid (13.5 mg, 0.011 mol, 1.1 eq.), Pd(dppf)2Cl2 (4.1 mg, 0.005 mmol, 0.05 eq.) and Na$_2$CO$_3$ (0.21 g, 0.2 mmol, 2.0 eq.) in dioxane and water (9 mL/1 mL) were heated at 80° C. for 4 h under N2 protection, then cooled and concentrated. The resulting residue was purified by flash column chromatography (PE/EA=4/1, v/v) to afford N-(2,4,5-trifluoro-3-(3-phenylquinoxaline-6-carbonyl)phenyl)propane-1-sulfonamide. $^1$H NMR (DMSO-d6, 400 MHz) δ 10.15 (brs, 1 H), 9.78 (s, 1 H), 8.62 (s, 1 H), 8.38 (m, 2 H), 8.32 (brs, 2H), 7.79 (m, 1 H), 7.62 (brs, 3 H), 3.22 (t, 2 H), 1.74 (m, 2 H), 0.97 (t, 3 H).

Example 31

Preparation of N-(2,4,5-trifluoro-3-(3-(4-fluorophenyl)quinoxaline-6-carbonyl)phenyl)propane-1-sulfonamide

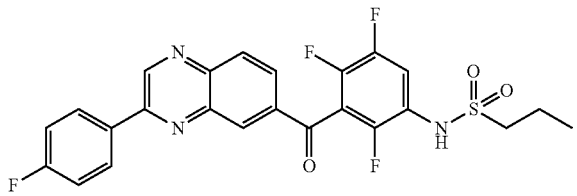 [SMILES: CCCS(=O)(=O)Nc1cc(F)c(F)c(C(=O)c2ccc3ncc(-c4ccc(F)cc4)nc3c2)c1F]

N-(2,4, 5-trifluoro-3-(3-(4-fluorophenyl)quinoxaline-6-carbonyl)phenyl)propane-1-sulfonamide N-(2,4,5-trifluoro-3-(3-(4-fluorophenyl)quinoxaline-6-carbonyl)phenyl)propane-1-sulfonamide was prepared as described for N-(2,4,5-trifluoro-3-(3-phenylquinoxaline-6-carbonyl)phenyl)propane-1-sulfonamide. $^1$H NMR (DMSO-d6, 400 MHz) δ 10.15 (brs, 1 H), 9.78 (s, 1H), 8.62 (s, 1 H), 8.45 (m, 2 H), 8.35 (brs, 2 H), 7.79 (m, 1 H), 7.47 (t, 2 H), 3.22 (t, 2 H), 1.72 (m, 2 H), 0.87 (t, 3 H).

Example 32

Preparation of N-(3-(3-(1H-pyrazol-4-yl)quinoxaline-6-carbonyl)-2,4,5-trifluorophenyl)propane-1-sulfonamide

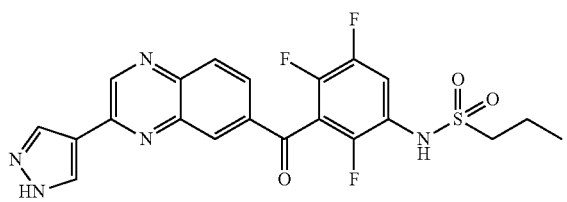 [SMILES: CCCS(=O)(=O)Nc1cc(F)c(F)c(C(=O)c2ccc3ncc(-c4cn[nH]c4)nc3c2)c1F]

N-(3-(3-(1H-pyrazol-4-yl)quinoxaline-6-carbonyl)-2,4,5-trifluorophenyl)propane-1-sulfonamide N-(3-(3-(1H-pyrazol-4-yl)quinoxaline-6-carbonyl)-2,4,5-trifluorophenyl)propane-1-sulfonamide was prepared as described for N-(2,4,5-trifluoro-3-(3-phenylquinoxaline-6-carbonyl)phenyl)propane-1-sulfonamide. LRMS (M−H$^+$) m/z calculated 474.1. found 473.9. $^1$H NMR (DMSO-d6, 400 MHz) δ13.46 (brs, 1 H), 10.16 (brs, 1 H), 9.52 (s, 1 H), 8.76 (s, 1 H), 8.42 (s, 1 H), 8.34 (s, 1 H), 7.78 (brs, 2 H), 7.77 (m, 1 H), 3.22 (t, 3 H), 1.72 (m, 2 H), 0.95 (t, 3 H).

Example 33

Preparation of N-(2,4,5-trifluoro-3-(3-(pyridin-3-yl)quinoxaline-6-carbonyl)phenyl)propane-1-sulfonamide

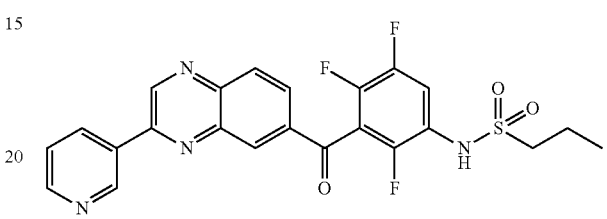

N-(2,4,5-trifluoro-3-(3-(pyridin-3-yl)quinoxaline-6-carbonyl)phenyl)propane-1-sulfonamide N-(2,4,5-trifluoro-3-(3-(pyridin-3-yl)quinoxaline-6-carbonyl)phenyl)propane-1-sulfonamide was prepared as described for N-(2,4,5-trifluoro-3-(3-phenylquinoxaline-6-carbonyl)phenyl)propane-1-sulfonamide. LRMS (M+H$^+$) m/z calculated 487.1. found 486.9. $^1$H NMR (DMSO-d6, 400 MHz) δ 10.15 (brs, 1 H), 9.83 (s, 1 H), 8.84 (d, 2 H), 8.69 (s, 1 H), 8.42 (m, 2 H), 8.31 (d, 2 H), 7.80 (m, 1 H), 3.22 (t, 2 H), 1.72 (m, 2 H), 0.95 (t, 3 H).

Example 34

Preparation of N-(2,4,5-trifluoro-3-(3-(6-methylpyridin-3-yl)quinoxaline-6-carbonyl)phenyl)propane-1-sulfonamide

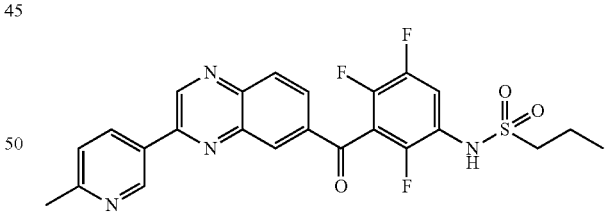

N-(2,4, 5-trifluoro-3-(3-(6-methylpyridin-3-yl)quinoxaline-6-carbonyl)phenyl)propane-1-sulfonamide N-(2,4,5-trifluoro-3-(3-(6-methylpyridin-3-yl)quinoxaline-6-carbonyl)phenyl)propane-1-sulfonamide was prepared as described for N-(2,4,5-trifluoro-3-(3-phenylquinoxaline-6-carbonyl)phenyl)propane-1-sulfonamide. LRMS (M+H$^+$) m/z calculated 501.1. found 500.9. $^1$H NMR (DMSO-d6, 400 MHz) δ 10.15 (brs, 1 H), 9.80 (s, 1 H), 9.41 (s, 1 H), 8.61 (brs, 2 H), 8.33 (brs, 2 H), 7.79 (m, 1 H), 7.50 (d, 1 H), 2.59 (s, 3 H), 3.22 (t, 2 H), 1.72 (m, 2 H), 0.95 (t, 3 H).

Example 35

Preparation of N-(2,4,5-trifluoro-3-(3-(pyridin-3-yl)quinoxaline-6-carbonyl)phenyl)propane-1-sulfonamide

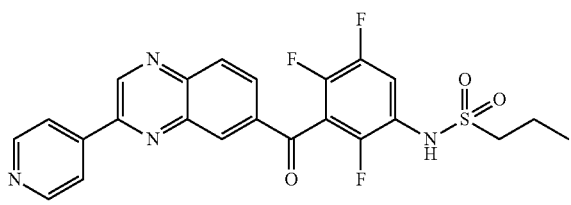 [SMILES: CCCS(=O)(=O)Nc1cc(F)c(F)c(C(=O)c2ccc3ncc(-c4ccncc4)nc3c2)c1F]

N-(2,4,5-trifluoro-3-(3-(pyridin-4-yl)quinoxaline-6-carbonyl)phenyl)propane-1-sulfonamide N-(2,4,5-trifluoro-3-(3-(pyridin-4-yl)quinoxaline-6-carbonyl)phenyl)propane-1-sulfonamide was prepared as described for N-(2,4,5-trifluoro-3-(3-phenylquinoxaline-6-carbonyl)phenyl)propane-1-sulfonamide. LRMS (M+H$^+$) m/z calculated 487.1. found 486.9. $^1$H NMR (DMSO-d6, 400 MHz) δ 10.15 (brs, 1 H), 9.83 (s, 1 H), 8.84 (d, 2 H), 8.69 (s, 1 H), 8.42 (m, 2 H), 8.31 (d, 2 H), 7.80 (m, 1 H), 3.22 (t, 2 H), 1.72 (m, 2 H), 0.95 (t, 3 H).

Example 36

Preparation of N-(3-(3-cyanoquinoxaline-6-carbonyl)-2,4,5-trifluorophenyl)propane-1-sulfonamide

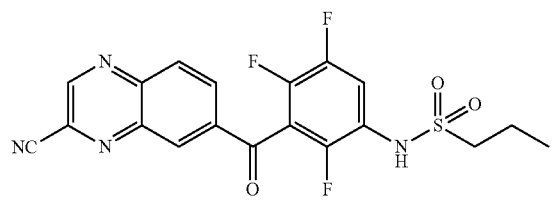 [SMILES: CCCS(=O)(=O)Nc1cc(F)c(F)c(C(=O)c2ccc3ncc(C#N)nc3c2)c1F]

N-(3-(3-cyanoquinoxaline-6-carbonyl)-2,4,5-trifluorophenyl)propane-1-sulfonamide

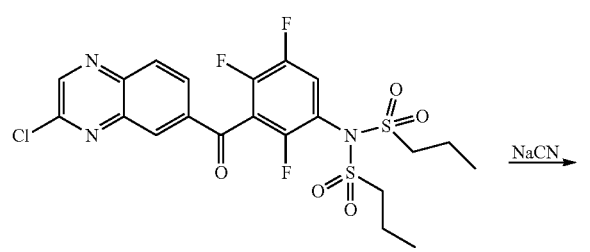

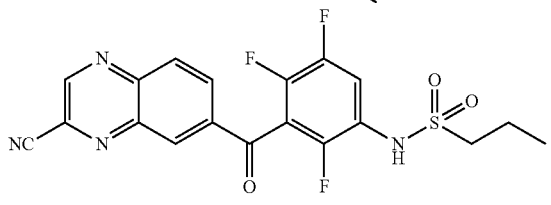

A mixture of N-(3-(3-chloroquinoxaline-6-carbonyl)-2,4,5-trifluorophenyl)-N-(propylsulfonyl)propane-1-sulfonamide (50 mg, 0.1 mmol, 1.0 eq.) and NaCN (9.8 mg, 0.002 mol, 2.0 eq.) in DMF (10 mL) was heated at 100° C. for 10 h under N$_2$ protection. The mixture was cooled, diluted with water and extracted with EA (20 mL×3). The combined organic layers were washed with water, saline and dried over Na$_2$SO$_4$, filtered, and concentrated. The resulting residue was purified by flash column chromatography (PE/EA=4/1, v/v) to afford N-(3-(3-cyanoquinoxaline-6-carbonyl)-2,4,5-trifluorophenyl)propane-1-sulfonamide. LRMS (M+H$^+$) m/z calculated 435.1. found 435.0. $^1$H NMR (DMSO-d6, 400 MHz) δ 10.11 (brs, 1 H), 9.52 (s, 1 H), 8.75 (s, 1 H), 8.52 (d, 1 H), 8.41 (d, 1H), 7.79 (m, 1 H), 3.22 (t, 2 H), 1.72 (m, 2 H), 0.95 (t, 3 H).

Example 37

Preparation of N-(3-(3-cyanoquinoxaline-6-carbonyl)-2,4-difluorophenyl)propane-1-sulfonamide

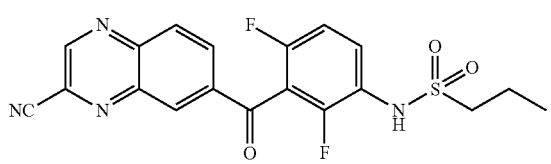 [SMILES: CCCS(=O)(=O)Nc1ccc(F)c(C(=O)c2ccc3ncc(C#N)nc3c2)c1F]

N-(3-(3-cyanoquinoxaline-6-carbonyl)-2,4-difluorophenyl)propane-1-sulfonamide

N-(3-(3-cyanoquinoxaline-6-carbonyl)-2,4-difluorophenyl)propane-1-sulfonamide was prepared as described for N-(3-(3-cyanoquinoxaline-6-carbonyl)-2,4,5-trifluorophenyl)propane-1-sulfonamide. LRMS (M+H$^+$) m/z calculated 417.1. found 417.0. $^1$H NMR (CDCl$_3$, 400 MHz) δ 9.19 (s, 1 H), 8.48-8.56 (m, 2 H), 8.34-8.37 (d, 1 H), 7.80-7.86 (m, 1 H), 7.09-7.14 (m, 1 H), 6.54 (s, 1 H), 3.11-3.15 (m, 2 H), 1.88-1.94 (m, 2 H), 1.06-1.10 (t, 3 H).

Example 38

Preparation of N-(4-fluoro-3-(quinoxaline-6-carbonyl)phenyl)propane-1-sulfonamide

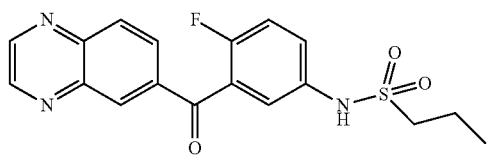 [SMILES: CCCS(=O)(=O)Nc1ccc(F)c(C(=O)c2ccc3nccnc3c2)c1]

N-(4-fluoro-3-(quinoxaline-6-carbonyl)phenyl)propane-1-sulfonamide

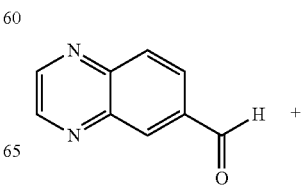

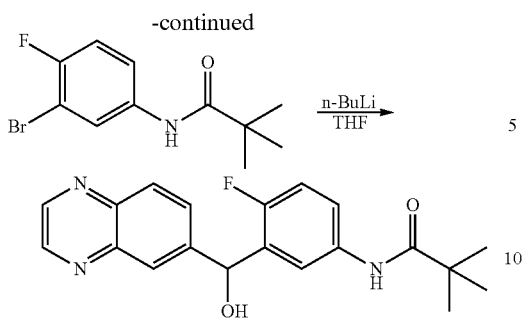

To a solution of N-(3-bromo-4-fluorophenyl)pivalamide (9.48 g, 34.6 mmol, 1.2 eq.) in THF (100 mL) cooled at −78° C. was added n-BuLi (27.6 mL, 69 mmol, 2.4 eq.) dropwise. The resulting mixture was stirred at −78° C. for 1 h, then was added a solution of quinoxaline-6-carbaldehyde (4.5 g, 28.8 mmol, 1.0 eq.) in THF (200 mL) dropwise. The mixture was stirred at −78° C. for 1 h, then quenched by the addition of NH₄Cl solution. The mixture was extracted with EA (100 mL×3) and the combined organic layers were dried over Na₂SO₄ and concentrated. The resulting residue was purified by flash column chromatography (PE/EA=1/1, v/v) to afford N-(4-fluoro-3-(hydroxy(quinoxalin-6-yl)methyl)phenyl)pivalamide as a yellow foam (5.16 g, 50.7%).

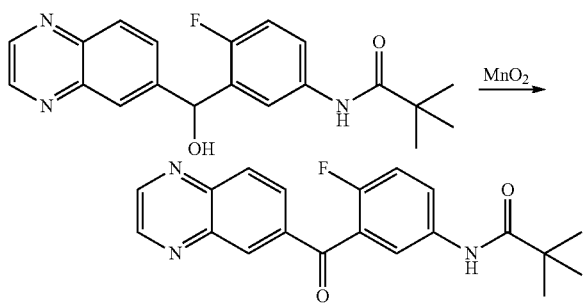

To the solution of N-(4-fluoro-3-(hydroxy(quinoxalin-6-yl)methyl)phenyl)pivalamide (5.16 g, 14.6 mmol, 1.0 eq.) in DCM (50 mL) was added MnO₂ (6.4 g, 73 mmol, 5.0 eq.). The resulting mixture was stirred at 50° C. overnight. The solid was removed by filtration and the filtrate was concentrated. The resulting residue was purified by flash column chromatography (PE/EA=2/1, v/v) to afford N-(4-fluoro-3-(quinoxaline-6-carbonyl)phenyl)pivalamide as a yellow foam (4.7 g, 92%).

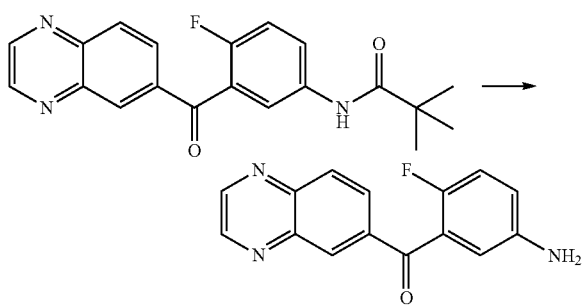

To a solution of N-(4-fluoro-3-(quinoxaline-6-carbonyl)phenyl)pivalamide (4.7 g, 13.5 mmol, 1.0 eq.) in HOAc (60 mL) was added conc. HCl (30 mL). The mixture was stirred at 110° C. for 4 h, then poured onto ice. The mixture was basified to pH=10 by the addition of 1N NaOH aqueous solution and extracted with DCM (100 mL×3). The combined organic layers were dried over Na₂SO₄ and concentrated. The resulting residue was purified by flash column chromatography (PE/EA=1/2, v/v) to afford (5-amino-2-fluorophenyl)(quinoxalin-6-yl)methanone (3.5 g, 99%) which was used in the next step without further purification.

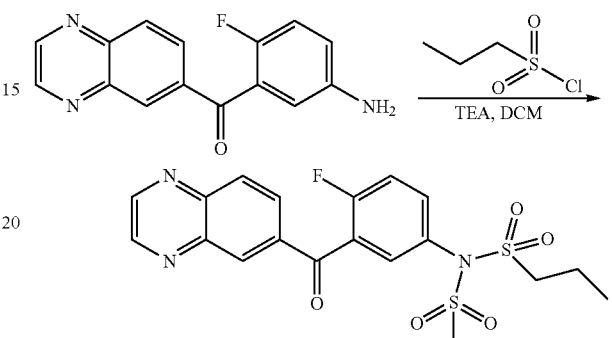

To a solution of (5-amino-2-fluorophenyl)(quinoxalin-6-yl)methanone (50 mg, 0.187 mmol, 1.0 eq.) in DCM (10 mL) were added TEA (0.26 mL, 1.87 mmol, 10.0 eq.) and propane-1-sulfonyl chloride (133 mg, 0.935 mmol, 5.0 eq.). The resulting mixture was stirred at rt for 1 h, then washed with water and extracted with DCM (20 mL×3). The combined organic layers were dried over Na₂SO₄, filtered and concentrated. The resulting residue was purified by flash column chromatography (PE/EA=2/1, v/v) to afford N-(4-fluoro-3-(quinoxaline-6-carbonyl)phenyl)-N-(propylsulfonyl)propane-1-sulfonamide (50 mg, 56.8%).

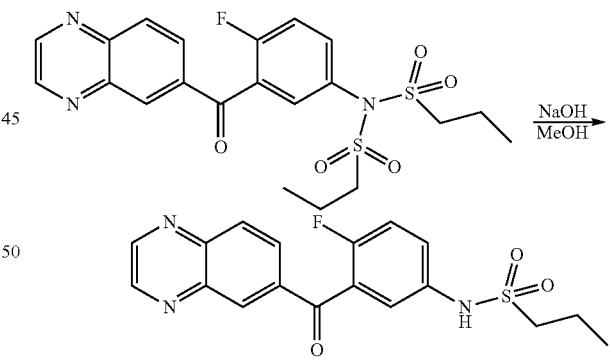

To a solution of N-(4-fluoro-3-(quinoxaline-6-carbonyl)phenyl)-N-(propylsulfonyl)propane-1-sulfonamide (50 mg, 0.10 mmol, 1.0 eq.) in MeOH (10 mL) was added NaOH aqueous solution (1 N, 0.22 mL, 0.22 mmol, 2.2 eq.). The resulting mixture was stirred at rt for 1 h, then concentrated. The resulting residue was purified by flash column chromatography (PE/EA=1/1, v/v) to afford N-(4-fluoro-3-(quinoxaline-6-carbonyl)phenyl)propane-1-sulfonamide (33.4 mg, 89.5%). LRMS (M+H⁺) m/z calculated 374.1. found 374.1. ¹H NMR (CDCl₃, 400 MHz) δ 8.94-8.97 (dd, 2 H), 8.46-8.47 (m, 1 H), 8.31-8.34 (m, 1 H), 8.23-8.25 (m, 1 H), 7.50-7.54 (m, 1 H), 7.46-7.48 (m, 1 H), 7.19-7.23 (t, 1 H), 6.80 (s, 1 H), 3.10-3.14 (m, 2 H), 1.86-1.92 (m, 2 H), 1.04-1.08 (t, 3 H).

Example 39

Preparation of N-(3,4-difluoro-5-(quinoxaline-6-carbonyl)phenyl)propane-1-sulfonamide

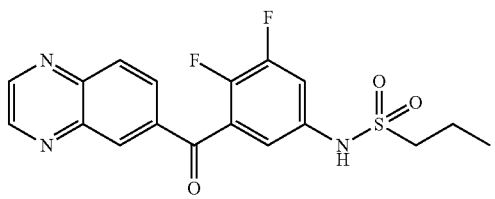 [SMILES: CCCS(=O)(=O)Nc1cc(F)c(F)c(C(=O)c2ccc3nccnc3c2)c1]

N-(3,4-difluoro-5-(quinoxaline-6-carbonyl)phenyl)propane-1-sulfonamide

N-(3,4-difluoro-5-(quinoxaline-6-carbonyl)phenyl)propane-1-sulfonamide was prepared as described for N-(4-fluoro-3-(quinoxaline-6-carbonyl)phenyl)propane-1-sulfonamide. LRMS (M−H⁻) m/z calculated 390.4. found 390.1. ¹H NMR (CDCl$_3$, 400 MHz) δ 8.88-8.91 (m, 2 H), 8.39 (s, 1 H), 8.17-8.26 (m, 2 H), 7.38-7.42 (m, 1 H), 7.11-7.14 (m, 1 H), 3.05-3.09 (m, 2 H), 1.79-1.85 (m, 2 H), 0.98-1.02 (t, 3 H).

Example 40

Preparation of N-(3,4-difluoro-5-(3-morpholinoquinoxaline-6-carbonyl)phenyl)propane-1-sulfonamide

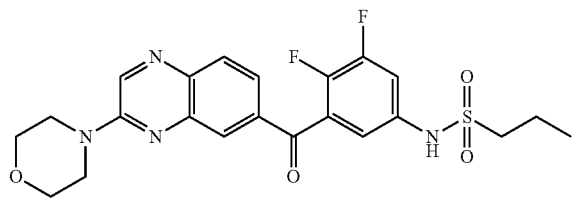 [SMILES: CCCS(=O)(=O)Nc1cc(F)c(F)c(C(=O)c2ccc3ncc(N4CCOCC4)nc3c2)c1]

N-(3,4-difluoro-5-(3-morpholinoquinoxaline-6-carbonyl)phenyl)propane-1-sulfonamide N-(3,4-difluoro-5-(3-morpholinoquinoxaline-6-carbonyl)phenyl)propane-1-sulfonamide was prepared as described for N-(4-fluoro-3-(quinoxaline-6-carbonyl)phenyl)propane-1-sulfonamide. LRMS (M+H⁺) m/z calculated 477.1. found 477.1. ¹H NMR (CDCl$_3$, 400 MHz) δ 8.66 (s, 1 H), 7.99-8.01 (m, 1 H), 7.91-7.94 (m, 2 H), 7.43-7.44 (m, 1 H), 7.08 (m, 1 H), 6.57 (s, 1 H), 3.78-3.89 (m, 8 H), 3.11-3.15 (m, 2 H), 1.86-1.92 (m, 2 H), 1.06-1.09 (t, 3 H).

Example 41

Preparation of N-(3-fluoro-5-(quinoxaline-6-carbonyl)phenyl)propane-1-sulfonamide

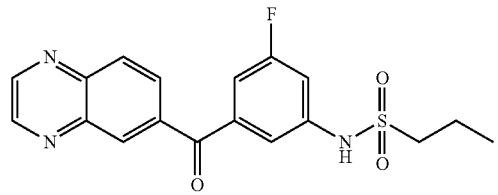 [SMILES: CCCS(=O)(=O)Nc1cc(F)cc(C(=O)c2ccc3nccnc3c2)c1]

N-(3-fluoro-5-(quinoxaline-6-carbonyl)phenyl)propane-1-sulfonamide

N-(3-fluoro-5-(quinoxaline-6-carbonyl)phenyl)propane-1-sulfonamide was prepared as described for N-(4-fluoro-3-(quinoxaline-6-carbonyl)phenyl)propane-1-sulfonamide. LRMS (M+H⁺) m/z calculated 374.1. found 374.0. ¹H NMR (CDCl3, 300 MHz) δ 8.98-8.99 (d, 2 H), 8.49 (s, 1 H), 8.27 (s, 1 H), 7.32-7.43 (m, 3 H), 6.93 (s, 1 H), 3.15-3.20 (m, 2 H), 1.86-1.94 (m, 2 H), 1.05-1.10 (t, 3H).

Example 42

Preparation of N-(4-fluoro-3-(3-morpholinoquinoxaline-6-carbonyl)phenyl)propane-1-sulfonamide

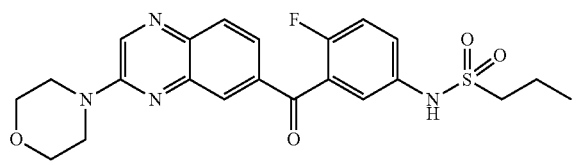 [SMILES: CCCS(=O)(=O)Nc1ccc(F)c(C(=O)c2ccc3ncc(N4CCOCC4)nc3c2)c1]

N-(4-fluoro-3-(3-morpholinoquinoxaline-6-carbonyl)phenyl)propane-1-sulfonamide

N-(4-fluoro-3-(3-morpholinoquinoxaline-6-carbonyl)phenyl)propane-1-sulfonamide was prepared as described for N-(4-fluoro-3-(quinoxaline-6-carbonyl)phenyl)propane-1-sulfonamide. LRMS (M+H⁺) m/z calculated 459.1. found 459.2. ¹H NMR (CDCl$_3$, 300 MHz) δ=8.65 (s, 1 H), 8.03 (m, 3 H), 7.49-7.52 (m, 1 H), 7.38-7.40 (m, 1 H), 7.18-7.22 (t, 1 H), 6.60 (s, 1 H), 3.78-3.88 (m, 8 H), 3.09-3.13 (m, 2 H), 1.86-1.92 (m, 2 H), 1.04-1.08 (t, 3 H).

Example 43

Preparation of N-(3-fluoro-5-(3-morpholinoquinoxaline-6-carbonyl)phenyl)propane-1-sulfonamide

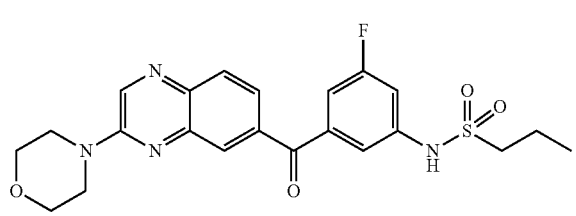 [SMILES: CCCS(=O)(=O)Nc1cc(F)cc(C(=O)c2ccc3ncc(N4CCOCC4)nc3c2)c1]

N-(3-fluoro-5-(3-morpholinoquinoxaline-6-carbonyl)phenyl)propane-1-sulfonamide

N-(3-fluoro-5-(3-morpholinoquinoxaline-6-carbonyl)phenyl)propane-1-sulfonamide was prepared as described for N-(4-fluoro-3-(quinoxaline-6-carbonyl)phenyl)propane-1-sulfonamide. LRMS (M+H$^+$) m/z calculated 459.1. found 459.2. $^1$H NMR (CDCl$_3$, 300 MHz) δ 8.68 (s, 1 H), 8.00-8.03 (m, 2 H), 7.83-7.88 (m, 1 H), 7.28-7.39 (m, 3 H), 6.89-6.92 (m, 1 H), 3.80-3.91 (m, 8 H), 3.14-3.19 (m, 2 H), 1.86-1.93 (m, 2 H), 1.05-1.09 (t, 3 H).

Example 44

Inhibitory Activity Against Kinases BRAF and BRAF V600E

Inhibitory activities of compounds against BRAF or BRAF V600E were measured by Invitrogen using Z'-LYTE® Method as briefly described in the following.

4× Test compounds are dissolved in 1% DMSO. Kinase reaction mixture consists of 0.09-0.34 ng B-Raf (or 0.002-0.006 ng BRAF V600E), 1× inactive MAP2K1 (MEK1)/inactive MAPK1 (ERK2), and 2 µM Ser/Thr 03 in 50 mM HEPES pH 7.5, 0.01% BRIJ-35, 10 mM MgCl2, 1 mM EGTA. ATP solutions are diluted to a 4×ATP working concentration in Kinase Buffer (50 mM HEPES pH 7.5, 0.01% BRIJ-35, 10 mM MgCl2, 1 mM EGTA).

Reaction starts by 30-second shaking of mixture consisting of 2.5 µL4× test compound, 2.5 µL 2× kinase reaction mixture and 2.5 µL 4×ATP Solution on Bar-coded Corning, low volume NBS, black 384-well plate (Corning Cat. #3676). Then the mixture is incubated for 60-minute at room temperature for the kinase reaction, followed by addition of 5 µL of a 1:1024 dilution of development reagent A and 30-second plate shake. The mixture is then incubated for another 60-minute at room temperature for development reaction. Finally fluorescence is read by plate reader. Table 2 shows % inhibition at 1 µM of several compounds of the invention using Z'-LYTE® method. The scale utilized in Table 2 is as follows: +++ more than 89% inhibition; ++ between 70% and 89% inhibition; and + less than 70% inhibition.

TABLE 2

Biological activity of several illustrative compounds against BRAF and BRAF V600E

| Compound | BRAF % inhibition | BRAF V600E % inhibition |
|---|---|---|
| C01 | ++ | +++ |
| C02 | ++ | +++ |
| C03 | ++ | +++ |
| C04 | +++ | +++ |
| C05 | ++ | +++ |
| C06 | ++ | +++ |
| C07 | + | ++ |
| C08 | + | + |
| C09 | +++ | +++ |
| C10 | +++ | ++ |
| C11 | ++ | +++ |
| C12 | ++ | +++ |
| C13 | +++ | +++ |
| C14 | +++ | ++ |
| C15 | − | + |
| C16 | − | + |
| C17 | − | + |
| C18 | − | + |
| C37 | − | ++ |

Example 45

Inhibitory Activities Against BRAF and BRAF V600E Using LanthaScreen™ Kinase Assay The inhibitory activities of compounds against BRAF or BRAF V600E protein were measured using Invitrogne's LanthaScreen™ kinase assay which is based on fluorescein-labeled MAP2K1 as a substrate. The assay procedure is described as follows.

Reagents:
All of reagents were purchased from Invitrogen.

| Reagents | Concentration for use |
|---|---|
| BRAF | 0.2 ng/µL |
| BRAF V600E | 0.002 ng/µL |
| ATP | BRAF: 1 µM |
|  | BRAF V600E: 10 µM |
| Fl-Substrate | 200 nM |
| EDTA | Ready to use |
| Tb-anti-pMAP2K1[pS$^{217/221}$] Ab | Ready to use |
| Reaction Buffer | 5× |
| Buffer | Ready to use | i. Solutions of compounds were made by dissolving in DMSO. 3-fold serial dilutions of each inhibitor were prepared from a stock solution. The concentration used was 10 µM in assays. The compounds were screened in 1% DMSO (final) in the well.
ii. 4 µL of BRAF or BRAFV600E were added to individual wells of 384 well assay plate (Greiner #784076).
iii. 2 µL compounds were added to each well.
iv. 4 µL of reaction buffer were added.
v. The mixture was incubated at room temperature for 5 minutes.
vi. 2 µL of the ATP+Fl-substrate solution was added to start the reaction.
vii. The plate and incubator were briefly shaken at room temperature for 60 minutes on a plate shaker.
viii. 4 µL of EDTA and 4 µL of Tb-anti-pMAP2K1 [pS$^{217/221}$]Ab were added respectively to each well and mixed briefly.
ix. The assay plate and incubator were covered for 1 h at room temperature before reading on PHERAstar FS.
x. The resulting TR-FRET emission ratios were plotted against the concentrations of inhibitor, and the data was fitted to a sigmoidal dose-response curve with a variable slope. IC$_{50}$ concentrations from the curve were calculated.

Table 3 shows IC$_{50}$ values of several compounds of the invention using LanthaScreen™ kinase assay. The scale utilized in Table 3 is as follows: ++++ less than 50 nM; +++ between 50 and 100 nM; ++ between 100 nM and 1M; and + greater than 1 µM.

TABLE 3

Biological activity of several illustrative compounds against BRAF and BRAF V600E using LanthaScreen ™ kinase assay

| | IC$_{50}$ | |
|---|---|---|
| Compound | BRAF | BRAF V600E |
| C04 | +++ | ++++ |
| C06 | ++ | ++++ |
| C18 | +++ | ++++ |
| C19 | ++ | ++ |
| C37 | ++ | +++ |

TABLE 3-continued

Biological activity of several illustrative compounds against BRAF and BRAF V600E using LanthaScreen™ kinase assay

| Compound | IC$_{50}$ BRAF | BRAF V600E |
|---|---|---|
| C09 | +++ | ++++ |
| C26 | ++ | ++++ |
| C28 | ++ | +++ |
| C30 | ++++ | ++++ |
| C33 | ++++ | ++++ |
| C34 | ++++ | ++++ |
| C35 | +++ | ++++ |
| C36 | +++ | ++++ |
| C24 | ++++ | ++++ |
| C27 | ++++ | ++++ |
| C29 | ++ | ++ |
| C41 | + | + |
| C38 | ++ | ++ |
| C23 | ++++ | ++++ |
| C20 | +++ | ++++ |
| C21 | ++++ | ++++ |
| C40 | +++ | ++++ |
| C22 | +++ | +++ |

Example 46

Inhibition of Cancer Cell Growth by Compounds Using MTT Assay

Inhibition of cell growth by compounds was measured using MTT assay (Mosmann, T., *Journal of Immunological Methods*, 1983, 65, 55-63). Tumor cell lines were purchased from ATCC (American Type Culture Collection, Manassas, Va.). All cell lines were maintained in RPMI 1640 (Hyclone) supplemented with 10% fetal bovine serum (FBS, Hyclone), glutamine (2 mM, Hyclone), and antibiotics (penicillin 100 U/mL and streptomycin 50 μg/mL) at 37° C. in a humidified atmosphere of 5% $CO_2$ in air. Taxol (as a positive control, Sigma) and compounds were dissolved in DMSO (Sigma), and the final concentration of DMSO in the medium was 1%. Tumor cells were plated in 96-well plates at densities of about 4000 cells/well of a 96-well plate and allowed to adhere/grow for 24 h. They were then treated with various concentrations of drug for 72 h. 3-(4,5-Dimethylthiazol-2-yl)-2,5-diphenyltetrazolium bromide (MTT, Sigma) was used to determine the number of viable cells at the time of compound addition and the number of cells remaining after 72 h compound exposure. The number of cells remaining after 72 h was compared to the number of viable cells at the time of compound addition by measuring the absorbance at 570 nm, allowing for the calculation of growth inhibition.

All concentrations of compounds were tested in triplicate and controls were averaged over 4 wells. IC$_{50}$ was calculated by plotting the concentration of compound vs the percentage of inhibition in treated wells using GraphPad Prism 5. Data for representative compounds are shown below.

Table 4 shows IC$_{50}$ values of several compounds of the invention in A549 and A375 cells. The scale utilized in Table 4 is as follows: +++ less than 500 nM; ++ between 500 nM and 1 μM; and + greater than 1 μM.

TABLE 4

In vitro activity of several illustrative compounds in A549 and A375 cells

| Compound | IC$_{50}$ A549 | A375 |
|---|---|---|
| C01 | +++ | +++ |
| C02 | ++ | ++ |
| C03 | + | + |
| C05 | +++ | ++ |
| C07 | + | ++ |
| C08 | + | + |
| C10 | + | +++ |
| C11 | + | + |
| C13 | + | + |
| C14 | + | +++ |
| C15 | + | + |
| C16 | + | + |
| C17 | + | + |
| C18 | + | + |
| C37 | + | + |

Example 47

Inhibition of Cancer Cell Growth by Compounds Using MTT or MTS Assay

A375 (human melanoma cell, BRAF V600E Mutant), CHL-1 (human melanoma cell, BRAF wild type), SK-MEL-28 (human melanoma cell, BRAF V600E Mutant) and SK-MEL-31 (human melanoma cell, Braf WT Mutant) were purchased from ATCC (American Type Culture Collection, Manassas, Va.). All cell lines were maintained in RPMI 1640 (Hyclone) or DMEM (Hyclone) supplemented with 10% fetal bovine serum (FBS, Hyclone), glutamine (2 mM, Hyclone), and antibiotics (penicillin 100 U/mL and streptomycin 50 μg/mL) at 37° C. in a humidified atmosphere of 5% $CO_2$ in air.

To test IC$_{50}$ of inhibition of individual compounds against each cell line, A375, SK-MEL-28 and SK-MEL-31 cells were first plated in 96-well plates at densities of 3000 cells/well, and CHL-1 2500 cells/well. Cells were then incubated to allow cells to adhere and grow for 24 h. Cells were then treated with a series of concentrations of compounds for 72 h. The highest concentration of compounds was 10 μM for A375 and SK-MEL-28 cells and 100 μM for CHL-1 and SK-MEL-31 cells. Cells were then removed from the incubator and medium was removed by inverting and tapping the plates. 100 μL of MTT (0.5 mg/ml) or 10 μL or MTS was added to each well followed by an incubated at 37° C. for 4 h. Then MTT was removed and 200 μL of DMSO was added to each well, followed by reading the ODs at 570 nm after a 5 second shaking cycle in a 96-well spectrophotometer. For MTS method, MTS was not removed, and the incubated solutions were directly put in a 96-well spectrophotometer for the reading of the ODs at 492 nm.

IC$_{50}$ was calculated by plotting the concentration of compound vs the percentage of inhibition in treated wells using GraphPad Prism 5. Table 5 shows IC$_{50}$ values of several compounds of the invention by MTT or MTS assay. The scale utilized in Table 5 is as follows: +++ less than 500 nM; ++ between 500 nM and 1 μM; and + greater than 1 μM.

TABLE 5

In vitro activity of several illustrative compounds in cells

| | $IC_{50}$ | | | |
|---|---|---|---|---|
| Compound | A375 | SK-MEL-28 | CHL-1 | SK-MEL-31 |
| C04 | +++ | +++ | No inhibition | No inhibition |
| C06 | +++ | — | No inhibition | — |
| C09 | +++ | +++ | No inhibition | No inhibition |
| C12 | +++ | ++ | No inhibition | No inhibition |
| C19 | + | — | — | — |
| C24 | +++ | — | — | — |
| C27 | +++ | — | — | — |
| C26 | ++ | — | — | — |
| C28 | ++ | — | — | — |
| C29 | +++ | — | — | — |
| C30 | +++ | — | — | — |
| C33 | +++ | — | — | — |
| C34 | +++ | — | — | — |
| C35 | + | — | — | — |
| C36 | ++ | — | — | — |
| C38 | +++ | — | — | — |
| C23 | +++ | — | — | — |
| C20 | +++ | — | — | — |
| C21 | +++ | — | — | — |
| C40 | +++ | — | — | — |
| C22 | +++ | — | — | — |

Example 48

Inhibition of Tumor Growth in Xenograft Model

Cells were implanted in BALB/c female nude mice and grown as tumor xenografts. When tumors achieved 120-200 mm³, mice were assigned into treatment and control groups using randomized block design based upon their tumor volumes. Each group contained 6 tumor-bearing mice. Tumors were measured twice weekly in two dimensions using a caliper, and the tumor volume was calculated from two-dimensional measurements using the equation $V=0.5 \times a \times b^2$ where a and b are the long and short diameters of the tumor, respectively. Relative tumor volume (RTV) was defined as $TV_t/TV_i$, the ratio of the volume on a given day ($TV_t$) and the volume at the start of treatment ($TV_i$). Relative tumor growth rate (T/C) was defined as $RTV_T/RTV_C$, the ratio of relative tumor volume of treatment group ($RTV_T$) and relative tumor volume of control group ($RTV_C$) on a given day. Inhibition of tumor growth in a A375 tumor xenograft model is shown below in Table 6 for a compound of Table 1.

TABLE 6

In vivo activity of an illustrative compound in A375 tumor model

| | Dose (mg/kg) | Schedule | Route | Tumor Volume Pre-treatment (mm³) | Tumor Volume Post-treatment (mm³) | T/C |
|---|---|---|---|---|---|---|
| Vehicle | — | b.i.d. × 20 | i.g. | 139 | 1512 | — |
| Compound | 12.5 | b.i.d. × 20 | i.g. | 146 | 109 | 6.8%** |
| Cisplatin | 6 | q7d × 3 | i.p. | 136 | 647 | 44.4%* |

*p < 0.05;
**p < 0.01

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A method of treating a BRAF-mediated disorder by inhibiting BRAF in a subject suffering from said disorder, the method comprising administering to the subject a therapeutically effective amount of a compound or pharmaceutically acceptable salt of Formula I:

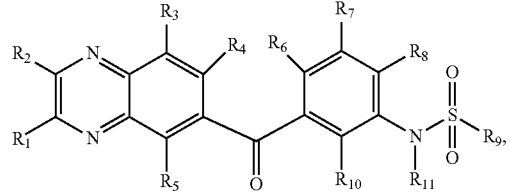

Formula I wherein
$R_1$ is hydrogen, cyano, halogen, optionally substituted lower alkyl, optionally substituted alkoxy, optionally substituted amino, optionally substituted aryl, optionally substituted heterocycloalkyl, or optionally substituted heteroaryl;

$R_2$, $R_3$, $R_4$ and $R_5$ are hydrogen;

$R_6$, $R_7$, $R_8$, and $R_{10}$ are independently hydrogen, cyano, sulfanyl, or halo;

$R_9$ is optionally substituted alkyl, optionally substituted cycloalkyl, optionally substituted heterocycloalkyl, optionally substituted aryl, or optionally substituted heteroaryl; and $R_{11}$ is hydrogen, optionally substituted alkyl, optionally substituted cycloalkyl, optionally substituted heterocycloalkyl, optionally substituted aryl, or optionally substituted heteroaryl.

2. The method of claim 1, wherein the subject expresses mutant BRAF.

3. The method of claim 1, wherein the BRAF has a mutation in codon 600.

4. The method of claim 1, wherein the BRAF is a BRAF-V600E mutant.

5. The method of claim 1, further comprising administering an additional anti-cancer and/or cytotoxic agent.

6. The method of claim 1, wherein $R_1$ is optionally substituted aryl, optionally substituted heterocycloalkyl, or optionally substituted heteroaryl.

7. The method of claim 1, wherein $R_6$ and $R_{10}$ are independently fluoro or chloro.

8. The method of claim 1, wherein $R_9$ is optionally substituted lower alkyl, optionally substituted aryl, or optionally substituted heteroaryl.

9. The method of claim 1, wherein $R_{11}$ is hydrogen or optionally substituted lower alkyl.

10. The method of claim 1, wherein the subject expresses a BRAF V600E mutation.

11. The method of claim 1, wherein the disorder is selected from the group consisting of melanoma, non-small cell lung cancer, colon cancer, thyroid cancer and ovarian cancer.

* * * * *